United States Patent
Boudreault et al.

(10) Patent No.: US 9,673,401 B2
(45) Date of Patent: Jun. 6, 2017

(54) ORGANIC ELECTROLUMINESCENT MATERIALS AND DEVICES

(71) Applicant: Universal Display Corporation, Ewing, NJ (US)

(72) Inventors: Pierre-Luc Boudreault, Pennington, NJ (US); Alexey Dyatkin, Ambler, PA (US); Chuanjun Xia, Lawrenceville, NJ (US); Hitoshi Yamamoto, Pennington, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 419 days.

(21) Appl. No.: 13/930,997

(22) Filed: Jun. 28, 2013

(65) Prior Publication Data
US 2015/0001471 A1   Jan. 1, 2015

(51) Int. Cl.
| | | |
|---|---|---|
| H01L 51/50 | (2006.01) | |
| H01L 51/00 | (2006.01) | |
| C07D 403/04 | (2006.01) | |
| C07D 403/10 | (2006.01) | |
| C07D 471/04 | (2006.01) | |

(52) U.S. Cl.
CPC ........ *H01L 51/0067* (2013.01); *C07D 403/04* (2013.01); *C07D 403/10* (2013.01); *C07D 471/04* (2013.01); *H01L 51/0072* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

European Patent Office, European Search Report regarding corresponding European Application No. 14173684.3 issued Mar. 4, 2015, pp. 1-8.

(Continued)

*Primary Examiner* — Gregory Clark
(74) *Attorney, Agent, or Firm* — Duane Morris LLP

(57) ABSTRACT

The present disclosure generally relates to novel compounds containing carbazole and triazine with different number of phenyl units attached to its core. In particular, the disclosure relates to compositions and/or devices comprising these compounds as hosts for PHOLEDs.

19 Claims, 3 Drawing Sheets

(56) References Cited

U.S. PATENT DOCUMENTS

| | | |
|---|---|---|
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0137239 A1* | 7/2003 | Matsuura et al. ............ 313/503 |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0086745 A1* | 5/2004 | Iwakuma ............ C07D 401/10 |
| | | 428/690 |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251918 A1* | 11/2006 | Iwakuma et al. ............ 428/690 |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2012/0086329 A1 | 4/2012 | Dyatkin |
| 2013/0048955 A1 | 2/2013 | Lee et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2009021336 | 1/2009 |
| KR | 20120029751 | 3/2012 |
| KR | 10-20120092908 A | 8/2012 |
| KR | 20120092908 | 8/2012 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009069442 | 6/2009 |
| WO | 2009086028 | 7/2009 |
| WO | 2009100991 | 8/2009 |
| WO | 2010114264 | 10/2010 |
| WO | 2011049325 | 4/2011 |
| WO | 2011081061 | 7/2011 |
| WO | 2011105161 | 9/2011 |
| WO | 2011126224 | 10/2011 |
| WO | 2012173079 | 12/2012 |
| WO | 2013012298 | 1/2013 |
| WO | 2014146752 A1 | 9/2014 |

OTHER PUBLICATIONS

Partial European Search Report issued on Nov. 6, 2014 for corresponding European Application No. 14173684.3.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

(56) References Cited

OTHER PUBLICATIONS

Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 3, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylbory1)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

Formula I

Formula II

ORGANIC ELECTROLUMINESCENT MATERIALS AND DEVICES

FIELD OF THE INVENTION

The present disclosure generally relates to novel compounds containing carbazole and triazine with different number of phenyl units attached to their core. In particular, the disclosure relates to compositions and/or devices comprising these compounds as hosts for PHOLEDs.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

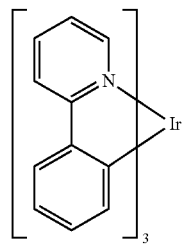

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an aspect of the present disclosure, a compound having a structure according to Formula I:

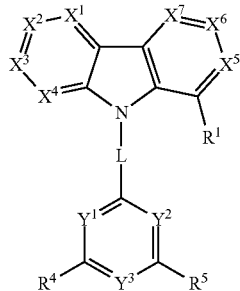

Formula I wherein $R^1$, $R^4$ and $R^5$ are independently selected from group consisting of non-fused aryl, non-fused heteroaryl, and combinations thereof; wherein L is selected from the group consisting of a bond, non-fused aryl, non-fused heteroaryl, and combinations thereof; wherein $X^1$, $X^2$, $X^3$, $X^4$, $X^5$, $X^6$, $X^7$, $Y^1$, $Y^2$, and $Y^3$ are each independently selected from the group consisting of CR and N; wherein at least two of $Y^1$, $Y^2$, and $Y^3$ are N; and wherein each R can be same or different, and is independently selected from the group consisting of hydrogen, deuterium, non-fused aryl, non-fused heteroaryl and combinations thereof, is provided.

In one embodiment, $R^1$ is selected from the group consisting of phenyl, biphenyl, terphenyl, tetraphenyl, pentaphenyl, pyridine, phenyl pyridine and pyridyl phenyl. In one embodiment, the compound of the claim 1, wherein L is selected from the group consisting of phenyl, pyridyl, biphenyl, terphenyl and a bond. In one embodiment, $R^4$ is selected from the group consisting of phenyl, pyridyl, biphenyl, and terphenyl. In one embodiment, $R^5$ is selected from the group consisting of phenyl, pyridyl, biphenyl, and terphenyl.

In one aspect, the compound consists of a compound having a structure according to Formula II:

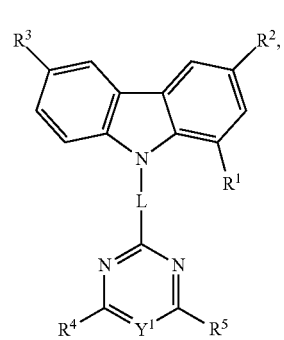

Formula II wherein $R_2$ and $R_3$ can be same or different, and independently selected from the group consisting of hydrogen, deuterium, non-fused aryl, non-fused heteroaryl and combinations thereof.

In one embodiment, the compound having a structure according to Formula II is selected from the group consisting of Compound 1 through Compound 602 listed in the table below, wherein $Y^1$, $R^1$, $R^2$, $R^3$, $R^4$, $R^5$ and L are as defined and wherein C is Carbon, N is nitrogen, H is hydrogen, $A^1$ is

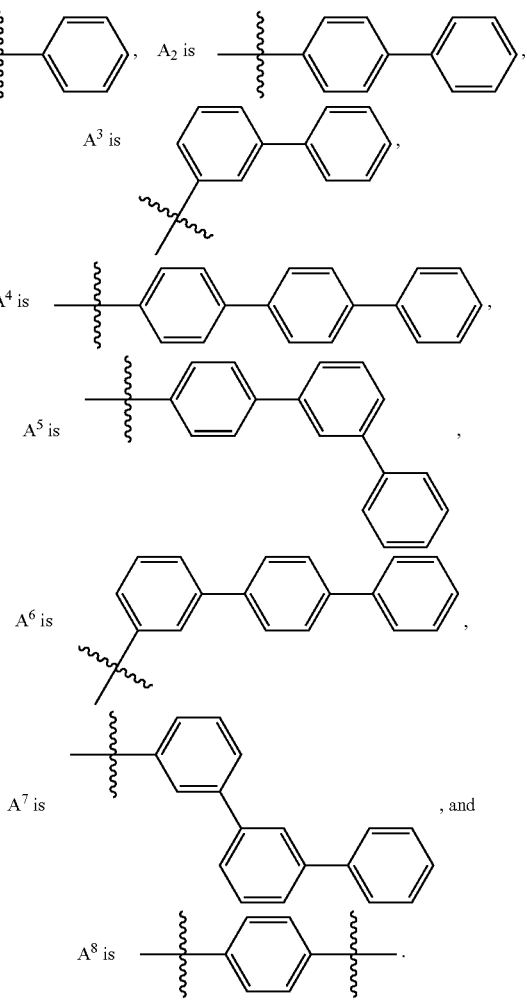

In one embodiment, the compound consists of a compound having the formula:

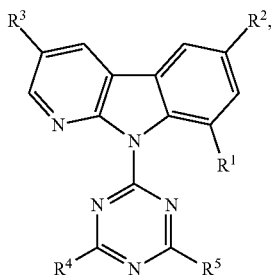

Formula III wherein the compound is selected from the group consisting of Compound 603 through Compound 686 listed in the table below, wherein $R^1$, $R^2$, $R^3$, $R^4$, and $R^5$ are as defined and wherein H is hydrogen, $A^1$ is

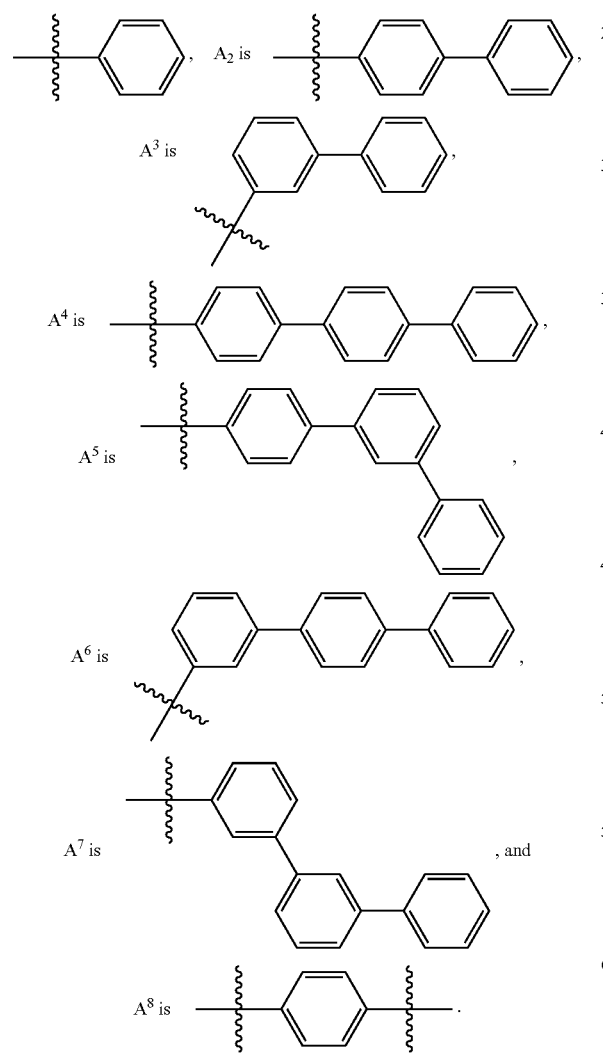

In one embodiment, the compound consists of a compound having the formula:

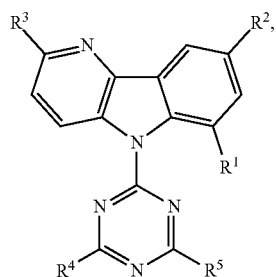

Formula IV wherein the compound is selected from the group consisting of Compound 687 through Compound 770 listed in the table below, wherein $R^1$, $R^2$, $R^3$, $R^4$, and $R^5$ are as defined and wherein H is hydrogen, $A^1$ is

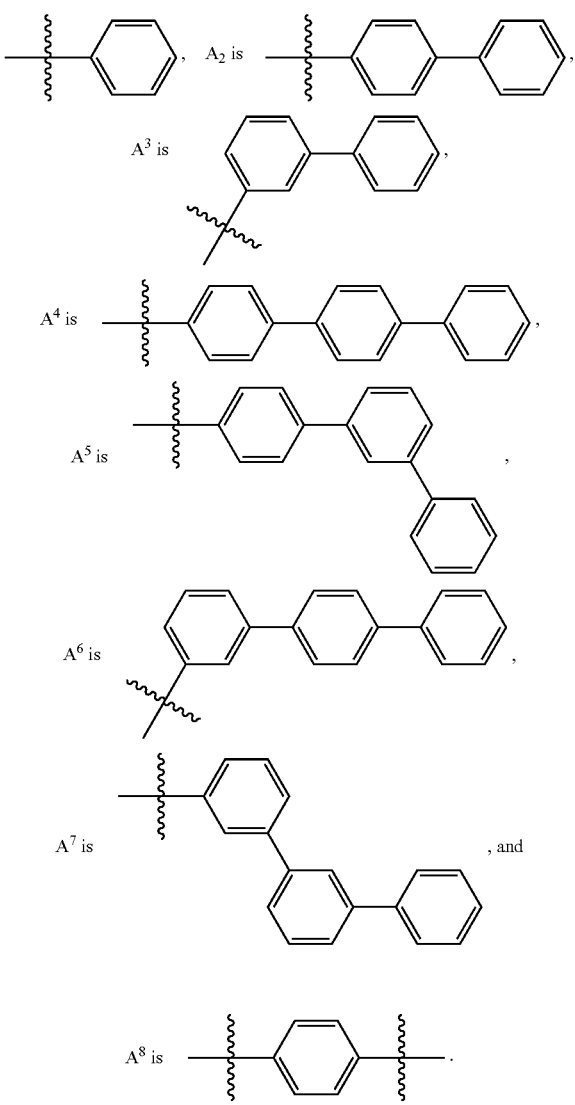

In one embodiment, the compound consists of a compound having the formula:

Formula V

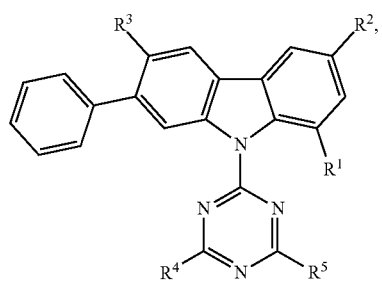

wherein the compound is selected from the group consisting of Compound 771 through Compound 854 listed in the table below, wherein $R^1$, $R^2$, $R^3$, $R^4$, and $R^5$ are as defined and wherein H is hydrogen, $A^1$ is

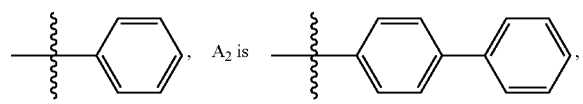

$A^3$ is 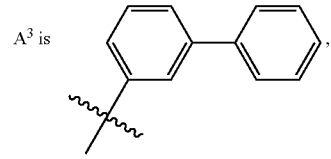, $A^4$ is 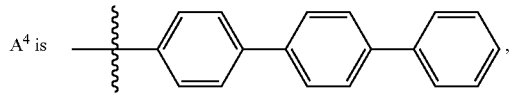, $A^5$ is 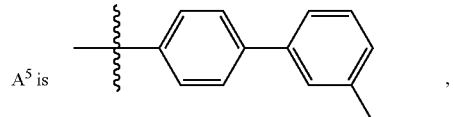, $A^6$ is 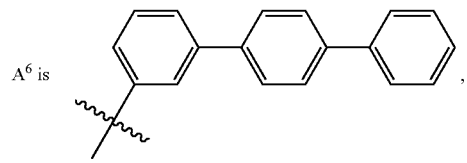, $A^7$ is 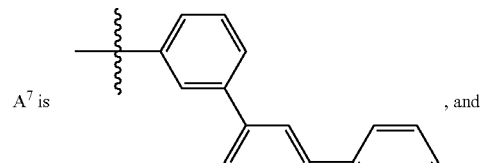, and $A^8$ is 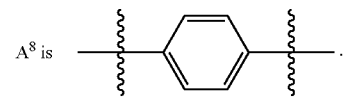.

In one embodiment, the compound consists of a compound having the formula:

Formula VI

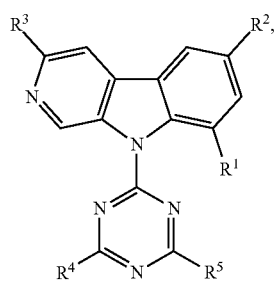

wherein the compound is selected from the group consisting of Compound 855 through Compound 938 listed in the table below, wherein $R^1$, $R^2$, $R^3$, $R^4$, and $R^5$ are as defined and wherein H is hydrogen, $A^1$ is

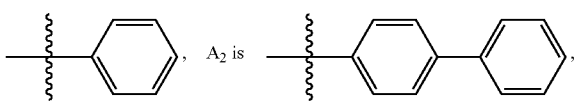

$A^3$ is 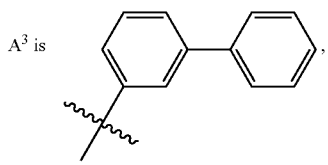, $A^4$ is 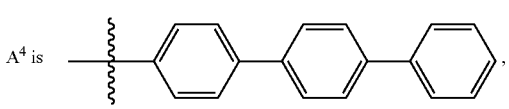, $A^5$ is 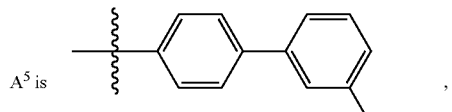, $A^6$ is 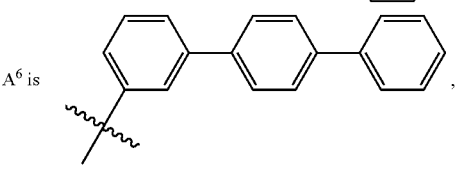, $A^7$ is 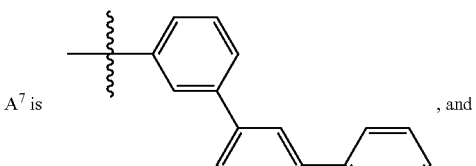, and $A^8$ is 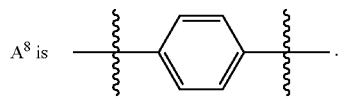.

In one embodiment, the compound is selected from the group consisting of:

Compound 2
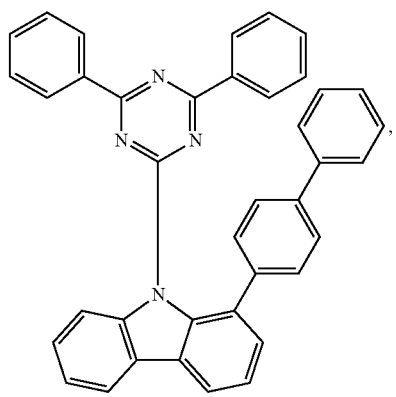
Compound 4
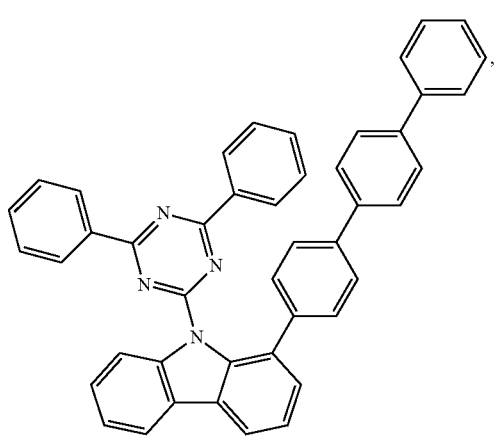
Compound 22
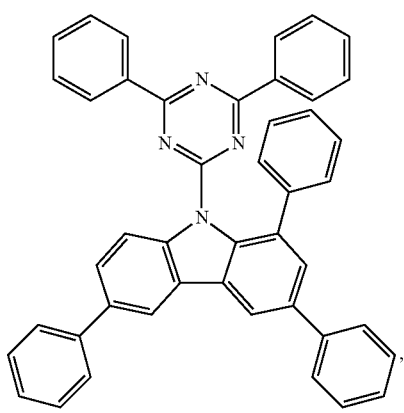
-continued
Compound 30
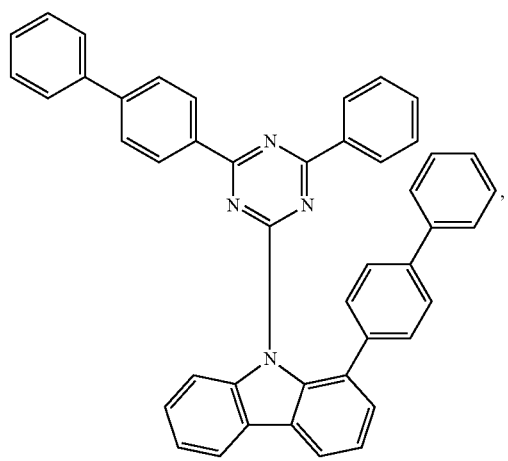
Compound 36
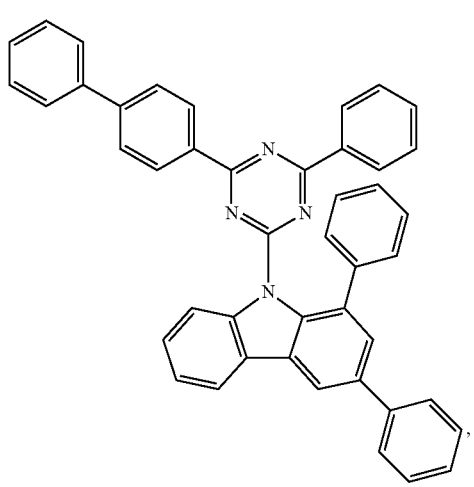
Compound 57
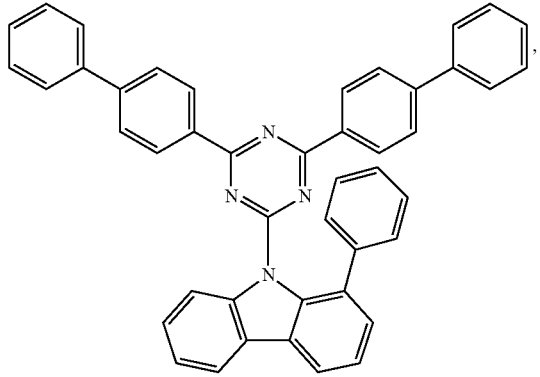

-continued

Compound 64
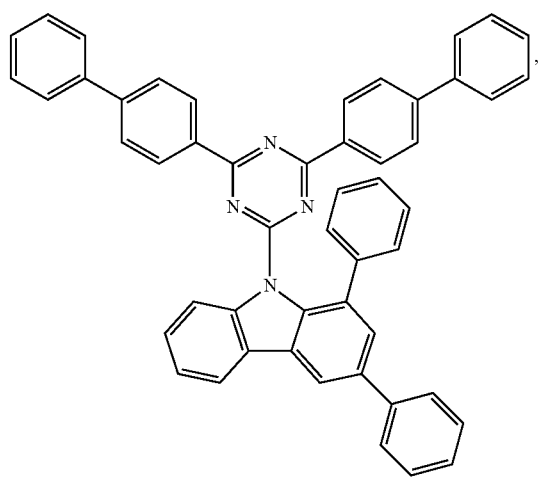

Compound 142
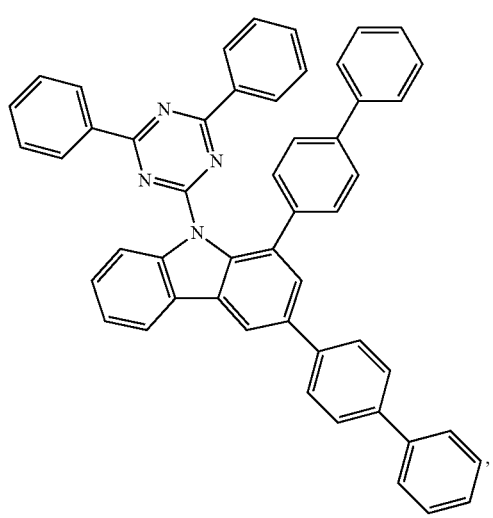

Compound 303
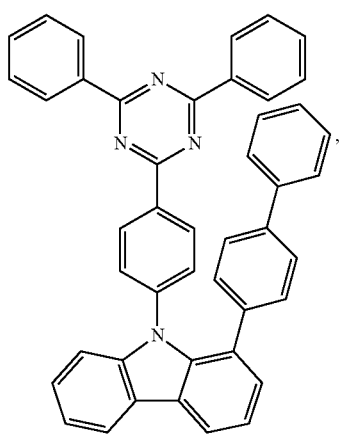

-continued

Compound 309
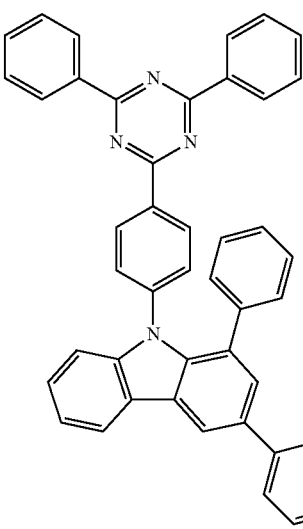, and

Compound 358
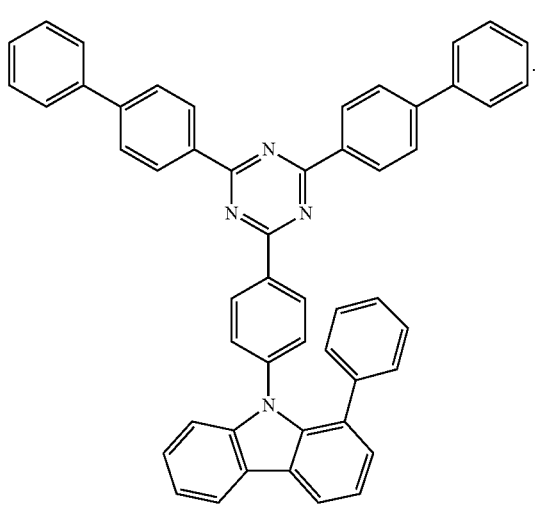

In one aspect, a formulation comprising a compound of Formula I is provided.

In one aspect, a first device comprising a first organic light emitting device, the first organic light emitting device comprising: an anode; a cathode; an organic layer, disposed between the anode and the cathode, wherein the organic layer further comprising a compound having a structure according to Formula I Formula I
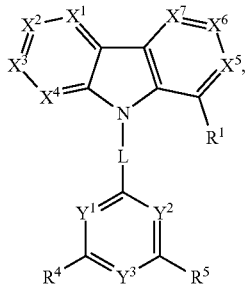

wherein $R^1$, $R^4$ and $R^5$ are independently selected from group consisting of non-fused aryl, non-fused heteroaryl, and combinations thereof; wherein L is selected from the group consisting of a bond, non-fused aryl, non-fused heteroaryl, and combinations thereof; wherein $X^1$, $X^2$, $X^3$, $X^4$, $X^5$, $X^6$, $X^7$, $Y^1$, $Y^2$, and $Y^3$ are each independently selected from the group consisting of CR and N; wherein at least two of $Y^1$, $Y^2$, and $Y^3$ are N; and wherein each R can be same or different, and is independently selected from the group consisting of hydrogen, deuterium, non-fused aryl, non-fused heteroaryl and combinations thereof, is provided.

In one embodiment, $R^1$ is selected from the group consisting of phenyl, biphenyl, terphenyl, tetraphenyl, pentaphenyl, pyridine, phenyl pyridine and pyridyl phenyl. In one embodiment, L is selected from the group consisting of phenyl, pyridyl, biphenyl, terphenyl and a bond. In one embodiment, $R^4$ is selected from the group consisting of phenyl, pyridyl, biphenyl, and terphenyl. In one embodiment, $R^5$ is selected from the group consisting of phenyl, pyridyl, biphenyl, and terphenyl. In one embodiment, the compound consists of a compound having a structure according to Formula II:

Formula II

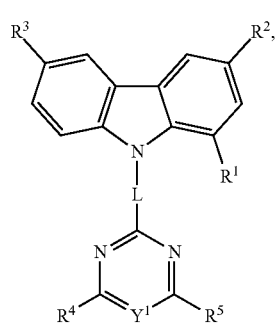

wherein $R_2$ and $R_3$ can be same or different, and independently selected from the group consisting of hydrogen, deuterium, non-fused aryl, non-fused heteroaryl and combinations thereof.

In one embodiment, the first device is an organic light-emitting device. In one embodiment, the first device comprises a lighting panel. In one embodiment, the compound is selected from the group consisting of:

Compound 2

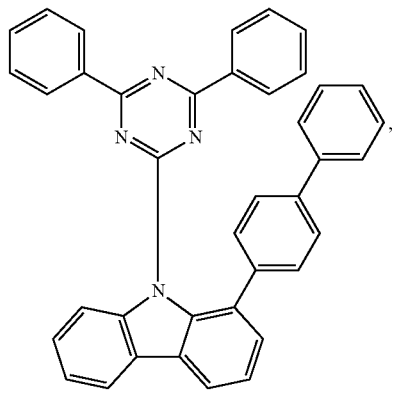

Compound 4

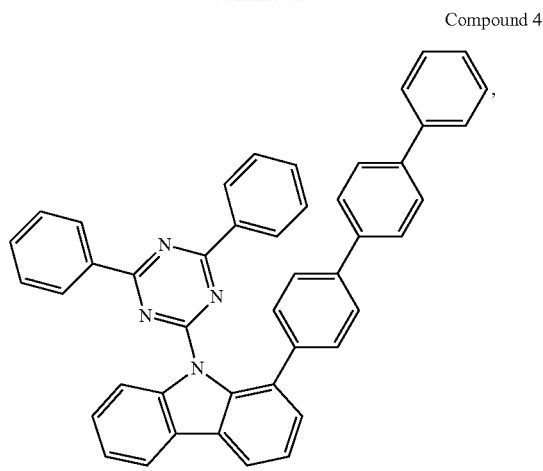

Compound 22

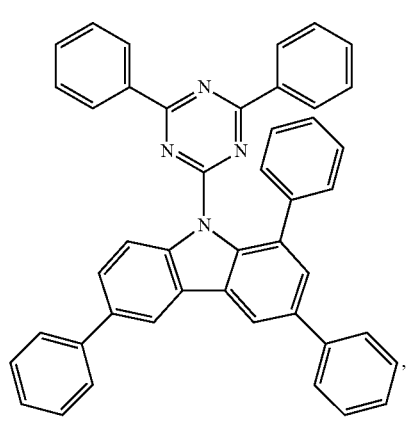

Compound 30

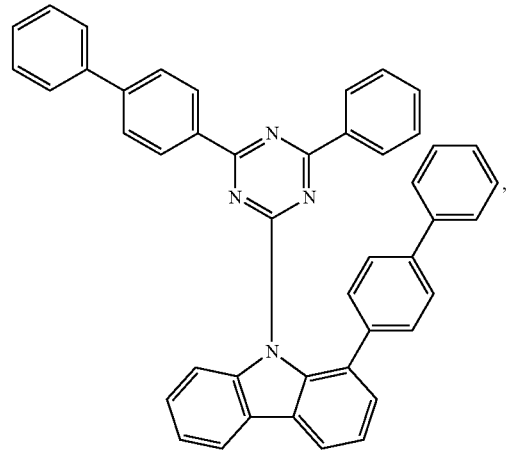

-continued
Compound 36
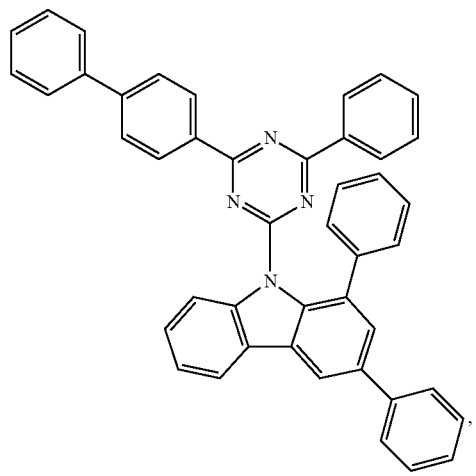
Compound 57
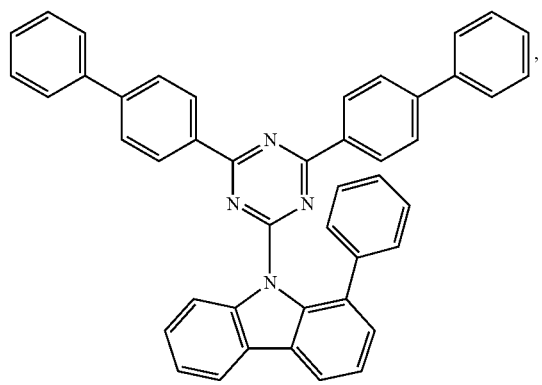
Compound 64
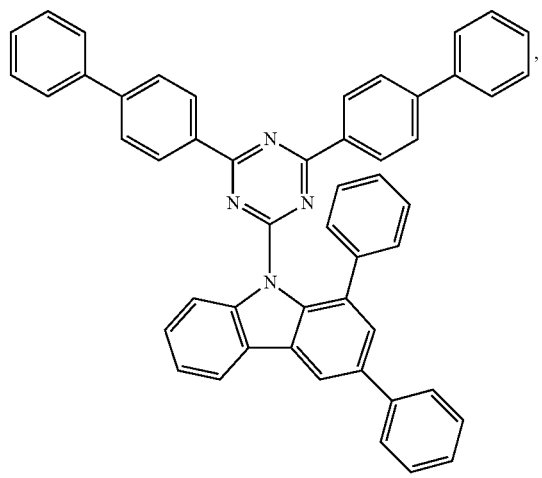
Compound 142
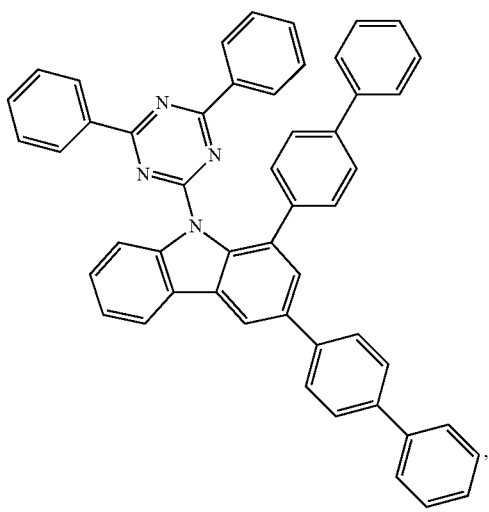
Compound 303
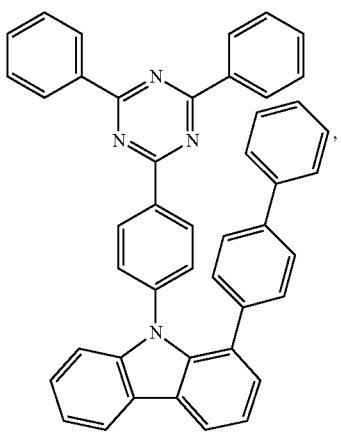
Compound 309
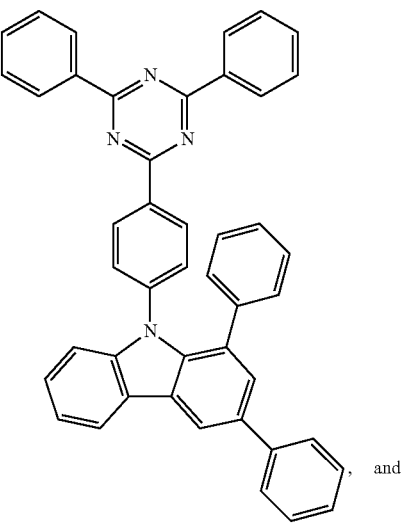
, and Compound 358

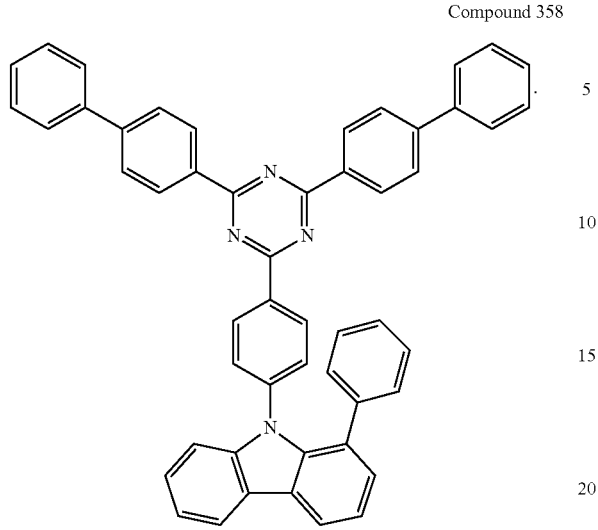

In one embodiment, the compound is selected from Compounds 1 through 602. In one embodiment, the compound is selected from Compounds 603 to 686. In one embodiment, the compound is selected from Compounds 687 to 770. In one embodiment, the compound is selected from Compounds 771 to 854. In one embodiment, the compound is selected from Compounds 855 to 938.

In one embodiment, the first device is a consumer product. In one embodiment, the organic layer is an emissive layer and the compound of Formula I is a host. In one embodiment, the organic layer is a blocking layer and the compound having Formula I is a blocking material in the organic layer. In one embodiment, the organic layer is an electron transporting layer and the compound having Formula I is an electron transporting material in the organic layer. In a further embodiment, the compound comprising a first dopant material that is an emissive dopant comprising a transition metal complex having at least one ligand or part of the ligand if the ligand is more than bidentate selected from the group consisting of:

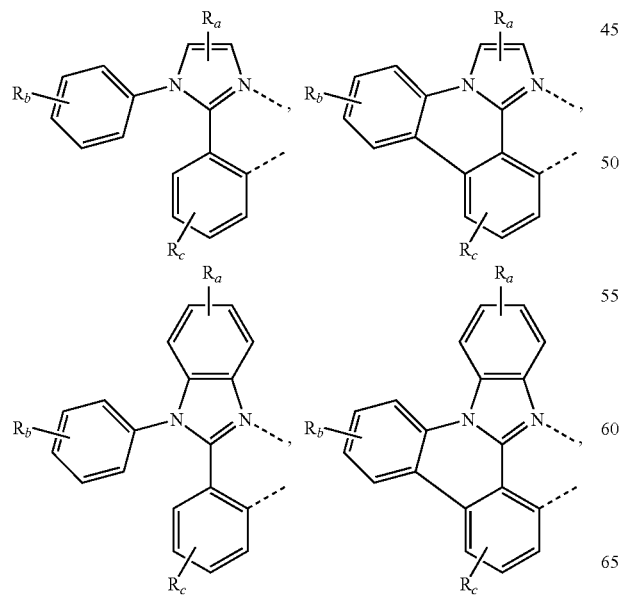

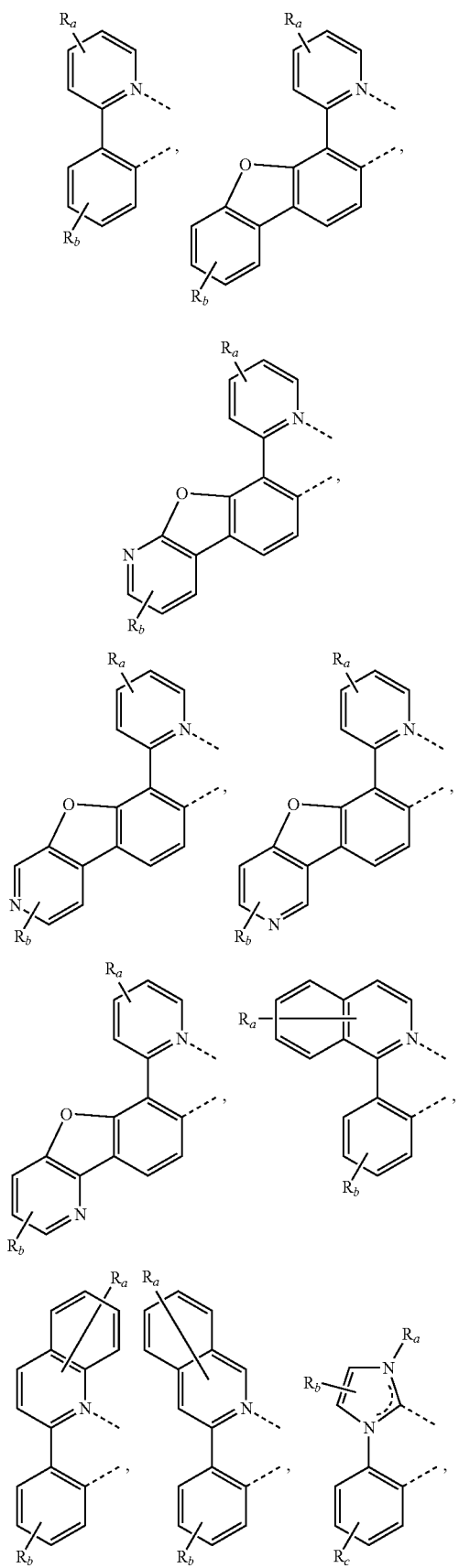

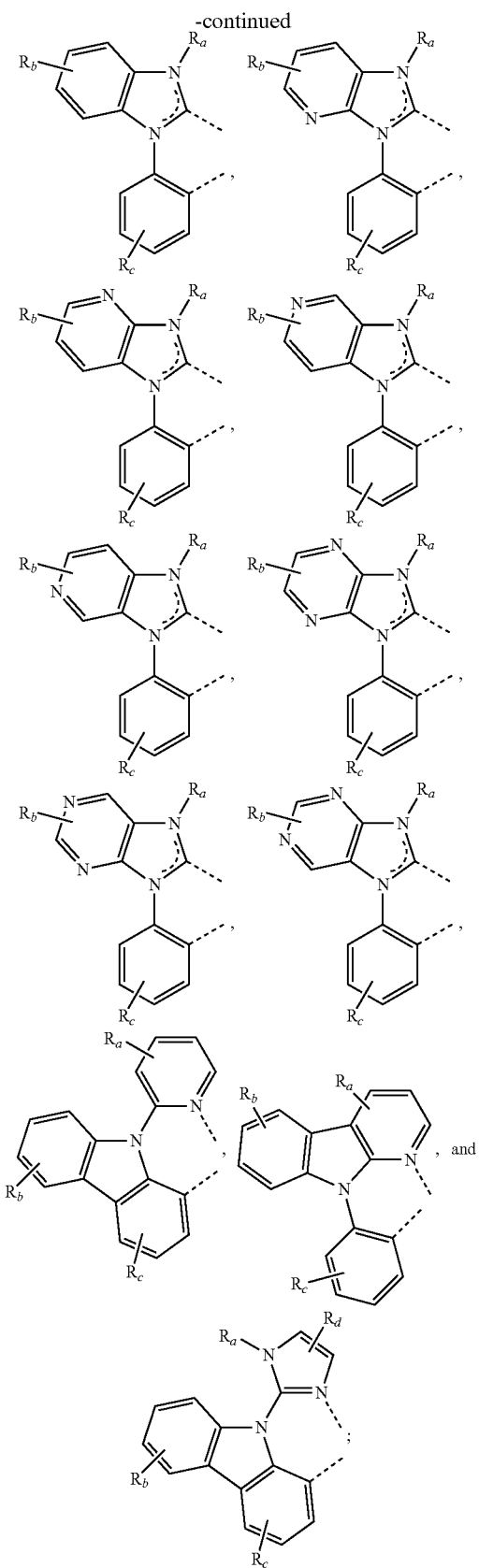

wherein $R_a$, $R_b$, and $R_c$ may represent mono, di, tri or tetra substitutions; $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and two adjacent substituents of $R_a$, $R_b$, and $R_c$ are optionally joined to form a fused ring or form a multidentate ligand.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton", which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
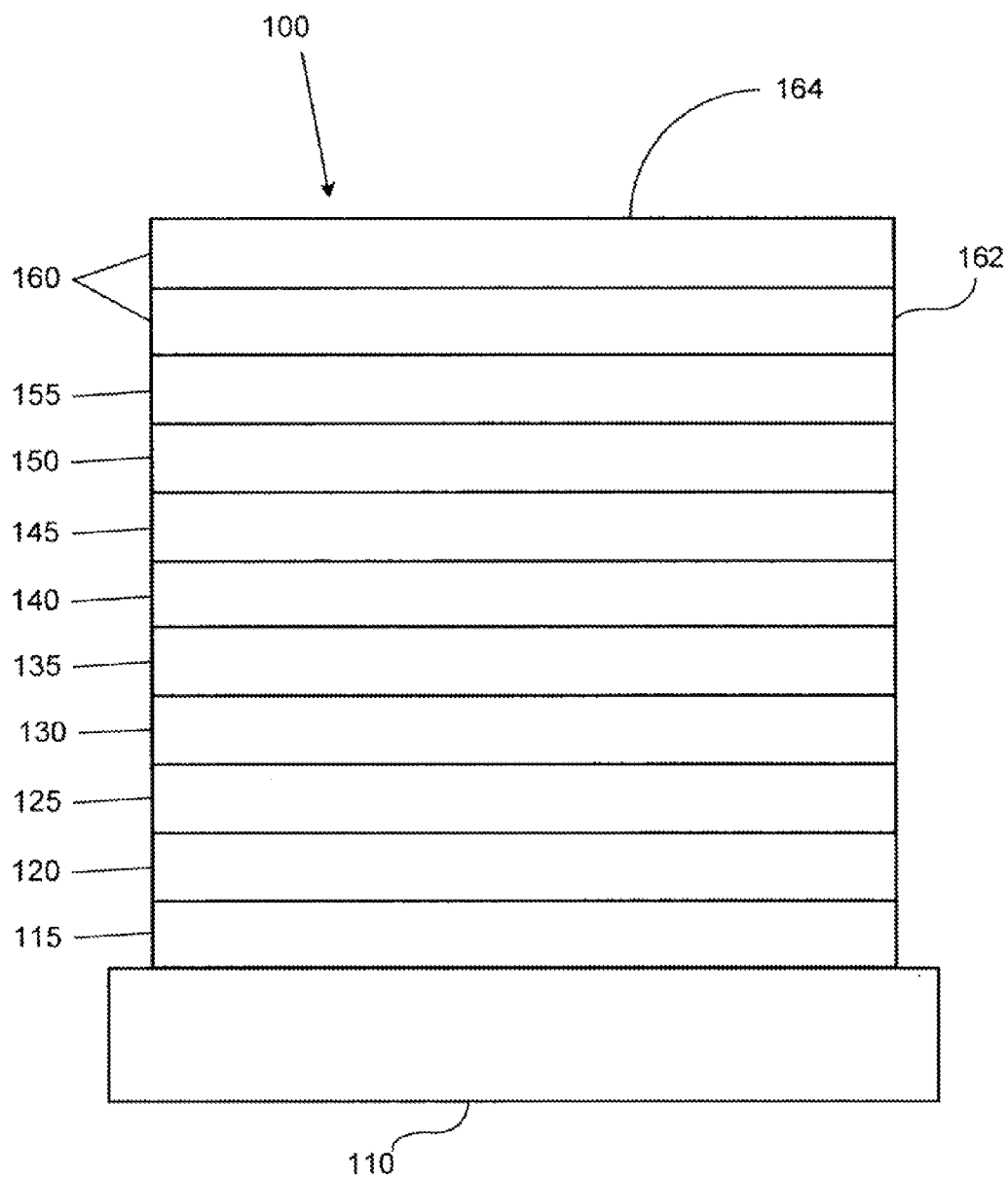
FIG. 1 shows an organic light-emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
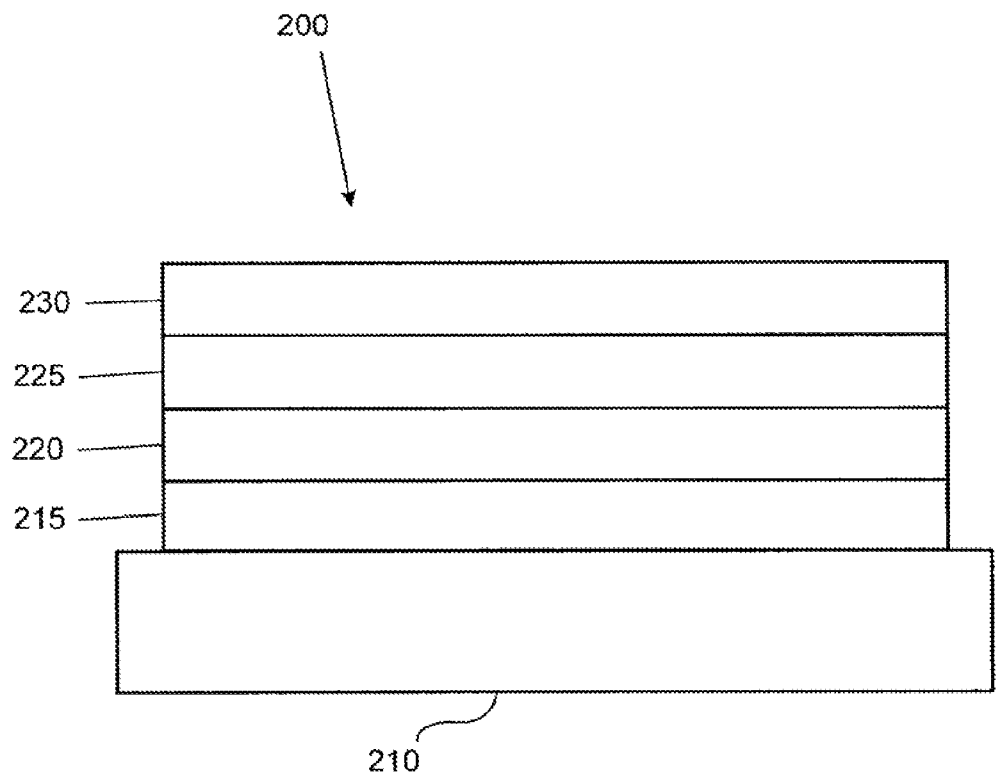
FIG. 2 shows an inverted organic light-emitting device that does not have a separate electron transport layer.
Figure 3:
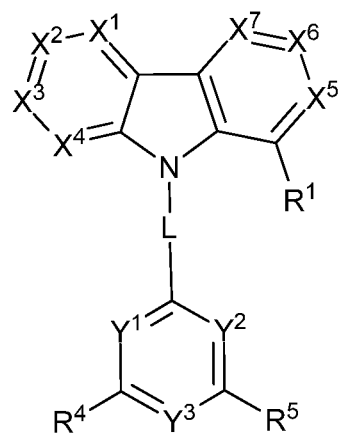
FIG. 3 shows Formula I and Formula II as disclosed herein.
Figure 3:
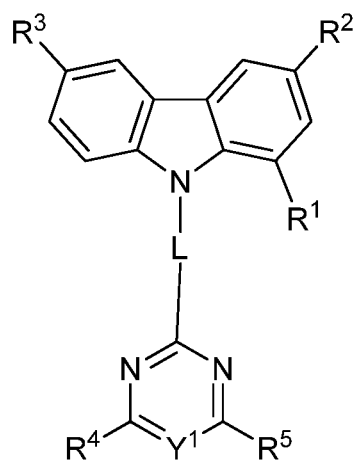

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

According to an aspect of the present disclosure, a compound having a structure according to Formula I:

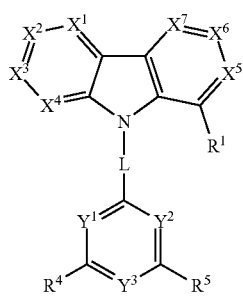

Formula I wherein $R^1$, $R^4$ and $R^5$ are independently selected from group consisting of non-fused aryl, non-fused heteroaryl, and combinations thereof; wherein L is selected from the group consisting of a bond, non-fused aryl, non-fused heteroaryl, and combinations thereof; wherein $X^1$, $X^2$, $X^3$, $X^4$, $X^5$, $X^6$, $X^7$, $Y^1$, $Y^2$, and $Y^3$ are each independently selected from the group consisting of CR and N; wherein at least two of $Y^1$, $Y^2$, and $Y^3$ are N; and wherein each R can be same or different, and is independently selected from the group consisting of hydrogen, deuterium, non-fused aryl, non-fused heteroaryl and combinations thereof, is provided.

In one embodiment, $R^1$ is selected from the group consisting of phenyl, biphenyl, terphenyl, tetraphenyl, pentaphenyl, pyridine, phenyl pyridine and pyridyl phenyl. In one embodiment, the compound of the claim 1, wherein L is selected from the group consisting of phenyl, pyridyl, biphenyl, terphenyl and a bond. In one embodiment, $R^4$ is selected from the group consisting of phenyl, pyridyl, biphenyl, and terphenyl. In one embodiment, $R^5$ is selected from the group consisting of phenyl, pyridyl, biphenyl, and terphenyl.

In one aspect, the compound consists of a compound having a structure according to Formula II:

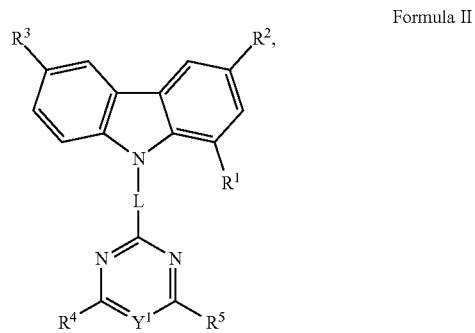

Formula II wherein $R_2$ and $R_3$ can be same or different, and independently selected from the group consisting of hydrogen, deuterium, non-fused aryl, non-fused heteroaryl and combinations thereof.

In one embodiment, the compound having a structure according to Formula II is selected from the group consisting of Compound 1 through Compound 602 listed in the table below (Table 1), wherein $Y^1$, $R^1$, $R^2$, $R^3$, $R^4$, $R^5$ and L are as defined and wherein C is Carbon, N is nitrogen, H is hydrogen, $A^1$ is

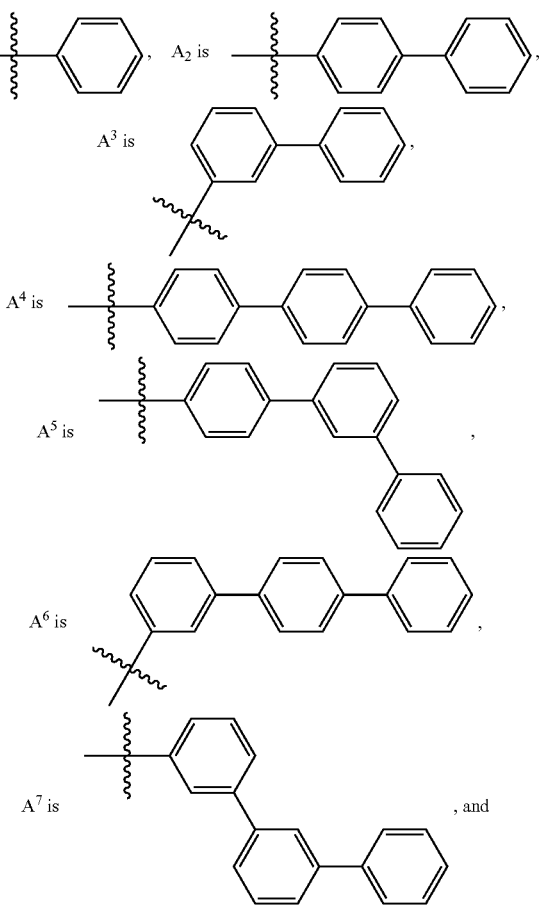

$A^8$ is 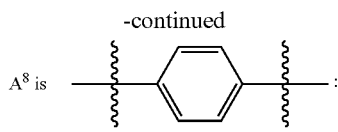:

TABLE 1

| Cmpd | $Y^1$ | $R^1$ | $R^2$ | $R^3$ | $R^4$ | $R^5$ | L |
|---|---|---|---|---|---|---|---|
| 1 | N | $A^1$ | H | H | $A^1$ | $A^1$ | Bond |
| 2 | N | $A^2$ | H | H | $A^1$ | $A^1$ | Bond |
| 3 | N | $A^3$ | H | H | $A^1$ | $A^1$ | Bond |
| 4 | N | $A^4$ | H | H | $A^1$ | $A^1$ | Bond |
| 5 | N | $A^5$ | H | H | $A^1$ | $A^1$ | Bond |
| 6 | N | $A^6$ | H | H | $A^1$ | $A^1$ | Bond |
| 7 | N | $A^7$ | H | H | $A^1$ | $A^1$ | Bond |
| 8 | N | $A^1$ | $A^1$ | H | $A^1$ | $A^1$ | Bond |
| 9 | N | $A^2$ | $A^1$ | H | $A^1$ | $A^1$ | Bond |
| 10 | N | $A^3$ | $A^1$ | H | $A^1$ | $A^1$ | Bond |
| 11 | N | $A^4$ | $A^1$ | H | $A^1$ | $A^1$ | Bond |
| 12 | N | $A^5$ | $A^1$ | H | $A^1$ | $A^1$ | Bond |
| 13 | N | $A^6$ | $A^1$ | H | $A^1$ | $A^1$ | Bond |
| 14 | N | $A^7$ | $A^1$ | H | $A^1$ | $A^1$ | Bond |
| 15 | N | $A^1$ | H | $A^1$ | $A^1$ | $A^1$ | Bond |
| 16 | N | $A^2$ | H | $A^1$ | $A^1$ | $A^1$ | Bond |
| 17 | N | $A^3$ | H | $A^1$ | $A^1$ | $A^1$ | Bond |
| 18 | N | $A^4$ | H | $A^1$ | $A^1$ | $A^1$ | Bond |
| 19 | N | $A^5$ | H | $A^1$ | $A^1$ | $A^1$ | Bond |
| 20 | N | $A^6$ | H | $A^1$ | $A^1$ | $A^1$ | Bond |
| 21 | N | $A^7$ | H | $A^1$ | $A^1$ | $A^1$ | Bond |
| 22 | N | $A^1$ | $A^1$ | $A^1$ | $A^1$ | $A^1$ | Bond |
| 23 | N | $A^2$ | $A^1$ | $A^1$ | $A^1$ | $A^1$ | Bond |
| 24 | N | $A^3$ | $A^1$ | $A^1$ | $A^1$ | $A^1$ | Bond |
| 25 | N | $A^4$ | $A^1$ | $A^1$ | $A^1$ | $A^1$ | Bond |
| 26 | N | $A^5$ | $A^1$ | $A^1$ | $A^1$ | $A^1$ | Bond |
| 27 | N | $A^6$ | $A^1$ | $A^1$ | $A^1$ | $A^1$ | Bond |
| 28 | N | $A^7$ | $A^1$ | $A^1$ | $A^1$ | $A^1$ | Bond |
| 29 | N | $A^1$ | H | H | $A^2$ | $A^1$ | Bond |
| 30 | N | $A^2$ | H | H | $A^2$ | $A^1$ | Bond |
| 31 | N | $A^3$ | H | H | $A^2$ | $A^1$ | Bond |
| 32 | N | $A^4$ | H | H | $A^2$ | $A^1$ | Bond |
| 33 | N | $A^5$ | H | H | $A^2$ | $A^1$ | Bond |
| 34 | N | $A^6$ | H | H | $A^2$ | $A^1$ | Bond |
| 35 | N | $A^7$ | H | H | $A^2$ | $A^1$ | Bond |
| 36 | N | $A^1$ | $A^1$ | H | $A^2$ | $A^1$ | Bond |
| 37 | N | $A^2$ | $A^1$ | H | $A^2$ | $A^1$ | Bond |
| 38 | N | $A^3$ | $A^1$ | H | $A^2$ | $A^1$ | Bond |
| 39 | N | $A^4$ | $A^1$ | H | $A^2$ | $A^1$ | Bond |
| 40 | N | $A^5$ | $A^1$ | H | $A^2$ | $A^1$ | Bond |
| 41 | N | $A^6$ | $A^1$ | H | $A^2$ | $A^1$ | Bond |
| 42 | N | $A^7$ | $A^1$ | H | $A^2$ | $A^1$ | Bond |
| 43 | N | $A^1$ | H | $A^1$ | $A^2$ | $A^1$ | Bond |
| 44 | N | $A^2$ | H | $A^1$ | $A^2$ | $A^1$ | Bond |
| 45 | N | $A^3$ | H | $A^1$ | $A^2$ | $A^1$ | Bond |
| 46 | N | $A^4$ | H | $A^1$ | $A^2$ | $A^1$ | Bond |
| 47 | N | $A^5$ | H | $A^1$ | $A^2$ | $A^1$ | Bond |
| 48 | N | $A^6$ | H | $A^1$ | $A^2$ | $A^1$ | Bond |
| 49 | N | $A^7$ | H | $A^1$ | $A^2$ | $A^1$ | Bond |
| 50 | N | $A^1$ | $A^1$ | $A^1$ | $A^2$ | $A^1$ | Bond |
| 51 | N | $A^2$ | $A^1$ | $A^1$ | $A^2$ | $A^1$ | Bond |
| 52 | N | $A^3$ | $A^1$ | $A^1$ | $A^2$ | $A^1$ | Bond |
| 53 | N | $A^4$ | $A^1$ | $A^1$ | $A^2$ | $A^1$ | Bond |
| 54 | N | $A^5$ | $A^1$ | $A^1$ | $A^2$ | $A^1$ | Bond |
| 55 | N | $A^6$ | $A^1$ | $A^1$ | $A^2$ | $A^1$ | Bond |
| 56 | N | $A^7$ | $A^1$ | $A^1$ | $A^2$ | $A^1$ | Bond |
| 57 | N | $A^1$ | H | H | $A^2$ | $A^2$ | Bond |
| 58 | N | $A^2$ | H | H | $A^2$ | $A^2$ | Bond |
| 59 | N | $A^3$ | H | H | $A^2$ | $A^2$ | Bond |
| 60 | N | $A^4$ | H | H | $A^2$ | $A^2$ | Bond |
| 61 | N | $A^5$ | H | H | $A^2$ | $A^2$ | Bond |
| 62 | N | $A^6$ | H | H | $A^2$ | $A^2$ | Bond |
| 63 | N | $A^7$ | H | H | $A^2$ | $A^2$ | Bond |
| 64 | N | $A^1$ | $A^1$ | H | $A^2$ | $A^2$ | Bond |
| 65 | N | $A^2$ | $A^1$ | H | $A^2$ | $A^2$ | Bond |
| 66 | N | $A^3$ | $A^1$ | H | $A^2$ | $A^2$ | Bond |
| 67 | N | $A^4$ | $A^1$ | H | $A^2$ | $A^2$ | Bond |
| 68 | N | $A^5$ | $A^1$ | H | $A^2$ | $A^2$ | Bond |
| 69 | N | $A^6$ | $A^1$ | H | $A^2$ | $A^2$ | Bond |
| 70 | N | $A^7$ | $A^1$ | H | $A^2$ | $A^2$ | Bond |
| 71 | N | $A^1$ | H | $A^1$ | $A^2$ | $A^2$ | Bond |
| 72 | N | $A^2$ | H | $A^1$ | $A^2$ | $A^2$ | Bond |
| 73 | N | $A^3$ | H | $A^1$ | $A^2$ | $A^2$ | Bond |
| 74 | N | $A^4$ | H | $A^1$ | $A^2$ | $A^2$ | Bond |
| 75 | N | $A^5$ | H | $A^1$ | $A^2$ | $A^2$ | Bond |
| 76 | N | $A^6$ | H | $A^1$ | $A^2$ | $A^2$ | Bond |
| 77 | N | $A^7$ | H | $A^1$ | $A^2$ | $A^2$ | Bond |
| 78 | N | $A^1$ | $A^1$ | $A^1$ | $A^2$ | $A^2$ | Bond |
| 79 | N | $A^2$ | $A^1$ | $A^1$ | $A^2$ | $A^2$ | Bond |
| 80 | N | $A^3$ | $A^1$ | $A^1$ | $A^2$ | $A^2$ | Bond |
| 81 | N | $A^4$ | $A^1$ | $A^1$ | $A^2$ | $A^2$ | Bond |
| 82 | N | $A^5$ | $A^1$ | $A^1$ | $A^2$ | $A^2$ | Bond |
| 83 | N | $A^6$ | $A^1$ | $A^1$ | $A^2$ | $A^2$ | Bond |
| 84 | N | $A^7$ | $A^1$ | $A^1$ | $A^2$ | $A^2$ | Bond |
| 85 | N | $A^1$ | H | H | $A^3$ | $A^1$ | Bond |
| 86 | N | $A^2$ | H | H | $A^3$ | $A^1$ | Bond |
| 87 | N | $A^3$ | H | H | $A^3$ | $A^1$ | Bond |
| 88 | N | $A^4$ | H | H | $A^3$ | $A^1$ | Bond |
| 89 | N | $A^5$ | H | H | $A^3$ | $A^1$ | Bond |
| 90 | N | $A^6$ | H | H | $A^3$ | $A^1$ | Bond |
| 91 | N | $A^7$ | H | H | $A^3$ | $A^1$ | Bond |
| 92 | N | $A^1$ | $A^1$ | H | $A^3$ | $A^1$ | Bond |
| 93 | N | $A^2$ | $A^1$ | H | $A^3$ | $A^1$ | Bond |
| 94 | N | $A^3$ | $A^1$ | H | $A^3$ | $A^1$ | Bond |
| 95 | N | $A^4$ | $A^1$ | H | $A^3$ | $A^1$ | Bond |
| 96 | N | $A^5$ | $A^1$ | H | $A^3$ | $A^1$ | Bond |
| 97 | N | $A^6$ | $A^1$ | H | $A^3$ | $A^1$ | Bond |
| 98 | N | $A^7$ | $A^1$ | H | $A^3$ | $A^1$ | Bond |
| 99 | N | $A^1$ | H | $A^1$ | $A^3$ | $A^1$ | Bond |
| 100 | N | $A^2$ | H | $A^1$ | $A^3$ | $A^1$ | Bond |
| 101 | N | $A^3$ | H | $A^1$ | $A^3$ | $A^1$ | Bond |
| 102 | N | $A^4$ | H | $A^1$ | $A^3$ | $A^1$ | Bond |
| 103 | N | $A^5$ | H | $A^1$ | $A^3$ | $A^1$ | Bond |
| 104 | N | $A^6$ | H | $A^1$ | $A^3$ | $A^1$ | Bond |
| 105 | N | $A^7$ | H | $A^1$ | $A^3$ | $A^1$ | Bond |
| 106 | N | $A^1$ | $A^1$ | $A^1$ | $A^3$ | $A^1$ | Bond |
| 107 | N | $A^2$ | $A^1$ | $A^1$ | $A^3$ | $A^1$ | Bond |
| 108 | N | $A^3$ | $A^1$ | $A^1$ | $A^3$ | $A^1$ | Bond |
| 109 | N | $A^4$ | $A^1$ | $A^1$ | $A^3$ | $A^1$ | Bond |
| 110 | N | $A^5$ | $A^1$ | $A^1$ | $A^3$ | $A^1$ | Bond |
| 111 | N | $A^6$ | $A^1$ | $A^1$ | $A^3$ | $A^1$ | Bond |
| 112 | N | $A^7$ | $A^1$ | $A^1$ | $A^3$ | $A^1$ | Bond |
| 113 | N | $A^1$ | H | H | $A^3$ | $A^3$ | Bond |
| 114 | N | $A^2$ | H | H | $A^3$ | $A^3$ | Bond |
| 115 | N | $A^3$ | H | H | $A^3$ | $A^3$ | Bond |
| 116 | N | $A^4$ | H | H | $A^3$ | $A^3$ | Bond |
| 117 | N | $A^5$ | H | H | $A^3$ | $A^3$ | Bond |
| 118 | N | $A^6$ | H | H | $A^3$ | $A^3$ | Bond |
| 119 | N | $A^7$ | H | H | $A^3$ | $A^3$ | Bond |
| 120 | N | $A^1$ | $A^1$ | H | $A^3$ | $A^3$ | Bond |
| 121 | N | $A^2$ | $A^1$ | H | $A^3$ | $A^3$ | Bond |
| 122 | N | $A^3$ | $A^1$ | H | $A^3$ | $A^3$ | Bond |
| 123 | N | $A^4$ | $A^1$ | H | $A^3$ | $A^3$ | Bond |
| 124 | N | $A^5$ | $A^1$ | H | $A^3$ | $A^3$ | Bond |
| 125 | N | $A^6$ | $A^1$ | H | $A^3$ | $A^3$ | Bond |
| 126 | N | $A^7$ | $A^1$ | H | $A^3$ | $A^3$ | Bond |
| 127 | N | $A^1$ | H | $A^1$ | $A^3$ | $A^3$ | Bond |
| 128 | N | $A^2$ | H | $A^1$ | $A^3$ | $A^3$ | Bond |
| 129 | N | $A^3$ | H | $A^1$ | $A^3$ | $A^3$ | Bond |
| 130 | N | $A^4$ | H | $A^1$ | $A^3$ | $A^3$ | Bond |
| 131 | N | $A^5$ | H | $A^1$ | $A^3$ | $A^3$ | Bond |
| 132 | N | $A^6$ | H | $A^1$ | $A^3$ | $A^3$ | Bond |
| 133 | N | $A^7$ | H | $A^1$ | $A^3$ | $A^3$ | Bond |
| 134 | N | $A^1$ | $A^1$ | $A^1$ | $A^3$ | $A^3$ | Bond |
| 135 | N | $A^2$ | $A^1$ | $A^1$ | $A^3$ | $A^3$ | Bond |
| 136 | N | $A^3$ | $A^1$ | $A^1$ | $A^3$ | $A^3$ | Bond |
| 137 | N | $A^4$ | $A^1$ | $A^1$ | $A^3$ | $A^3$ | Bond |
| 138 | N | $A^5$ | $A^1$ | $A^1$ | $A^3$ | $A^3$ | Bond |
| 139 | N | $A^6$ | $A^1$ | $A^1$ | $A^3$ | $A^3$ | Bond |
| 140 | N | $A^7$ | $A^1$ | $A^1$ | $A^3$ | $A^3$ | Bond |
| 141 | N | $A^1$ | $A^2$ | H | $A^1$ | $A^1$ | Bond |
| 142 | N | $A^2$ | $A^2$ | H | $A^1$ | $A^1$ | Bond |
| 143 | N | $A^3$ | $A^2$ | H | $A^1$ | $A^1$ | Bond |
| 144 | N | $A^4$ | $A^2$ | H | $A^1$ | $A^1$ | Bond |
| 145 | N | $A^5$ | $A^2$ | H | $A^1$ | $A^1$ | Bond |
| 146 | N | $A^6$ | $A^2$ | H | $A^1$ | $A^1$ | Bond |
| 147 | N | $A^7$ | $A^2$ | H | $A^1$ | $A^1$ | Bond |

TABLE 1-continued

| Cmpd | Y$^1$ | R$^1$ | R$^2$ | R$^3$ | R$^4$ | R$^5$ | L |
|---|---|---|---|---|---|---|---|
| 148 | N | A$^1$ | A$^2$ | H | A$^2$ | A$^1$ | Bond |
| 149 | N | A$^2$ | A$^2$ | H | A$^2$ | A$^1$ | Bond |
| 150 | N | A$^3$ | A$^2$ | H | A$^2$ | A$^1$ | Bond |
| 151 | N | A$^4$ | A$^2$ | H | A$^2$ | A$^1$ | Bond |
| 152 | N | A$^5$ | A$^2$ | H | A$^2$ | A$^1$ | Bond |
| 153 | N | A$^6$ | A$^2$ | H | A$^2$ | A$^1$ | Bond |
| 154 | N | A$^7$ | A$^2$ | H | A$^2$ | A$^1$ | Bond |
| 155 | N | A$^1$ | A$^2$ | H | A$^2$ | A$^2$ | Bond |
| 156 | N | A$^2$ | A$^2$ | H | A$^2$ | A$^2$ | Bond |
| 157 | N | A$^3$ | A$^2$ | H | A$^2$ | A$^2$ | Bond |
| 158 | N | A$^4$ | A$^2$ | H | A$^2$ | A$^2$ | Bond |
| 159 | N | A$^5$ | A$^2$ | H | A$^2$ | A$^2$ | Bond |
| 160 | N | A$^6$ | A$^2$ | H | A$^2$ | A$^2$ | Bond |
| 161 | N | A$^7$ | A$^2$ | H | A$^2$ | A$^2$ | Bond |
| 162 | C | A$^1$ | H | H | A$^1$ | A$^1$ | Bond |
| 163 | C | A$^2$ | H | H | A$^1$ | A$^1$ | Bond |
| 164 | C | A$^3$ | H | H | A$^1$ | A$^1$ | Bond |
| 165 | C | A$^4$ | H | H | A$^1$ | A$^1$ | Bond |
| 166 | C | A$^5$ | H | H | A$^1$ | A$^1$ | Bond |
| 167 | C | A$^6$ | H | H | A$^1$ | A$^1$ | Bond |
| 168 | C | A$^7$ | H | H | A$^1$ | A$^1$ | Bond |
| 169 | C | A$^1$ | A$^1$ | H | A$^1$ | A$^1$ | Bond |
| 170 | C | A$^2$ | A$^1$ | H | A$^1$ | A$^1$ | Bond |
| 171 | C | A$^3$ | A$^1$ | H | A$^1$ | A$^1$ | Bond |
| 172 | C | A$^4$ | A$^1$ | H | A$^1$ | A$^1$ | Bond |
| 173 | C | A$^5$ | A$^1$ | H | A$^1$ | A$^1$ | Bond |
| 174 | C | A$^6$ | A$^1$ | H | A$^1$ | A$^1$ | Bond |
| 175 | C | A$^7$ | A$^1$ | H | A$^1$ | A$^1$ | Bond |
| 176 | C | A$^1$ | H | A$^1$ | A$^1$ | A$^1$ | Bond |
| 177 | C | A$^2$ | H | A$^1$ | A$^1$ | A$^1$ | Bond |
| 178 | C | A$^3$ | H | A$^1$ | A$^1$ | A$^1$ | Bond |
| 179 | C | A$^4$ | H | A$^1$ | A$^1$ | A$^1$ | Bond |
| 180 | C | A$^5$ | H | A$^1$ | A$^1$ | A$^1$ | Bond |
| 181 | C | A$^6$ | H | A$^1$ | A$^1$ | A$^1$ | Bond |
| 182 | C | A$^7$ | H | A$^1$ | A$^1$ | A$^1$ | Bond |
| 183 | C | A$^1$ | A$^1$ | A$^1$ | A$^1$ | A$^1$ | Bond |
| 184 | C | A$^2$ | A$^1$ | A$^1$ | A$^1$ | A$^1$ | Bond |
| 185 | C | A$^3$ | A$^1$ | A$^1$ | A$^1$ | A$^1$ | Bond |
| 186 | C | A$^4$ | A$^1$ | A$^1$ | A$^1$ | A$^1$ | Bond |
| 187 | C | A$^5$ | A$^1$ | A$^1$ | A$^1$ | A$^1$ | Bond |
| 188 | C | A$^6$ | A$^1$ | A$^1$ | A$^1$ | A$^1$ | Bond |
| 189 | C | A$^7$ | A$^1$ | A$^1$ | A$^1$ | A$^1$ | Bond |
| 190 | C | A$^1$ | H | H | A$^2$ | A$^1$ | Bond |
| 191 | C | A$^2$ | H | H | A$^2$ | A$^1$ | Bond |
| 192 | C | A$^3$ | H | H | A$^2$ | A$^1$ | Bond |
| 193 | C | A$^4$ | H | H | A$^2$ | A$^1$ | Bond |
| 194 | C | A$^5$ | H | H | A$^2$ | A$^1$ | Bond |
| 195 | C | A$^6$ | H | H | A$^2$ | A$^1$ | Bond |
| 196 | C | A$^7$ | H | H | A$^2$ | A$^1$ | Bond |
| 197 | C | A$^1$ | A$^1$ | H | A$^2$ | A$^1$ | Bond |
| 198 | C | A$^2$ | A$^1$ | H | A$^2$ | A$^1$ | Bond |
| 199 | C | A$^3$ | A$^1$ | H | A$^2$ | A$^1$ | Bond |
| 200 | C | A$^4$ | A$^1$ | H | A$^2$ | A$^1$ | Bond |
| 201 | C | A$^5$ | A$^1$ | H | A$^2$ | A$^1$ | Bond |
| 202 | C | A$^6$ | A$^1$ | H | A$^2$ | A$^1$ | Bond |
| 203 | C | A$^7$ | A$^1$ | H | A$^2$ | A$^1$ | Bond |
| 204 | C | A$^1$ | H | A$^1$ | A$^2$ | A$^1$ | Bond |
| 205 | C | A$^2$ | H | A$^1$ | A$^2$ | A$^1$ | Bond |
| 206 | C | A$^3$ | H | A$^1$ | A$^2$ | A$^1$ | Bond |
| 207 | C | A$^4$ | H | A$^1$ | A$^2$ | A$^1$ | Bond |
| 208 | C | A$^5$ | H | A$^1$ | A$^2$ | A$^1$ | Bond |
| 209 | C | A$^6$ | H | A$^1$ | A$^2$ | A$^1$ | Bond |
| 210 | C | A$^7$ | H | A$^1$ | A$^2$ | A$^1$ | Bond |
| 211 | C | A$^1$ | A$^1$ | A$^1$ | A$^2$ | A$^1$ | Bond |
| 212 | C | A$^2$ | A$^1$ | A$^1$ | A$^2$ | A$^1$ | Bond |
| 213 | C | A$^3$ | A$^1$ | A$^1$ | A$^2$ | A$^1$ | Bond |
| 214 | C | A$^4$ | A$^1$ | A$^1$ | A$^2$ | A$^1$ | Bond |
| 215 | C | A$^5$ | A$^1$ | A$^1$ | A$^2$ | A$^1$ | Bond |
| 216 | C | A$^6$ | A$^1$ | A$^1$ | A$^2$ | A$^1$ | Bond |
| 217 | C | A$^7$ | A$^1$ | A$^1$ | A$^2$ | A$^1$ | Bond |
| 218 | C | A$^1$ | H | H | A$^2$ | A$^2$ | Bond |
| 219 | C | A$^2$ | H | H | A$^2$ | A$^2$ | Bond |
| 220 | C | A$^3$ | H | H | A$^2$ | A$^2$ | Bond |
| 221 | C | A$^4$ | H | H | A$^2$ | A$^2$ | Bond |
| 222 | C | A$^5$ | H | H | A$^2$ | A$^2$ | Bond |
| 223 | C | A$^6$ | H | H | A$^2$ | A$^2$ | Bond |
| 224 | C | A$^7$ | H | H | A$^2$ | A$^2$ | Bond |
| 225 | C | A$^1$ | A$^1$ | H | A$^2$ | A$^2$ | Bond |
| 226 | C | A$^2$ | A$^1$ | H | A$^2$ | A$^2$ | Bond |
| 227 | C | A$^3$ | A$^1$ | H | A$^2$ | A$^2$ | Bond |
| 228 | C | A$^4$ | A$^1$ | H | A$^2$ | A$^2$ | Bond |
| 229 | C | A$^5$ | A$^1$ | H | A$^2$ | A$^2$ | Bond |
| 230 | C | A$^6$ | A$^1$ | H | A$^2$ | A$^2$ | Bond |
| 231 | C | A$^7$ | A$^1$ | H | A$^2$ | A$^2$ | Bond |
| 232 | C | A$^1$ | H | A$^1$ | A$^2$ | A$^2$ | Bond |
| 233 | C | A$^2$ | H | A$^1$ | A$^2$ | A$^2$ | Bond |
| 234 | C | A$^3$ | H | A$^1$ | A$^2$ | A$^2$ | Bond |
| 235 | C | A$^4$ | H | A$^1$ | A$^2$ | A$^2$ | Bond |
| 236 | C | A$^5$ | H | A$^1$ | A$^2$ | A$^2$ | Bond |
| 237 | C | A$^6$ | H | A$^1$ | A$^2$ | A$^2$ | Bond |
| 238 | C | A$^7$ | H | A$^1$ | A$^2$ | A$^2$ | Bond |
| 239 | C | A$^1$ | A$^1$ | A$^1$ | A$^2$ | A$^2$ | Bond |
| 240 | C | A$^2$ | A$^1$ | A$^1$ | A$^2$ | A$^2$ | Bond |
| 241 | C | A$^3$ | A$^1$ | A$^1$ | A$^2$ | A$^2$ | Bond |
| 242 | C | A$^4$ | A$^1$ | A$^1$ | A$^2$ | A$^2$ | Bond |
| 243 | C | A$^5$ | A$^1$ | A$^1$ | A$^2$ | A$^2$ | Bond |
| 244 | C | A$^6$ | A$^1$ | A$^1$ | A$^2$ | A$^2$ | Bond |
| 245 | C | A$^7$ | A$^1$ | A$^1$ | A$^2$ | A$^2$ | Bond |
| 246 | C | A$^1$ | H | H | A$^3$ | A$^1$ | Bond |
| 247 | C | A$^2$ | H | H | A$^3$ | A$^1$ | Bond |
| 248 | C | A$^3$ | H | H | A$^3$ | A$^1$ | Bond |
| 249 | C | A$^4$ | H | H | A$^3$ | A$^1$ | Bond |
| 250 | C | A$^5$ | H | H | A$^3$ | A$^1$ | Bond |
| 251 | C | A$^6$ | H | H | A$^3$ | A$^1$ | Bond |
| 252 | C | A$^7$ | H | H | A$^3$ | A$^1$ | Bond |
| 253 | C | A$^1$ | A$^1$ | H | A$^3$ | A$^1$ | Bond |
| 254 | C | A$^2$ | A$^1$ | H | A$^3$ | A$^1$ | Bond |
| 255 | C | A$^3$ | A$^1$ | H | A$^3$ | A$^1$ | Bond |
| 256 | C | A$^4$ | A$^1$ | H | A$^3$ | A$^1$ | Bond |
| 257 | C | A$^5$ | A$^1$ | H | A$^3$ | A$^1$ | Bond |
| 258 | C | A$^6$ | A$^1$ | H | A$^3$ | A$^1$ | Bond |
| 259 | C | A$^7$ | A$^1$ | H | A$^3$ | A$^1$ | Bond |
| 260 | C | A$^1$ | H | A$^1$ | A$^3$ | A$^1$ | Bond |
| 261 | C | A$^2$ | H | A$^1$ | A$^3$ | A$^1$ | Bond |
| 262 | C | A$^3$ | H | A$^1$ | A$^3$ | A$^1$ | Bond |
| 263 | C | A$^4$ | H | A$^1$ | A$^3$ | A$^1$ | Bond |
| 264 | C | A$^5$ | H | A$^1$ | A$^3$ | A$^1$ | Bond |
| 265 | C | A$^6$ | H | A$^1$ | A$^3$ | A$^1$ | Bond |
| 266 | C | A$^7$ | H | A$^1$ | A$^3$ | A$^1$ | Bond |
| 267 | C | A$^1$ | A$^1$ | A$^1$ | A$^3$ | A$^1$ | Bond |
| 268 | C | A$^2$ | A$^1$ | A$^1$ | A$^3$ | A$^1$ | Bond |
| 269 | C | A$^3$ | A$^1$ | A$^1$ | A$^3$ | A$^1$ | Bond |
| 270 | C | A$^4$ | A$^1$ | A$^1$ | A$^3$ | A$^1$ | Bond |
| 271 | C | A$^5$ | A$^1$ | A$^1$ | A$^3$ | A$^1$ | Bond |
| 272 | C | A$^6$ | A$^1$ | A$^1$ | A$^3$ | A$^1$ | Bond |
| 273 | C | A$^7$ | A$^1$ | A$^1$ | A$^3$ | A$^1$ | Bond |
| 274 | C | A$^1$ | H | H | A$^3$ | A$^3$ | Bond |
| 275 | C | A$^2$ | H | H | A$^3$ | A$^3$ | Bond |
| 276 | C | A$^3$ | H | H | A$^3$ | A$^3$ | Bond |
| 277 | C | A$^4$ | H | H | A$^3$ | A$^3$ | Bond |
| 278 | C | A$^5$ | H | H | A$^3$ | A$^3$ | Bond |
| 279 | C | A$^6$ | H | H | A$^3$ | A$^3$ | Bond |
| 280 | C | A$^7$ | H | H | A$^3$ | A$^3$ | Bond |
| 281 | C | A$^1$ | A$^1$ | H | A$^3$ | A$^3$ | Bond |
| 282 | C | A$^2$ | A$^1$ | H | A$^3$ | A$^3$ | Bond |
| 283 | C | A$^3$ | A$^1$ | H | A$^3$ | A$^3$ | Bond |
| 284 | C | A$^4$ | A$^1$ | H | A$^3$ | A$^3$ | Bond |
| 285 | C | A$^5$ | A$^1$ | H | A$^3$ | A$^3$ | Bond |
| 286 | C | A$^6$ | A$^1$ | H | A$^3$ | A$^3$ | Bond |
| 287 | C | A$^7$ | A$^1$ | H | A$^3$ | A$^3$ | Bond |
| 288 | C | A$^1$ | H | A$^1$ | A$^3$ | A$^3$ | Bond |
| 289 | C | A$^2$ | H | A$^1$ | A$^3$ | A$^3$ | Bond |
| 290 | C | A$^3$ | H | A$^1$ | A$^3$ | A$^3$ | Bond |
| 291 | C | A$^4$ | H | A$^1$ | A$^3$ | A$^3$ | Bond |
| 292 | C | A$^5$ | H | A$^1$ | A$^3$ | A$^3$ | Bond |
| 293 | C | A$^6$ | H | A$^1$ | A$^3$ | A$^3$ | Bond |
| 294 | C | A$^7$ | H | A$^1$ | A$^3$ | A$^3$ | Bond |
| 295 | C | A$^1$ | A$^1$ | A$^1$ | A$^3$ | A$^3$ | Bond |
| 296 | C | A$^2$ | A$^1$ | A$^1$ | A$^3$ | A$^3$ | Bond |
| 297 | C | A$^3$ | A$^1$ | A$^1$ | A$^3$ | A$^3$ | Bond |
| 298 | C | A$^4$ | A$^1$ | A$^1$ | A$^3$ | A$^3$ | Bond |
| 299 | C | A$^5$ | A$^1$ | A$^1$ | A$^3$ | A$^3$ | Bond |
| 300 | C | A$^6$ | A$^1$ | A$^1$ | A$^3$ | A$^3$ | Bond |
| 301 | C | A$^7$ | A$^1$ | A$^1$ | A$^3$ | A$^3$ | Bond |
| 302 | N | A$^1$ | H | H | A$^1$ | A$^1$ | A$^8$ |
| 303 | N | A$^2$ | H | H | A$^1$ | A$^1$ | A$^8$ |

TABLE 1-continued

| Cmpd | Y$^1$ | R$^1$ | R$^2$ | R$^3$ | R$^4$ | R$^5$ | L |
|---|---|---|---|---|---|---|---|
| 304 | N | A$^3$ | H | H | A$^1$ | A$^1$ | A$^8$ |
| 305 | N | A$^4$ | H | H | A$^1$ | A$^1$ | A$^8$ |
| 306 | N | A$^5$ | H | H | A$^1$ | A$^1$ | A$^8$ |
| 307 | N | A$^6$ | H | H | A$^1$ | A$^1$ | A$^8$ |
| 308 | N | A$^7$ | H | H | A$^1$ | A$^1$ | A$^8$ |
| 309 | N | A$^1$ | A$^1$ | H | A$^1$ | A$^1$ | A$^8$ |
| 310 | N | A$^2$ | A$^1$ | H | A$^1$ | A$^1$ | A$^8$ |
| 311 | N | A$^3$ | A$^1$ | H | A$^1$ | A$^1$ | A$^8$ |
| 312 | N | A$^4$ | A$^1$ | H | A$^1$ | A$^1$ | A$^8$ |
| 313 | N | A$^5$ | A$^1$ | H | A$^1$ | A$^1$ | A$^8$ |
| 314 | N | A$^6$ | A$^1$ | H | A$^1$ | A$^1$ | A$^8$ |
| 315 | N | A$^7$ | A$^1$ | H | A$^1$ | A$^1$ | A$^8$ |
| 316 | N | A$^1$ | H | A$^1$ | A$^1$ | A$^1$ | A$^8$ |
| 317 | N | A$^2$ | H | A$^1$ | A$^1$ | A$^1$ | A$^8$ |
| 318 | N | A$^3$ | H | A$^1$ | A$^1$ | A$^1$ | A$^8$ |
| 319 | N | A$^4$ | H | A$^1$ | A$^1$ | A$^1$ | A$^8$ |
| 320 | N | A$^5$ | H | A$^1$ | A$^1$ | A$^1$ | A$^8$ |
| 321 | N | A$^6$ | H | A$^1$ | A$^1$ | A$^1$ | A$^8$ |
| 322 | N | A$^7$ | H | A$^1$ | A$^1$ | A$^1$ | A$^8$ |
| 323 | N | A$^1$ | A$^1$ | A$^1$ | A$^1$ | A$^1$ | A$^8$ |
| 324 | N | A$^2$ | A$^1$ | A$^1$ | A$^1$ | A$^1$ | A$^8$ |
| 325 | N | A$^3$ | A$^1$ | A$^1$ | A$^1$ | A$^1$ | A$^8$ |
| 326 | N | A$^4$ | A$^1$ | A$^1$ | A$^1$ | A$^1$ | A$^8$ |
| 327 | N | A$^5$ | A$^1$ | A$^1$ | A$^1$ | A$^1$ | A$^8$ |
| 328 | N | A$^6$ | A$^1$ | A$^1$ | A$^1$ | A$^1$ | A$^8$ |
| 329 | N | A$^7$ | A$^1$ | A$^1$ | A$^1$ | A$^1$ | A$^8$ |
| 330 | N | A$^1$ | H | H | A$^2$ | A$^1$ | A$^8$ |
| 331 | N | A$^2$ | H | H | A$^2$ | A$^1$ | A$^8$ |
| 332 | N | A$^3$ | H | H | A$^2$ | A$^1$ | A$^8$ |
| 333 | N | A$^4$ | H | H | A$^2$ | A$^1$ | A$^8$ |
| 334 | N | A$^5$ | H | H | A$^2$ | A$^1$ | A$^8$ |
| 335 | N | A$^6$ | H | H | A$^2$ | A$^1$ | A$^8$ |
| 336 | N | A$^7$ | H | H | A$^2$ | A$^1$ | A$^8$ |
| 337 | N | A$^1$ | A$^1$ | H | A$^2$ | A$^1$ | A$^8$ |
| 338 | N | A$^2$ | A$^1$ | H | A$^2$ | A$^1$ | A$^8$ |
| 339 | N | A$^3$ | A$^1$ | H | A$^2$ | A$^1$ | A$^8$ |
| 340 | N | A$^4$ | A$^1$ | H | A$^2$ | A$^1$ | A$^8$ |
| 341 | N | A$^5$ | A$^1$ | H | A$^2$ | A$^1$ | A$^8$ |
| 342 | N | A$^6$ | A$^1$ | H | A$^2$ | A$^1$ | A$^8$ |
| 343 | N | A$^7$ | A$^1$ | H | A$^2$ | A$^1$ | A$^8$ |
| 344 | N | A$^1$ | H | A$^1$ | A$^2$ | A$^1$ | A$^8$ |
| 345 | N | A$^2$ | H | A$^1$ | A$^2$ | A$^1$ | A$^8$ |
| 346 | N | A$^3$ | H | A$^1$ | A$^2$ | A$^1$ | A$^8$ |
| 347 | N | A$^4$ | H | A$^1$ | A$^2$ | A$^1$ | A$^8$ |
| 348 | N | A$^5$ | H | A$^1$ | A$^2$ | A$^1$ | A$^8$ |
| 349 | N | A$^6$ | H | A$^1$ | A$^2$ | A$^1$ | A$^8$ |
| 350 | N | A$^7$ | H | A$^1$ | A$^2$ | A$^1$ | A$^8$ |
| 351 | N | A$^1$ | A$^1$ | A$^1$ | A$^2$ | A$^1$ | A$^8$ |
| 352 | N | A$^2$ | A$^1$ | A$^1$ | A$^2$ | A$^1$ | A$^8$ |
| 353 | N | A$^3$ | A$^1$ | A$^1$ | A$^2$ | A$^1$ | A$^8$ |
| 354 | N | A$^4$ | A$^1$ | A$^1$ | A$^2$ | A$^1$ | A$^8$ |
| 355 | N | A$^5$ | A$^1$ | A$^1$ | A$^2$ | A$^1$ | A$^8$ |
| 356 | N | A$^6$ | A$^1$ | A$^1$ | A$^2$ | A$^1$ | A$^8$ |
| 357 | N | A$^7$ | A$^1$ | A$^1$ | A$^2$ | A$^1$ | A$^8$ |
| 358 | N | A$^1$ | H | H | A$^2$ | A$^2$ | A$^8$ |
| 359 | N | A$^2$ | H | H | A$^2$ | A$^2$ | A$^8$ |
| 360 | N | A$^3$ | H | H | A$^2$ | A$^2$ | A$^8$ |
| 361 | N | A$^4$ | H | H | A$^2$ | A$^2$ | A$^8$ |
| 362 | N | A$^5$ | H | H | A$^2$ | A$^2$ | A$^8$ |
| 363 | N | A$^6$ | H | H | A$^2$ | A$^2$ | A$^8$ |
| 364 | N | A$^7$ | H | H | A$^2$ | A$^2$ | A$^8$ |
| 365 | N | A$^1$ | A$^1$ | H | A$^2$ | A$^2$ | A$^8$ |
| 366 | N | A$^2$ | A$^1$ | H | A$^2$ | A$^2$ | A$^8$ |
| 367 | N | A$^3$ | A$^1$ | H | A$^2$ | A$^2$ | A$^8$ |
| 368 | N | A$^4$ | A$^1$ | H | A$^2$ | A$^2$ | A$^8$ |
| 369 | N | A$^5$ | A$^1$ | H | A$^2$ | A$^2$ | A$^8$ |
| 370 | N | A$^6$ | A$^1$ | H | A$^2$ | A$^2$ | A$^8$ |
| 371 | N | A$^7$ | A$^1$ | H | A$^2$ | A$^2$ | A$^8$ |
| 372 | N | A$^1$ | H | A$^1$ | A$^2$ | A$^2$ | A$^8$ |
| 373 | N | A$^2$ | H | A$^1$ | A$^2$ | A$^2$ | A$^8$ |
| 374 | N | A$^3$ | H | A$^1$ | A$^2$ | A$^2$ | A$^8$ |
| 375 | N | A$^4$ | H | A$^1$ | A$^2$ | A$^2$ | A$^8$ |
| 376 | N | A$^5$ | H | A$^1$ | A$^2$ | A$^2$ | A$^8$ |
| 377 | N | A$^6$ | H | A$^1$ | A$^2$ | A$^2$ | A$^8$ |
| 378 | N | A$^7$ | H | A$^1$ | A$^2$ | A$^2$ | A$^8$ |
| 379 | N | A$^1$ | A$^1$ | A$^1$ | A$^2$ | A$^2$ | A$^8$ |
| 380 | N | A$^2$ | A$^1$ | A$^1$ | A$^2$ | A$^2$ | A$^8$ |
| 381 | N | A$^3$ | A$^1$ | A$^1$ | A$^2$ | A$^2$ | A$^8$ |
| 382 | N | A$^4$ | A$^1$ | A$^1$ | A$^2$ | A$^2$ | A$^8$ |
| 383 | N | A$^5$ | A$^1$ | A$^1$ | A$^2$ | A$^2$ | A$^8$ |
| 384 | N | A$^6$ | A$^1$ | A$^1$ | A$^2$ | A$^2$ | A$^8$ |
| 385 | N | A$^7$ | A$^1$ | A$^1$ | A$^2$ | A$^2$ | A$^8$ |
| 386 | N | A$^1$ | H | H | A$^3$ | A$^1$ | A$^8$ |
| 387 | N | A$^2$ | H | H | A$^3$ | A$^1$ | A$^8$ |
| 388 | N | A$^3$ | H | H | A$^3$ | A$^1$ | A$^8$ |
| 389 | N | A$^4$ | H | H | A$^3$ | A$^1$ | A$^8$ |
| 390 | N | A$^5$ | H | H | A$^3$ | A$^1$ | A$^8$ |
| 391 | N | A$^6$ | H | H | A$^3$ | A$^1$ | A$^8$ |
| 392 | N | A$^7$ | H | H | A$^3$ | A$^1$ | A$^8$ |
| 393 | N | A$^1$ | A$^1$ | H | A$^3$ | A$^1$ | A$^8$ |
| 394 | N | A$^2$ | A$^1$ | H | A$^3$ | A$^1$ | A$^8$ |
| 395 | N | A$^3$ | A$^1$ | H | A$^3$ | A$^1$ | A$^8$ |
| 396 | N | A$^4$ | A$^1$ | H | A$^3$ | A$^1$ | A$^8$ |
| 397 | N | A$^5$ | A$^1$ | H | A$^3$ | A$^1$ | A$^8$ |
| 398 | N | A$^6$ | A$^1$ | H | A$^3$ | A$^1$ | A$^8$ |
| 399 | N | A$^7$ | A$^1$ | H | A$^3$ | A$^1$ | A$^8$ |
| 400 | N | A$^1$ | H | A$^1$ | A$^3$ | A$^1$ | A$^8$ |
| 401 | N | A$^2$ | H | A$^1$ | A$^3$ | A$^1$ | A$^8$ |
| 402 | N | A$^3$ | H | A$^1$ | A$^3$ | A$^1$ | A$^8$ |
| 403 | N | A$^4$ | H | A$^1$ | A$^3$ | A$^1$ | A$^8$ |
| 404 | N | A$^5$ | H | A$^1$ | A$^3$ | A$^1$ | A$^8$ |
| 405 | N | A$^6$ | H | A$^1$ | A$^3$ | A$^1$ | A$^8$ |
| 406 | N | A$^7$ | H | A$^1$ | A$^3$ | A$^1$ | A$^8$ |
| 407 | N | A$^1$ | A$^1$ | A$^1$ | A$^3$ | A$^1$ | A$^8$ |
| 408 | N | A$^2$ | A$^1$ | A$^1$ | A$^3$ | A$^1$ | A$^8$ |
| 409 | N | A$^3$ | A$^1$ | A$^1$ | A$^3$ | A$^1$ | A$^8$ |
| 410 | N | A$^4$ | A$^1$ | A$^1$ | A$^3$ | A$^1$ | A$^8$ |
| 411 | N | A$^5$ | A$^1$ | A$^1$ | A$^3$ | A$^1$ | A$^8$ |
| 412 | N | A$^6$ | A$^1$ | A$^1$ | A$^3$ | A$^1$ | A$^8$ |
| 413 | N | A$^7$ | A$^1$ | A$^1$ | A$^3$ | A$^1$ | A$^8$ |
| 414 | N | A$^1$ | H | H | A$^3$ | A$^3$ | A$^8$ |
| 415 | N | A$^2$ | H | H | A$^3$ | A$^3$ | A$^8$ |
| 416 | N | A$^3$ | H | H | A$^3$ | A$^3$ | A$^8$ |
| 417 | N | A$^4$ | H | H | A$^3$ | A$^3$ | A$^8$ |
| 418 | N | A$^5$ | H | H | A$^3$ | A$^3$ | A$^8$ |
| 419 | N | A$^6$ | H | H | A$^3$ | A$^3$ | A$^8$ |
| 420 | N | A$^7$ | H | H | A$^3$ | A$^3$ | A$^8$ |
| 421 | N | A$^1$ | A$^1$ | H | A$^3$ | A$^3$ | A$^8$ |
| 422 | N | A$^2$ | A$^1$ | H | A$^3$ | A$^3$ | A$^8$ |
| 423 | N | A$^3$ | A$^1$ | H | A$^3$ | A$^3$ | A$^8$ |
| 424 | N | A$^4$ | A$^1$ | H | A$^3$ | A$^3$ | A$^8$ |
| 425 | N | A$^5$ | A$^1$ | H | A$^3$ | A$^3$ | A$^8$ |
| 426 | N | A$^6$ | A$^1$ | H | A$^3$ | A$^3$ | A$^8$ |
| 427 | N | A$^7$ | A$^1$ | H | A$^3$ | A$^3$ | A$^8$ |
| 428 | N | A$^1$ | H | A$^1$ | A$^3$ | A$^3$ | A$^8$ |
| 429 | N | A$^2$ | H | A$^1$ | A$^3$ | A$^3$ | A$^8$ |
| 430 | N | A$^3$ | H | A$^1$ | A$^3$ | A$^3$ | A$^8$ |
| 431 | N | A$^4$ | H | A$^1$ | A$^3$ | A$^3$ | A$^8$ |
| 432 | N | A$^5$ | H | A$^1$ | A$^3$ | A$^3$ | A$^8$ |
| 433 | N | A$^6$ | H | A$^1$ | A$^3$ | A$^3$ | A$^8$ |
| 434 | N | A$^7$ | H | A$^1$ | A$^3$ | A$^3$ | A$^8$ |
| 435 | N | A$^1$ | A$^1$ | A$^1$ | A$^3$ | A$^3$ | A$^8$ |
| 436 | N | A$^2$ | A$^1$ | A$^1$ | A$^3$ | A$^3$ | A$^8$ |
| 437 | N | A$^3$ | A$^1$ | A$^1$ | A$^3$ | A$^3$ | A$^8$ |
| 438 | N | A$^4$ | A$^1$ | A$^1$ | A$^3$ | A$^3$ | A$^8$ |
| 439 | N | A$^5$ | A$^1$ | A$^1$ | A$^3$ | A$^3$ | A$^8$ |
| 440 | N | A$^6$ | A$^1$ | A$^1$ | A$^3$ | A$^3$ | A$^8$ |
| 441 | N | A$^7$ | A$^1$ | A$^1$ | A$^3$ | A$^3$ | A$^8$ |
| 442 | N | A$^1$ | A$^2$ | H | A$^1$ | A$^1$ | A$^8$ |
| 443 | N | A$^2$ | A$^2$ | H | A$^1$ | A$^1$ | A$^8$ |
| 444 | N | A$^3$ | A$^2$ | H | A$^1$ | A$^1$ | A$^8$ |
| 445 | N | A$^4$ | A$^2$ | H | A$^1$ | A$^1$ | A$^8$ |
| 446 | N | A$^5$ | A$^2$ | H | A$^1$ | A$^1$ | A$^8$ |
| 447 | N | A$^6$ | A$^2$ | H | A$^1$ | A$^1$ | A$^8$ |
| 448 | N | A$^7$ | A$^2$ | H | A$^1$ | A$^1$ | A$^8$ |
| 449 | N | A$^1$ | A$^2$ | H | A$^2$ | A$^1$ | A$^8$ |
| 450 | N | A$^2$ | A$^2$ | H | A$^2$ | A$^1$ | A$^8$ |
| 451 | N | A$^3$ | A$^2$ | H | A$^2$ | A$^1$ | A$^8$ |
| 452 | N | A$^4$ | A$^2$ | H | A$^2$ | A$^1$ | A$^8$ |
| 453 | N | A$^5$ | A$^2$ | H | A$^2$ | A$^1$ | A$^8$ |
| 454 | N | A$^6$ | A$^2$ | H | A$^2$ | A$^1$ | A$^8$ |
| 455 | N | A$^7$ | A$^2$ | H | A$^2$ | A$^1$ | A$^8$ |
| 456 | N | A$^1$ | A$^2$ | H | A$^2$ | A$^2$ | A$^8$ |
| 457 | N | A$^2$ | A$^2$ | H | A$^2$ | A$^2$ | A$^8$ |
| 458 | N | A$^3$ | A$^2$ | H | A$^2$ | A$^2$ | A$^8$ |
| 459 | N | A$^4$ | A$^2$ | H | A$^2$ | A$^2$ | A$^8$ |

TABLE 1-continued

| Cmpd | $Y^1$ | $R^1$ | $R^2$ | $R^3$ | $R^4$ | $R^5$ | L |
|---|---|---|---|---|---|---|---|
| 460 | N | $A^5$ | $A^2$ | H | $A^2$ | $A^2$ | $A^8$ |
| 461 | N | $A^6$ | $A^2$ | H | $A^2$ | $A^2$ | $A^8$ |
| 462 | N | $A^7$ | $A^2$ | H | $A^2$ | $A^2$ | $A^8$ |
| 463 | C | $A^1$ | H | H | $A^1$ | $A^1$ | $A^8$ |
| 464 | C | $A^2$ | H | H | $A^1$ | $A^1$ | $A^8$ |
| 465 | C | $A^3$ | H | H | $A^1$ | $A^1$ | $A^8$ |
| 466 | C | $A^4$ | H | H | $A^1$ | $A^1$ | $A^8$ |
| 467 | C | $A^5$ | H | H | $A^1$ | $A^1$ | $A^8$ |
| 468 | C | $A^6$ | H | H | $A^1$ | $A^1$ | $A^8$ |
| 469 | C | $A^7$ | H | H | $A^1$ | $A^1$ | $A^8$ |
| 470 | C | $A^1$ | $A^1$ | H | $A^1$ | $A^1$ | $A^8$ |
| 471 | C | $A^2$ | $A^1$ | H | $A^1$ | $A^1$ | $A^8$ |
| 472 | C | $A^3$ | $A^1$ | H | $A^1$ | $A^1$ | $A^8$ |
| 473 | C | $A^4$ | $A^1$ | H | $A^1$ | $A^1$ | $A^8$ |
| 474 | C | $A^5$ | $A^1$ | H | $A^1$ | $A^1$ | $A^8$ |
| 475 | C | $A^6$ | $A^1$ | H | $A^1$ | $A^1$ | $A^8$ |
| 476 | C | $A^7$ | $A^1$ | H | $A^1$ | $A^1$ | $A^8$ |
| 477 | C | $A^1$ | H | $A^1$ | $A^1$ | $A^1$ | $A^8$ |
| 478 | C | $A^2$ | H | $A^1$ | $A^1$ | $A^1$ | $A^8$ |
| 479 | C | $A^3$ | H | $A^1$ | $A^1$ | $A^1$ | $A^8$ |
| 480 | C | $A^4$ | H | $A^1$ | $A^1$ | $A^1$ | $A^8$ |
| 481 | C | $A^5$ | H | $A^1$ | $A^1$ | $A^1$ | $A^8$ |
| 482 | C | $A^6$ | H | $A^1$ | $A^1$ | $A^1$ | $A^8$ |
| 483 | C | $A^7$ | H | $A^1$ | $A^1$ | $A^1$ | $A^8$ |
| 484 | C | $A^1$ | $A^1$ | $A^1$ | $A^1$ | $A^1$ | $A^8$ |
| 485 | C | $A^2$ | $A^1$ | $A^1$ | $A^1$ | $A^1$ | $A^8$ |
| 486 | C | $A^3$ | $A^1$ | $A^1$ | $A^1$ | $A^1$ | $A^8$ |
| 487 | C | $A^4$ | $A^1$ | $A^1$ | $A^1$ | $A^1$ | $A^8$ |
| 488 | C | $A^5$ | $A^1$ | $A^1$ | $A^1$ | $A^1$ | $A^8$ |
| 489 | C | $A^6$ | $A^1$ | $A^1$ | $A^1$ | $A^1$ | $A^8$ |
| 490 | C | $A^7$ | $A^1$ | $A^1$ | $A^1$ | $A^1$ | $A^8$ |
| 491 | C | $A^1$ | H | H | $A^2$ | $A^1$ | $A^8$ |
| 492 | C | $A^2$ | H | H | $A^2$ | $A^1$ | $A^8$ |
| 493 | C | $A^3$ | H | H | $A^2$ | $A^1$ | $A^8$ |
| 494 | C | $A^4$ | H | H | $A^2$ | $A^1$ | $A^8$ |
| 495 | C | $A^5$ | H | H | $A^2$ | $A^1$ | $A^8$ |
| 496 | C | $A^6$ | H | H | $A^2$ | $A^1$ | $A^8$ |
| 497 | C | $A^7$ | H | H | $A^2$ | $A^1$ | $A^8$ |
| 498 | C | $A^1$ | $A^1$ | H | $A^2$ | $A^1$ | $A^8$ |
| 499 | C | $A^2$ | $A^1$ | H | $A^2$ | $A^1$ | $A^8$ |
| 500 | C | $A^3$ | $A^1$ | H | $A^2$ | $A^1$ | $A^8$ |
| 501 | C | $A^4$ | $A^1$ | H | $A^2$ | $A^1$ | $A^8$ |
| 502 | C | $A^5$ | $A^1$ | H | $A^2$ | $A^1$ | $A^8$ |
| 503 | C | $A^6$ | $A^1$ | H | $A^2$ | $A^1$ | $A^8$ |
| 504 | C | $A^7$ | $A^1$ | H | $A^2$ | $A^1$ | $A^8$ |
| 505 | C | $A^1$ | H | $A^1$ | $A^2$ | $A^1$ | $A^8$ |
| 506 | C | $A^2$ | H | $A^1$ | $A^2$ | $A^1$ | $A^8$ |
| 507 | C | $A^3$ | H | $A^1$ | $A^2$ | $A^1$ | $A^8$ |
| 508 | C | $A^4$ | H | $A^1$ | $A^2$ | $A^1$ | $A^8$ |
| 509 | C | $A^5$ | H | $A^1$ | $A^2$ | $A^1$ | $A^8$ |
| 510 | C | $A^6$ | H | $A^1$ | $A^2$ | $A^1$ | $A^8$ |
| 511 | C | $A^7$ | H | $A^1$ | $A^2$ | $A^1$ | $A^8$ |
| 512 | C | $A^1$ | $A^1$ | $A^1$ | $A^2$ | $A^1$ | $A^8$ |
| 513 | C | $A^2$ | $A^1$ | $A^1$ | $A^2$ | $A^1$ | $A^8$ |
| 514 | C | $A^3$ | $A^1$ | $A^1$ | $A^2$ | $A^1$ | $A^8$ |
| 515 | C | $A^4$ | $A^1$ | $A^1$ | $A^2$ | $A^1$ | $A^8$ |
| 516 | C | $A^5$ | $A^1$ | $A^1$ | $A^2$ | $A^1$ | $A^8$ |
| 517 | C | $A^6$ | $A^1$ | $A^1$ | $A^2$ | $A^1$ | $A^8$ |
| 518 | C | $A^7$ | $A^1$ | $A^1$ | $A^2$ | $A^1$ | $A^8$ |
| 519 | C | $A^1$ | H | H | $A^2$ | $A^2$ | $A^8$ |
| 520 | C | $A^2$ | H | H | $A^2$ | $A^2$ | $A^8$ |
| 521 | C | $A^3$ | H | H | $A^2$ | $A^2$ | $A^8$ |
| 522 | C | $A^4$ | H | H | $A^2$ | $A^2$ | $A^8$ |
| 523 | C | $A^5$ | H | H | $A^2$ | $A^2$ | $A^8$ |
| 524 | C | $A^6$ | H | H | $A^2$ | $A^2$ | $A^8$ |
| 525 | C | $A^7$ | H | H | $A^2$ | $A^2$ | $A^8$ |
| 526 | C | $A^1$ | $A^1$ | H | $A^2$ | $A^2$ | $A^8$ |
| 527 | C | $A^2$ | $A^1$ | H | $A^2$ | $A^2$ | $A^8$ |
| 528 | C | $A^3$ | $A^1$ | H | $A^2$ | $A^2$ | $A^8$ |
| 529 | C | $A^4$ | $A^1$ | H | $A^2$ | $A^2$ | $A^8$ |
| 530 | C | $A^5$ | $A^1$ | H | $A^2$ | $A^2$ | $A^8$ |
| 531 | C | $A^6$ | $A^1$ | H | $A^2$ | $A^2$ | $A^8$ |
| 532 | C | $A^7$ | $A^1$ | H | $A^2$ | $A^2$ | $A^8$ |
| 533 | C | $A^1$ | H | $A^1$ | $A^2$ | $A^2$ | $A^8$ |
| 534 | C | $A^2$ | H | $A^1$ | $A^2$ | $A^2$ | $A^8$ |
| 535 | C | $A^3$ | H | $A^1$ | $A^2$ | $A^2$ | $A^8$ |
| 536 | C | $A^4$ | H | $A^1$ | $A^2$ | $A^2$ | $A^8$ |
| 537 | C | $A^5$ | H | $A^1$ | $A^2$ | $A^2$ | $A^8$ |
| 538 | C | $A^6$ | H | $A^1$ | $A^2$ | $A^2$ | $A^8$ |
| 539 | C | $A^7$ | H | $A^1$ | $A^2$ | $A^2$ | $A^8$ |
| 540 | C | $A^1$ | $A^1$ | $A^1$ | $A^2$ | $A^2$ | $A^8$ |
| 541 | C | $A^2$ | $A^1$ | $A^1$ | $A^2$ | $A^2$ | $A^8$ |
| 542 | C | $A^3$ | $A^1$ | $A^1$ | $A^2$ | $A^2$ | $A^8$ |
| 543 | C | $A^4$ | $A^1$ | $A^1$ | $A^2$ | $A^2$ | $A^8$ |
| 544 | C | $A^5$ | $A^1$ | $A^1$ | $A^2$ | $A^2$ | $A^8$ |
| 545 | C | $A^6$ | $A^1$ | $A^1$ | $A^2$ | $A^2$ | $A^8$ |
| 546 | C | $A^7$ | $A^1$ | $A^1$ | $A^2$ | $A^2$ | $A^8$ |
| 547 | C | $A^1$ | H | H | $A^3$ | $A^1$ | $A^8$ |
| 548 | C | $A^2$ | H | H | $A^3$ | $A^1$ | $A^8$ |
| 549 | C | $A^3$ | H | H | $A^3$ | $A^1$ | $A^8$ |
| 550 | C | $A^4$ | H | H | $A^3$ | $A^1$ | $A^8$ |
| 551 | C | $A^5$ | H | H | $A^3$ | $A^1$ | $A^8$ |
| 552 | C | $A^6$ | H | H | $A^3$ | $A^1$ | $A^8$ |
| 553 | C | $A^7$ | H | H | $A^3$ | $A^1$ | $A^8$ |
| 554 | C | $A^1$ | $A^1$ | H | $A^3$ | $A^1$ | $A^8$ |
| 555 | C | $A^2$ | $A^1$ | H | $A^3$ | $A^1$ | $A^8$ |
| 556 | C | $A^3$ | $A^1$ | H | $A^3$ | $A^1$ | $A^8$ |
| 557 | C | $A^4$ | $A^1$ | H | $A^3$ | $A^1$ | $A^8$ |
| 558 | C | $A^5$ | $A^1$ | H | $A^3$ | $A^1$ | $A^8$ |
| 559 | C | $A^6$ | $A^1$ | H | $A^3$ | $A^1$ | $A^8$ |
| 560 | C | $A^7$ | $A^1$ | H | $A^3$ | $A^1$ | $A^8$ |
| 561 | C | $A^1$ | H | $A^1$ | $A^3$ | $A^1$ | $A^8$ |
| 562 | C | $A^2$ | H | $A^1$ | $A^3$ | $A^1$ | $A^8$ |
| 563 | C | $A^3$ | H | $A^1$ | $A^3$ | $A^1$ | $A^8$ |
| 564 | C | $A^4$ | H | $A^1$ | $A^3$ | $A^1$ | $A^8$ |
| 565 | C | $A^5$ | H | $A^1$ | $A^3$ | $A^1$ | $A^8$ |
| 566 | C | $A^6$ | H | $A^1$ | $A^3$ | $A^1$ | $A^8$ |
| 567 | C | $A^7$ | H | $A^1$ | $A^3$ | $A^1$ | $A^8$ |
| 568 | C | $A^1$ | $A^1$ | $A^1$ | $A^3$ | $A^1$ | $A^8$ |
| 569 | C | $A^2$ | $A^1$ | $A^1$ | $A^3$ | $A^1$ | $A^8$ |
| 570 | C | $A^3$ | $A^1$ | $A^1$ | $A^3$ | $A^1$ | $A^8$ |
| 571 | C | $A^4$ | $A^1$ | $A^1$ | $A^3$ | $A^1$ | $A^8$ |
| 572 | C | $A^5$ | $A^1$ | $A^1$ | $A^3$ | $A^1$ | $A^8$ |
| 573 | C | $A^6$ | $A^1$ | $A^1$ | $A^3$ | $A^1$ | $A^8$ |
| 574 | C | $A^7$ | $A^1$ | $A^1$ | $A^3$ | $A^1$ | $A^8$ |
| 575 | C | $A^1$ | H | H | $A^3$ | $A^3$ | $A^8$ |
| 576 | C | $A^2$ | H | H | $A^3$ | $A^3$ | $A^8$ |
| 577 | C | $A^3$ | H | H | $A^3$ | $A^3$ | $A^8$ |
| 578 | C | $A^4$ | H | H | $A^3$ | $A^3$ | $A^8$ |
| 579 | C | $A^5$ | H | H | $A^3$ | $A^3$ | $A^8$ |
| 580 | C | $A^6$ | H | H | $A^3$ | $A^3$ | $A^8$ |
| 581 | C | $A^7$ | H | H | $A^3$ | $A^3$ | $A^8$ |
| 582 | C | $A^1$ | $A^1$ | H | $A^3$ | $A^3$ | $A^8$ |
| 583 | C | $A^2$ | $A^1$ | H | $A^3$ | $A^3$ | $A^8$ |
| 584 | C | $A^3$ | $A^1$ | H | $A^3$ | $A^3$ | $A^8$ |
| 585 | C | $A^4$ | $A^1$ | H | $A^3$ | $A^3$ | $A^8$ |
| 586 | C | $A^5$ | $A^1$ | H | $A^3$ | $A^3$ | $A^8$ |
| 587 | C | $A^6$ | $A^1$ | H | $A^3$ | $A^3$ | $A^8$ |
| 588 | C | $A^7$ | $A^1$ | H | $A^3$ | $A^3$ | $A^8$ |
| 589 | C | $A^1$ | H | $A^1$ | $A^3$ | $A^3$ | $A^8$ |
| 590 | C | $A^2$ | H | $A^1$ | $A^3$ | $A^3$ | $A^8$ |
| 591 | C | $A^3$ | H | $A^1$ | $A^3$ | $A^3$ | $A^8$ |
| 592 | C | $A^4$ | H | $A^1$ | $A^3$ | $A^3$ | $A^8$ |
| 593 | C | $A^5$ | H | $A^1$ | $A^3$ | $A^3$ | $A^8$ |
| 594 | C | $A^6$ | H | $A^1$ | $A^3$ | $A^3$ | $A^8$ |
| 595 | C | $A^7$ | H | $A^1$ | $A^3$ | $A^3$ | $A^8$ |
| 596 | C | $A^1$ | $A^1$ | $A^1$ | $A^3$ | $A^3$ | $A^8$ |
| 597 | C | $A^2$ | $A^1$ | $A^1$ | $A^3$ | $A^3$ | $A^8$ |
| 598 | C | $A^3$ | $A^1$ | $A^1$ | $A^3$ | $A^3$ | $A^8$ |
| 599 | C | $A^4$ | $A^1$ | $A^1$ | $A^3$ | $A^3$ | $A^8$ |
| 600 | C | $A^5$ | $A^1$ | $A^1$ | $A^3$ | $A^3$ | $A^8$ |
| 601 | C | $A^6$ | $A^1$ | $A^1$ | $A^3$ | $A^3$ | $A^8$ |
| 602 | C | $A^7$ | $A^1$ | $A^1$ | $A^3$ | $A^3$ | $A^8$ |

In one embodiment, the compound consists of a compound having the formula:

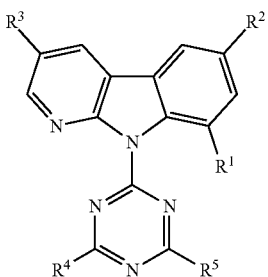

wherein the compound is selected from the group consisting of Compound 603 through Compound 686 listed in the table below (Table 2), wherein $R^1$, $R^2$, $R^3$, $R^4$, and $R^5$ are as defined and wherein H is hydrogen,

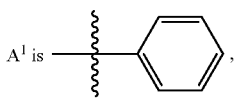

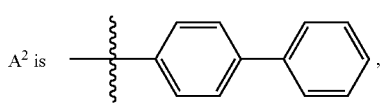

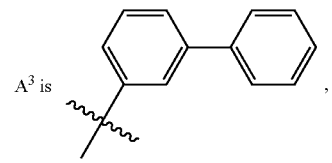

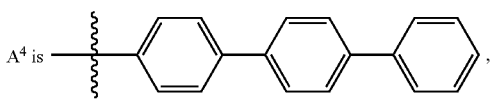

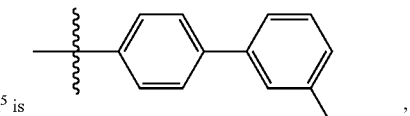

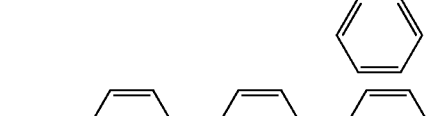

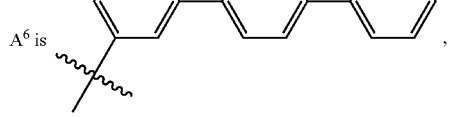

, and

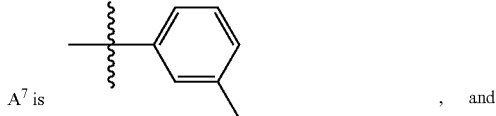

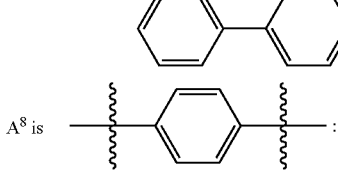

TABLE 2

| Cmpd | $R^1$ | $R^2$ | $R^3$ | $R^4$ | $R^5$ |
|---|---|---|---|---|---|
| 603 | $A^1$ | H | H | $A^1$ | $A^1$ |
| 604 | $A^2$ | H | H | $A^1$ | $A^1$ |
| 605 | $A^3$ | H | H | $A^1$ | $A^1$ |
| 606 | $A^4$ | H | H | $A^1$ | $A^1$ |
| 607 | $A^5$ | H | H | $A^1$ | $A^1$ |
| 608 | $A^6$ | H | H | $A^1$ | $A^1$ |
| 609 | $A^7$ | H | H | $A^1$ | $A^1$ |
| 610 | $A^1$ | $A^1$ | H | $A^1$ | $A^1$ |
| 611 | $A^2$ | $A^1$ | H | $A^1$ | $A^1$ |
| 612 | $A^3$ | $A^1$ | H | $A^1$ | $A^1$ |
| 613 | $A^4$ | $A^1$ | H | $A^1$ | $A^1$ |
| 614 | $A^5$ | $A^1$ | H | $A^1$ | $A^1$ |
| 615 | $A^6$ | $A^1$ | H | $A^1$ | $A^1$ |
| 616 | $A^7$ | $A^1$ | H | $A^1$ | $A^1$ |
| 617 | $A^1$ | H | $A^1$ | $A^1$ | $A^1$ |
| 618 | $A^2$ | H | $A^1$ | $A^1$ | $A^1$ |
| 619 | $A^3$ | H | $A^1$ | $A^1$ | $A^1$ |
| 620 | $A^4$ | H | $A^1$ | $A^1$ | $A^1$ |
| 621 | $A^5$ | H | $A^1$ | $A^1$ | $A^1$ |
| 622 | $A^6$ | H | $A^1$ | $A^1$ | $A^1$ |
| 623 | $A^7$ | H | $A^1$ | $A^1$ | $A^1$ |
| 624 | $A^1$ | $A^1$ | $A^1$ | $A^1$ | $A^1$ |
| 625 | $A^2$ | $A^1$ | $A^1$ | $A^1$ | $A^1$ |
| 626 | $A^3$ | $A^1$ | $A^1$ | $A^1$ | $A^1$ |
| 627 | $A^4$ | $A^1$ | $A^1$ | $A^1$ | $A^1$ |
| 628 | $A^5$ | $A^1$ | $A^1$ | $A^1$ | $A^1$ |
| 629 | $A^6$ | $A^1$ | $A^1$ | $A^1$ | $A^1$ |
| 630 | $A^7$ | $A^1$ | $A^1$ | $A^1$ | $A^1$ |
| 631 | $A^1$ | H | H | $A^2$ | $A^1$ |
| 632 | $A^2$ | H | H | $A^2$ | $A^1$ |
| 633 | $A^3$ | H | H | $A^2$ | $A^1$ |
| 634 | $A^4$ | H | H | $A^2$ | $A^1$ |
| 635 | $A^5$ | H | H | $A^2$ | $A^1$ |
| 636 | $A^6$ | H | H | $A^2$ | $A^1$ |
| 637 | $A^7$ | H | H | $A^2$ | $A^1$ |
| 638 | $A^1$ | $A^1$ | H | $A^2$ | $A^1$ |
| 639 | $A^2$ | $A^1$ | H | $A^2$ | $A^1$ |
| 640 | $A^3$ | $A^1$ | H | $A^2$ | $A^1$ |
| 641 | $A^4$ | $A^1$ | H | $A^2$ | $A^1$ |
| 642 | $A^5$ | $A^1$ | H | $A^2$ | $A^1$ |
| 643 | $A^6$ | $A^1$ | H | $A^2$ | $A^1$ |
| 644 | $A^7$ | $A^1$ | H | $A^2$ | $A^1$ |
| 645 | $A^1$ | H | $A^1$ | $A^2$ | $A^1$ |
| 646 | $A^2$ | H | $A^1$ | $A^2$ | $A^1$ |
| 647 | $A^3$ | H | $A^1$ | $A^2$ | $A^1$ |
| 648 | $A^4$ | H | $A^1$ | $A^2$ | $A^1$ |
| 649 | $A^5$ | H | $A^1$ | $A^2$ | $A^1$ |
| 650 | $A^6$ | H | $A^1$ | $A^2$ | $A^1$ |
| 651 | $A^7$ | H | $A^1$ | $A^2$ | $A^1$ |
| 652 | $A^1$ | $A^1$ | $A^1$ | $A^2$ | $A^1$ |
| 653 | $A^2$ | $A^1$ | $A^1$ | $A^2$ | $A^1$ |
| 654 | $A^3$ | $A^1$ | $A^1$ | $A^2$ | $A^1$ |
| 655 | $A^4$ | $A^1$ | $A^1$ | $A^2$ | $A^1$ |
| 656 | $A^5$ | $A^1$ | $A^1$ | $A^2$ | $A^1$ |
| 657 | $A^6$ | $A^1$ | $A^1$ | $A^2$ | $A^1$ |
| 658 | $A^7$ | $A^1$ | $A^1$ | $A^2$ | $A^1$ |
| 659 | $A^1$ | H | H | $A^2$ | $A^2$ |
| 660 | $A^2$ | H | H | $A^2$ | $A^2$ |
| 661 | $A^3$ | H | H | $A^2$ | $A^2$ |
| 662 | $A^4$ | H | H | $A^2$ | $A^2$ |
| 663 | $A^5$ | H | H | $A^2$ | $A^2$ |
| 664 | $A^6$ | H | H | $A^2$ | $A^2$ |
| 665 | $A^7$ | H | H | $A^2$ | $A^2$ |
| 666 | $A^1$ | $A^1$ | H | $A^2$ | $A^2$ |
| 667 | $A^2$ | $A^1$ | H | $A^2$ | $A^2$ |
| 668 | $A^3$ | $A^1$ | H | $A^2$ | $A^2$ |
| 669 | $A^4$ | $A^1$ | H | $A^2$ | $A^2$ |
| 670 | $A^5$ | $A^1$ | H | $A^2$ | $A^2$ |
| 671 | $A^6$ | $A^1$ | H | $A^2$ | $A^2$ |
| 672 | $A^7$ | $A^1$ | H | $A^2$ | $A^2$ |
| 673 | $A^1$ | H | $A^1$ | $A^2$ | $A^2$ |
| 674 | $A^2$ | H | $A^1$ | $A^2$ | $A^2$ |
| 675 | $A^3$ | H | $A^1$ | $A^2$ | $A^2$ |
| 676 | $A^4$ | H | $A^1$ | $A^2$ | $A^2$ |
| 677 | $A^5$ | H | $A^1$ | $A^2$ | $A^2$ |
| 678 | $A^6$ | H | $A^1$ | $A^2$ | $A^2$ |
| 679 | $A^7$ | H | $A^1$ | $A^2$ | $A^2$ |
| 680 | $A^1$ | $A^1$ | $A^1$ | $A^2$ | $A^2$ |

TABLE 2-continued

| Cmpd | R¹ | R² | R³ | R⁴ | R⁵ |
|------|----|----|----|----|----|
| 681 | A² | A¹ | A¹ | A² | A² |
| 682 | A³ | A¹ | A¹ | A² | A² |
| 683 | A⁴ | A¹ | A¹ | A² | A² |
| 684 | A⁵ | A¹ | A¹ | A² | A² |
| 685 | A⁶ | A¹ | A¹ | A² | A² |
| 686 | A⁷ | A¹ | A¹ | A² | A² |

In one embodiment, the compound consists of a compound having the formula:

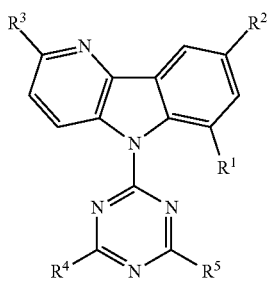

wherein the compound is selected from the group consisting of Compound 687 through Compound 770 listed in the table below (Table 3), wherein $R^1$, $R^2$, $R^3$, $R^4$, and $R^5$ are as defined and wherein H is hydrogen, $A^1$ is

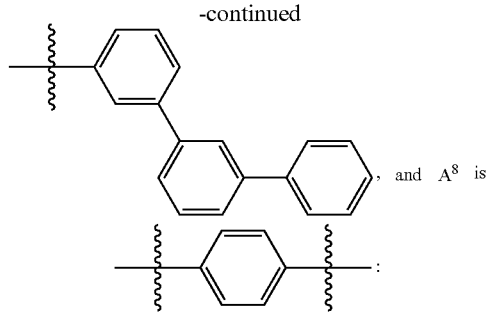

and $A^8$ is:

TABLE 3

| Cmpd | R¹ | R² | R³ | R⁴ | R⁵ |
|------|----|----|----|----|----|
| 687 | A¹ | H | H | A¹ | A¹ |
| 688 | A² | H | H | A¹ | A¹ |
| 689 | A³ | H | H | A¹ | A¹ |
| 690 | A⁴ | H | H | A¹ | A¹ |
| 691 | A⁵ | H | H | A¹ | A¹ |
| 692 | A⁶ | H | H | A¹ | A¹ |
| 693 | A⁷ | H | H | A¹ | A¹ |
| 694 | A¹ | A¹ | H | A¹ | A¹ |
| 695 | A² | A¹ | H | A¹ | A¹ |
| 696 | A³ | A¹ | H | A¹ | A¹ |
| 697 | A⁴ | A¹ | H | A¹ | A¹ |
| 698 | A⁵ | A¹ | H | A¹ | A¹ |
| 699 | A⁶ | A¹ | H | A¹ | A¹ |
| 700 | A⁷ | A¹ | H | A¹ | A¹ |
| 701 | A¹ | H | A¹ | A¹ | A¹ |
| 702 | A² | H | A¹ | A¹ | A¹ |
| 703 | A³ | H | A¹ | A¹ | A¹ |
| 704 | A⁴ | H | A¹ | A¹ | A¹ |
| 705 | A⁵ | H | A¹ | A¹ | A¹ |
| 706 | A⁶ | H | A¹ | A¹ | A¹ |
| 707 | A⁷ | H | A¹ | A¹ | A¹ |
| 708 | A¹ | A¹ | A¹ | A¹ | A¹ |
| 709 | A² | A¹ | A¹ | A¹ | A¹ |
| 710 | A³ | A¹ | A¹ | A¹ | A¹ |
| 711 | A⁴ | A¹ | A¹ | A¹ | A¹ |
| 712 | A⁵ | A¹ | A¹ | A¹ | A¹ |
| 713 | A⁶ | A¹ | A¹ | A¹ | A¹ |
| 714 | A⁷ | A¹ | A¹ | A¹ | A¹ |
| 715 | A¹ | H | H | A² | A¹ |
| 716 | A² | H | H | A² | A¹ |
| 717 | A³ | H | H | A² | A¹ |
| 718 | A⁴ | H | H | A² | A¹ |
| 719 | A⁵ | H | H | A² | A¹ |
| 720 | A⁶ | H | H | A² | A¹ |
| 721 | A⁷ | H | H | A² | A¹ |
| 722 | A¹ | A¹ | H | A² | A¹ |
| 723 | A² | A¹ | H | A² | A¹ |
| 724 | A³ | A¹ | H | A² | A¹ |
| 725 | A⁴ | A¹ | H | A² | A¹ |
| 726 | A⁵ | A¹ | H | A² | A¹ |
| 727 | A⁶ | A¹ | H | A² | A¹ |
| 728 | A⁷ | A¹ | H | A² | A¹ |
| 729 | A¹ | H | A¹ | A² | A¹ |
| 730 | A² | H | A¹ | A² | A¹ |
| 731 | A³ | H | A¹ | A² | A¹ |
| 732 | A⁴ | H | A¹ | A² | A¹ |
| 733 | A⁵ | H | A¹ | A² | A¹ |
| 734 | A⁶ | H | A¹ | A² | A¹ |
| 735 | A⁷ | H | A¹ | A² | A¹ |
| 736 | A¹ | A¹ | A¹ | A² | A¹ |
| 737 | A² | A¹ | A¹ | A² | A¹ |
| 738 | A³ | A¹ | A¹ | A² | A¹ |
| 739 | A⁴ | A¹ | A¹ | A² | A¹ |
| 740 | A⁵ | A¹ | A¹ | A² | A¹ |
| 741 | A⁶ | A¹ | A¹ | A² | A¹ |
| 742 | A⁷ | A¹ | A¹ | A² | A¹ |
| 743 | A¹ | H | H | A² | A² |
| 744 | A² | H | H | A² | A² |
| 745 | A³ | H | H | A² | A² |
| 746 | A⁴ | H | H | A² | A² |

TABLE 3-continued

| Cmpd | R¹ | R² | R³ | R⁴ | R⁵ |
|------|----|----|----|----|-----|
| 747 | A⁵ | H | H | A² | A² |
| 748 | A⁶ | H | H | A² | A² |
| 749 | A⁷ | H | H | A² | A² |
| 750 | A¹ | A¹ | H | A² | A² |
| 751 | A² | A¹ | H | A² | A² |
| 752 | A³ | A¹ | H | A² | A² |
| 753 | A⁴ | A¹ | H | A² | A² |
| 754 | A⁵ | A¹ | H | A² | A² |
| 755 | A⁶ | A¹ | H | A² | A² |
| 756 | A⁷ | A¹ | H | A² | A² |
| 757 | A¹ | H | A¹ | A² | A² |
| 758 | A² | H | A¹ | A² | A² |
| 759 | A³ | H | A¹ | A² | A² |
| 760 | A⁴ | H | A¹ | A² | A² |
| 761 | A⁵ | H | A¹ | A² | A² |
| 762 | A⁶ | H | A¹ | A² | A² |
| 763 | A⁷ | H | A¹ | A² | A² |
| 764 | A¹ | A¹ | A¹ | A² | A² |
| 765 | A² | A¹ | A¹ | A² | A² |
| 766 | A³ | A¹ | A¹ | A² | A² |
| 767 | A⁴ | A¹ | A¹ | A² | A² |
| 768 | A⁵ | A¹ | A¹ | A² | A² |
| 769 | A⁶ | A¹ | A¹ | A² | A² |
| 770 | A⁷ | A¹ | A¹ | A² | A² |

In one embodiment, the compound consists of a compound having the formula:

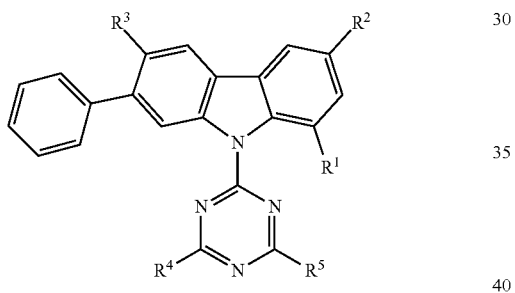

wherein the compound is selected from the group consisting of Compound 771 through Compound 854 listed in the table below (Table 4), wherein R¹, R², R³, R⁴, and R⁵ are as defined and wherein H is hydrogen, A¹ is

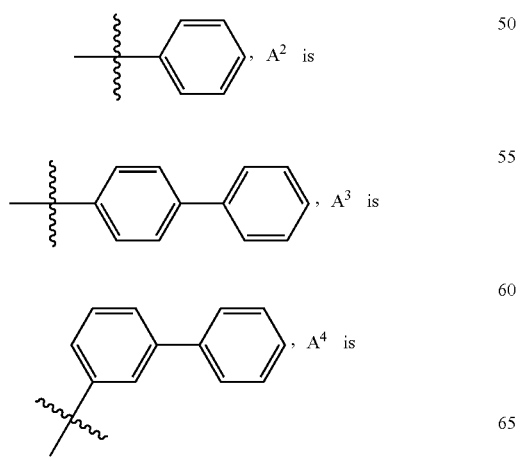

, A² is

, A³ is

, A⁴ is

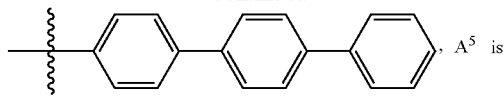

, A⁵ is

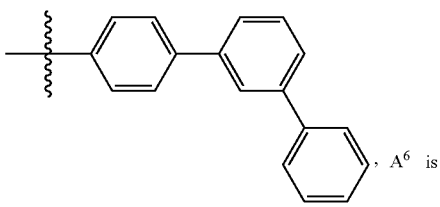

, A⁶ is

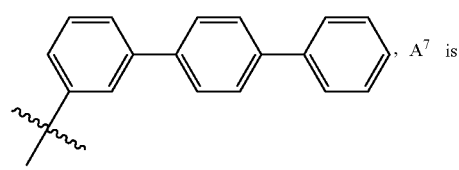

, A⁷ is

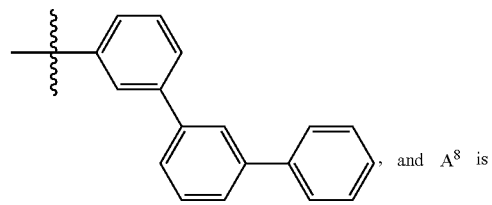

, and A⁸ is

:

TABLE 4

| Cmpd | R¹ | R² | R³ | R⁴ | R⁵ |
|------|----|----|----|----|-----|
| 771 | A¹ | H | H | A¹ | A¹ |
| 772 | A² | H | H | A¹ | A¹ |
| 773 | A³ | H | H | A¹ | A¹ |
| 774 | A⁴ | H | H | A¹ | A¹ |
| 775 | A⁵ | H | H | A¹ | A¹ |
| 776 | A⁶ | H | H | A¹ | A¹ |
| 777 | A⁷ | H | H | A¹ | A¹ |
| 778 | A¹ | A¹ | H | A¹ | A¹ |
| 779 | A² | A¹ | H | A¹ | A¹ |
| 780 | A³ | A¹ | H | A¹ | A¹ |
| 781 | A⁴ | A¹ | H | A¹ | A¹ |
| 782 | A⁵ | A¹ | H | A¹ | A¹ |
| 783 | A⁶ | A¹ | H | A¹ | A¹ |
| 784 | A⁷ | A¹ | H | A¹ | A¹ |
| 785 | A¹ | H | A¹ | A¹ | A¹ |
| 786 | A² | H | A¹ | A¹ | A¹ |
| 787 | A³ | H | A¹ | A¹ | A¹ |
| 788 | A⁴ | H | A¹ | A¹ | A¹ |
| 789 | A⁵ | H | A¹ | A¹ | A¹ |
| 790 | A⁶ | H | A¹ | A¹ | A¹ |
| 791 | A⁷ | H | A¹ | A¹ | A¹ |
| 792 | A¹ | A¹ | A¹ | A¹ | A¹ |
| 793 | A² | A¹ | A¹ | A¹ | A¹ |
| 794 | A³ | A¹ | A¹ | A¹ | A¹ |
| 795 | A⁴ | A¹ | A¹ | A¹ | A¹ |
| 796 | A⁵ | A¹ | A¹ | A¹ | A¹ |
| 797 | A⁶ | A¹ | A¹ | A¹ | A¹ |

TABLE 4-continued

| Cmpd | R¹ | R² | R³ | R⁴ | R⁵ |
|------|-----|-----|-----|-----|-----|
| 798 | A⁷ | A¹ | A¹ | A¹ | A¹ |
| 799 | A¹ | H | H | A² | A¹ |
| 800 | A² | H | H | A² | A¹ |
| 801 | A³ | H | H | A² | A¹ |
| 802 | A⁴ | H | H | A² | A¹ |
| 803 | A⁵ | H | H | A² | A¹ |
| 804 | A⁶ | H | H | A² | A¹ |
| 805 | A⁷ | H | H | A² | A¹ |
| 806 | A¹ | A¹ | H | A² | A¹ |
| 807 | A² | A¹ | H | A² | A¹ |
| 808 | A³ | A¹ | H | A² | A¹ |
| 809 | A⁴ | A¹ | H | A² | A¹ |
| 810 | A⁵ | A¹ | H | A² | A¹ |
| 811 | A⁶ | A¹ | H | A² | A¹ |
| 812 | A⁷ | A¹ | H | A² | A¹ |
| 813 | A¹ | H | A¹ | A² | A¹ |
| 814 | A² | H | A¹ | A² | A¹ |
| 815 | A³ | H | A¹ | A² | A¹ |
| 816 | A⁴ | H | A¹ | A² | A¹ |
| 817 | A⁵ | H | A¹ | A² | A¹ |
| 818 | A⁶ | H | A¹ | A² | A¹ |
| 819 | A⁷ | H | A¹ | A² | A¹ |
| 820 | A¹ | A¹ | A¹ | A² | A¹ |
| 821 | A² | A¹ | A¹ | A² | A¹ |
| 822 | A³ | A¹ | A¹ | A² | A¹ |
| 823 | A⁴ | A¹ | A¹ | A² | A¹ |
| 824 | A⁵ | A¹ | A¹ | A² | A¹ |
| 825 | A⁶ | A¹ | A¹ | A² | A¹ |
| 826 | A⁷ | A¹ | A¹ | A² | A¹ |
| 827 | A¹ | H | H | A² | A² |
| 828 | A² | H | H | A² | A² |
| 829 | A³ | H | H | A² | A² |
| 830 | A⁴ | H | H | A² | A² |
| 831 | A⁵ | H | H | A² | A² |
| 832 | A⁶ | H | H | A² | A² |
| 833 | A⁷ | H | H | A² | A² |
| 834 | A¹ | A¹ | H | A² | A² |
| 835 | A² | A¹ | H | A² | A² |
| 836 | A³ | A¹ | H | A² | A² |
| 837 | A⁴ | A¹ | H | A² | A² |
| 838 | A⁵ | A¹ | H | A² | A² |
| 839 | A⁶ | A¹ | H | A² | A² |
| 840 | A⁷ | A¹ | H | A² | A² |
| 841 | A¹ | H | A¹ | A² | A² |
| 842 | A² | H | A¹ | A² | A² |
| 843 | A³ | H | A¹ | A² | A² |
| 844 | A⁴ | H | A¹ | A² | A² |
| 845 | A⁵ | H | A¹ | A² | A² |
| 846 | A⁶ | H | A¹ | A² | A² |
| 847 | A⁷ | H | A¹ | A² | A² |
| 848 | A¹ | A¹ | A¹ | A² | A² |
| 849 | A² | A¹ | A¹ | A² | A² |
| 850 | A³ | A¹ | A¹ | A² | A² |
| 851 | A⁴ | A¹ | A¹ | A² | A² |
| 852 | A⁵ | A¹ | A¹ | A² | A² |
| 853 | A⁶ | A¹ | A¹ | A² | A² |
| 854 | A⁷ | A¹ | A¹ | A² | A² |

In one embodiment, the compound consists of a compound having the formula:

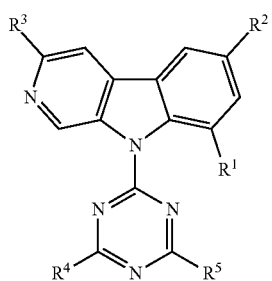

wherein the compound is selected from the group consisting of Compound 855 through Compound 938 listed in the table below (Table 5), wherein $R^1$, $R^2$, $R^3$, $R^4$, and $R^5$ are as defined and wherein H is hydrogen, $A^1$ is

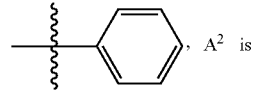, $A^2$ is

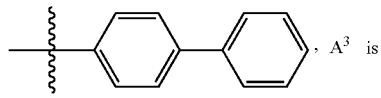, $A^3$ is

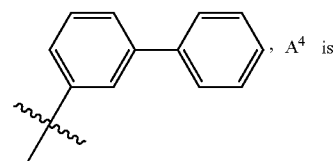, $A^4$ is

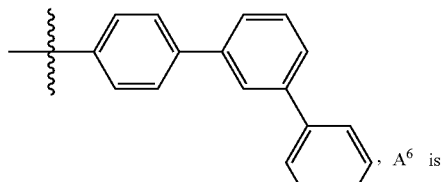, $A^5$ is

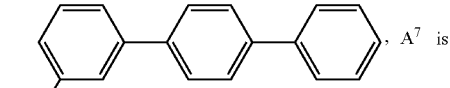, $A^6$ is

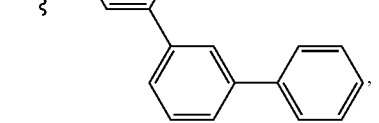, $A^7$ is

, and $A^8$ is

:

TABLE 5

| Cmpd | R¹ | R² | R³ | R⁴ | R⁵ |
|------|-----|-----|-----|-----|-----|
| 855 | A¹ | H | H | A¹ | A¹ |
| 856 | A² | H | H | A¹ | A¹ |
| 857 | A³ | H | H | A¹ | A¹ |
| 858 | A⁴ | H | H | A¹ | A¹ |
| 859 | A⁵ | H | H | A¹ | A¹ |
| 860 | A⁶ | H | H | A¹ | A¹ |

TABLE 5-continued

| Cmpd | R¹ | R² | R³ | R⁴ | R⁵ |
|---|---|---|---|---|---|
| 861 | A⁷ | H | H | A¹ | A¹ |
| 862 | A¹ | A¹ | H | A¹ | A¹ |
| 863 | A² | A¹ | H | A¹ | A¹ |
| 864 | A³ | A¹ | H | A¹ | A¹ |
| 865 | A⁴ | A¹ | H | A¹ | A¹ |
| 866 | A⁵ | A¹ | H | A¹ | A¹ |
| 867 | A⁶ | A¹ | H | A¹ | A¹ |
| 868 | A⁷ | A¹ | H | A¹ | A¹ |
| 869 | A¹ | H | A¹ | A¹ | A¹ |
| 870 | A² | H | A¹ | A¹ | A¹ |
| 871 | A³ | H | A¹ | A¹ | A¹ |
| 872 | A⁴ | H | A¹ | A¹ | A¹ |
| 873 | A⁵ | H | A¹ | A¹ | A¹ |
| 874 | A⁶ | H | A¹ | A¹ | A¹ |
| 875 | A⁷ | H | A¹ | A¹ | A¹ |
| 876 | A¹ | A¹ | A¹ | A¹ | A¹ |
| 877 | A² | A¹ | A¹ | A¹ | A¹ |
| 878 | A³ | A¹ | A¹ | A¹ | A¹ |
| 879 | A⁴ | A¹ | A¹ | A¹ | A¹ |
| 880 | A⁵ | A¹ | A¹ | A¹ | A¹ |
| 881 | A⁶ | A¹ | A¹ | A¹ | A¹ |
| 882 | A⁷ | A¹ | A¹ | A¹ | A¹ |
| 883 | A¹ | H | H | A² | A¹ |
| 884 | A² | H | H | A² | A¹ |
| 885 | A³ | H | H | A² | A¹ |
| 886 | A⁴ | H | H | A² | A¹ |
| 887 | A⁵ | H | H | A² | A¹ |
| 888 | A⁶ | H | H | A² | A¹ |
| 889 | A⁷ | H | H | A² | A¹ |
| 890 | A¹ | A¹ | H | A² | A¹ |
| 891 | A² | A¹ | H | A² | A¹ |
| 892 | A³ | A¹ | H | A² | A¹ |
| 893 | A⁴ | A¹ | H | A² | A¹ |
| 894 | A⁵ | A¹ | H | A² | A¹ |
| 895 | A⁶ | A¹ | H | A² | A¹ |
| 896 | A⁷ | A¹ | H | A² | A¹ |
| 897 | A¹ | H | A¹ | A² | A¹ |
| 898 | A² | H | A¹ | A² | A¹ |
| 899 | A³ | H | A¹ | A² | A¹ |
| 900 | A⁴ | H | A¹ | A² | A¹ |
| 901 | A⁵ | H | A¹ | A² | A¹ |
| 902 | A⁶ | H | A¹ | A² | A¹ |
| 903 | A⁷ | H | A¹ | A² | A¹ |
| 904 | A¹ | A¹ | A¹ | A² | A¹ |
| 905 | A² | A¹ | A¹ | A² | A¹ |
| 906 | A³ | A¹ | A¹ | A² | A¹ |
| 907 | A⁴ | A¹ | A¹ | A² | A¹ |
| 908 | A⁵ | A¹ | A¹ | A² | A¹ |
| 909 | A⁶ | A¹ | A¹ | A² | A¹ |
| 910 | A⁷ | A¹ | A¹ | A² | A¹ |
| 911 | A¹ | H | H | A² | A² |
| 912 | A² | H | H | A² | A² |
| 913 | A³ | H | H | A² | A² |
| 914 | A⁴ | H | H | A² | A² |
| 915 | A⁵ | H | H | A² | A² |
| 916 | A⁶ | H | H | A² | A² |
| 917 | A⁷ | H | H | A² | A² |
| 918 | A¹ | A¹ | H | A² | A² |
| 919 | A² | A¹ | H | A² | A² |
| 920 | A³ | A¹ | H | A² | A² |
| 921 | A⁴ | A¹ | H | A² | A² |
| 922 | A⁵ | A¹ | H | A² | A² |
| 923 | A⁶ | A¹ | H | A² | A² |
| 924 | A⁷ | A¹ | H | A² | A² |
| 925 | A¹ | H | A¹ | A² | A² |
| 926 | A² | H | A¹ | A² | A² |
| 927 | A³ | H | A¹ | A² | A² |
| 928 | A⁴ | H | A¹ | A² | A² |
| 929 | A⁵ | H | A¹ | A² | A² |
| 930 | A⁶ | H | A¹ | A² | A² |
| 931 | A⁷ | H | A¹ | A² | A² |
| 932 | A¹ | A¹ | A¹ | A² | A² |
| 933 | A² | A¹ | A¹ | A² | A² |
| 934 | A³ | A¹ | A¹ | A² | A² |
| 935 | A⁴ | A¹ | A¹ | A² | A² |
| 936 | A⁵ | A¹ | A¹ | A² | A² |
| 937 | A⁶ | A¹ | A¹ | A² | A² |
| 938 | A⁷ | A¹ | A¹ | A² | A² |

In one embodiment, the compound is selected from the group consisting of:

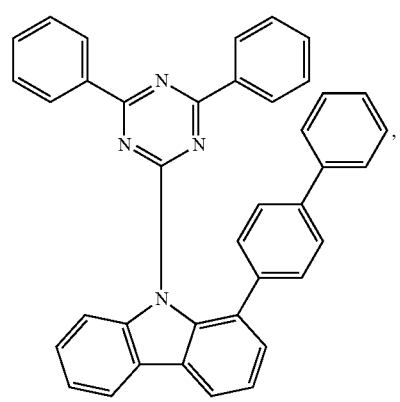

Compound 2

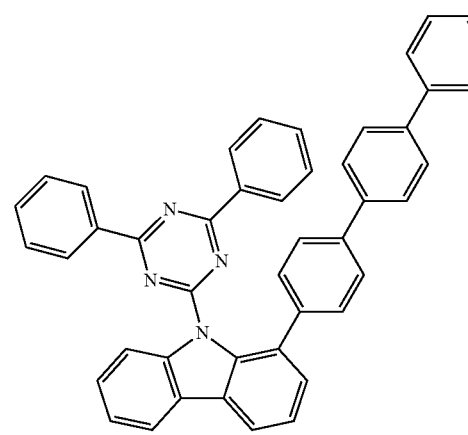

Compound 4

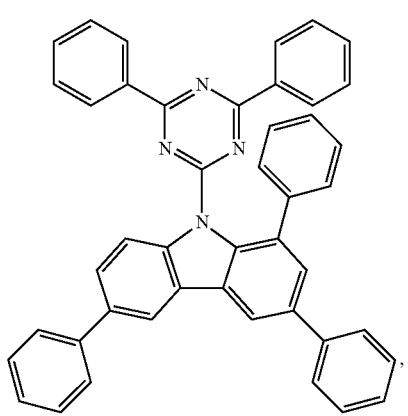

Compound 22

Compound 30
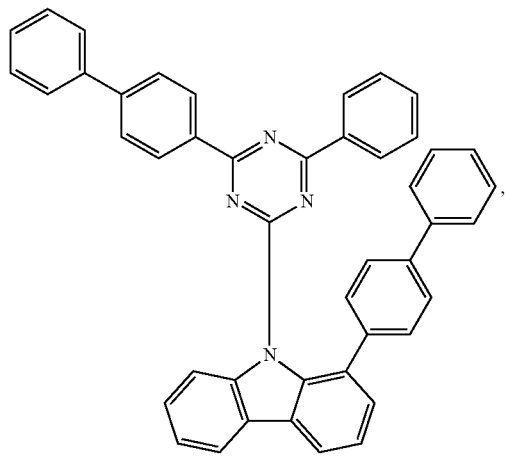
Compound 64
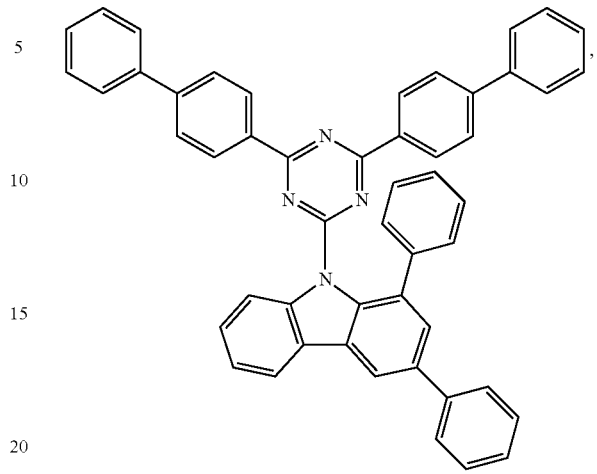
Compound 36
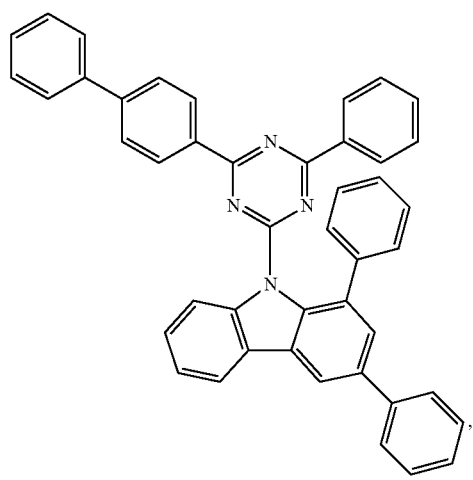
Compound 142
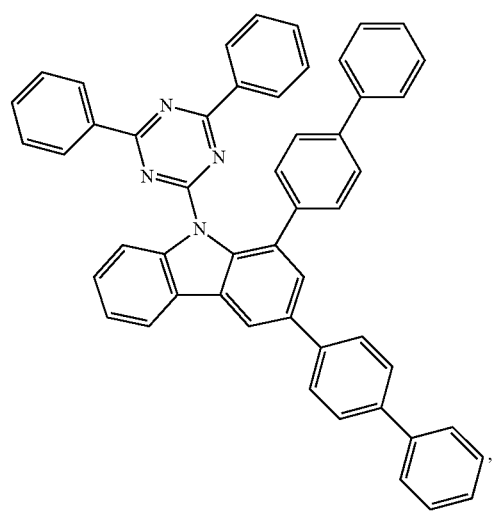
Compound 57
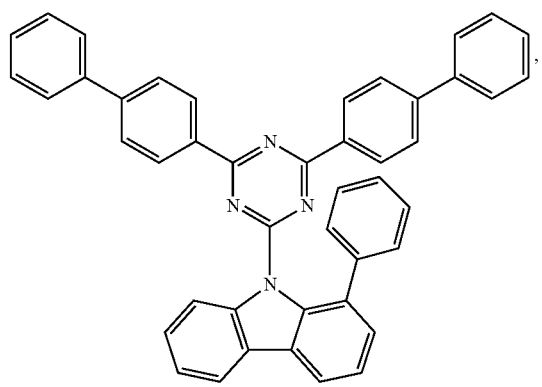
Compound 303
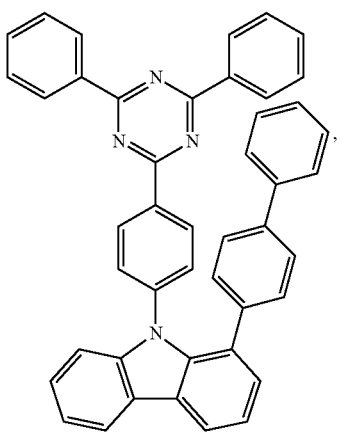

-continued

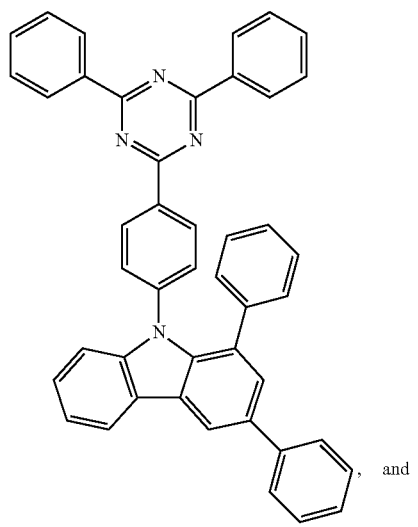

Compound 309

, and

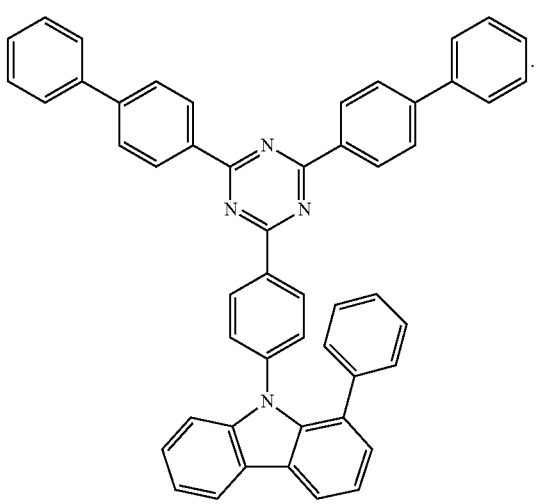

Compound 358

In one aspect, a formulation comprising a compound of formula I is provided.

In one aspect, a first device comprising a first organic light emitting device, further comprising: an anode; a cathode; an organic layer, disposed between the anode and the cathode, wherein the organic layer further comprising a compound having a structure according to Formula I

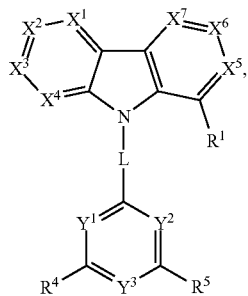

Formula I wherein $R^1$, $R^4$ and $R^5$ are independently selected from group consisting of non-fused aryl, non-fused heteroaryl, and combinations thereof; wherein L is selected from the group consisting of a bond, non-fused aryl, non-fused heteroaryl, and combinations thereof; wherein $X^1$, $X^2$, $X^3$, $X^4$, $X^5$, $X^6$, $X^7$, $Y^1$, $Y^2$, and $Y^3$ are each independently selected from the group consisting of CR and N; wherein at least two of $Y^1$, $Y^2$, and $Y^3$ are N; and wherein each R can be same or different, and is independently selected from the group consisting of hydrogen, deuterium, non-fused aryl, non-fused heteroaryl and combinations thereof, is provided.

In one embodiment, $R^1$ is selected from the group consisting of phenyl, biphenyl, terphenyl, tetraphenyl, pentaphenyl, pyridine, phenyl pyridine and pyridyl phenyl. In one embodiment, L is selected from the group consisting of phenyl, pyridyl, biphenyl, terphenyl and a bond. In one embodiment, $R^4$ is selected from the group consisting of phenyl, pyridyl, biphenyl, and terphenyl. In one embodiment, $R^5$ is selected from the group consisting of phenyl, pyridyl, biphenyl, and terphenyl. In one embodiment, the compound consists of a compound having a structure according to Formula II:

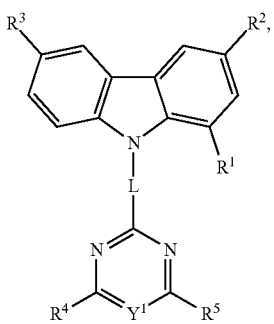

Formula II wherein $R_2$ and $R_3$ can be same or different, and independently selected from the group consisting of hydrogen, deuterium, non-fused aryl, non-fused heteroaryl and combinations thereof.

In one embodiment, the first device is an organic light-emitting device. In one embodiment, the first device comprises a lighting panel. In one embodiment, the compound is selected from the group consisting of:

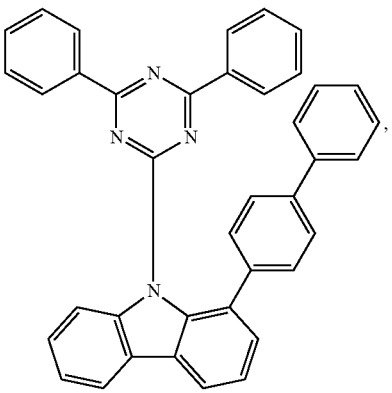

Compound 2

Compound 4
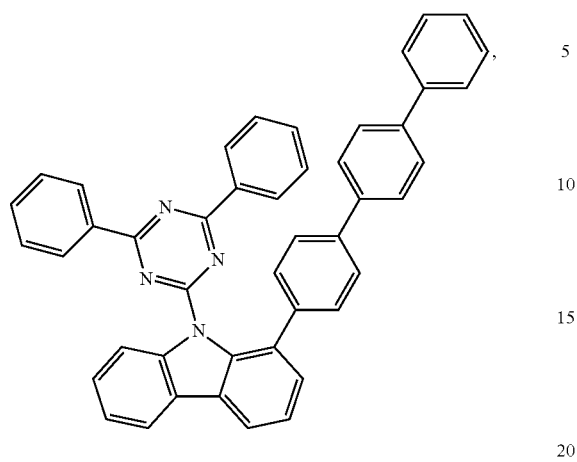
Compound 36
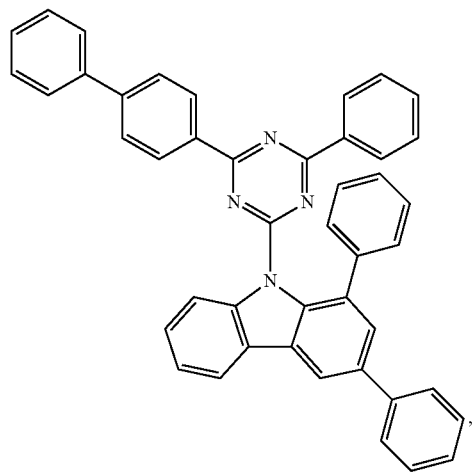
Compound 22
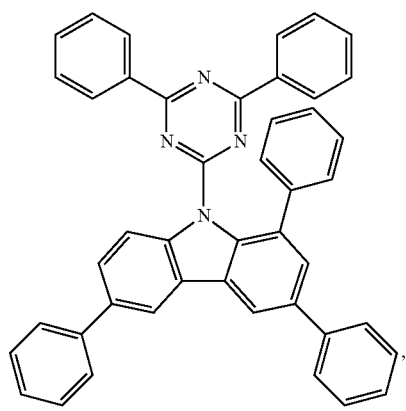
Compound 57
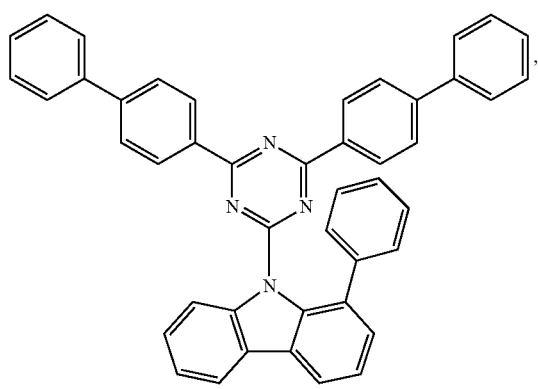
Compound 30
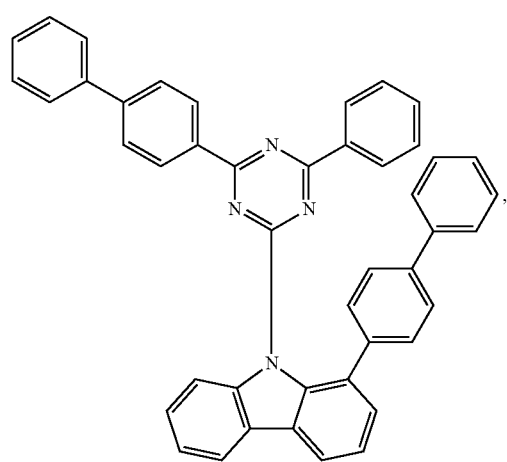
Compound 64
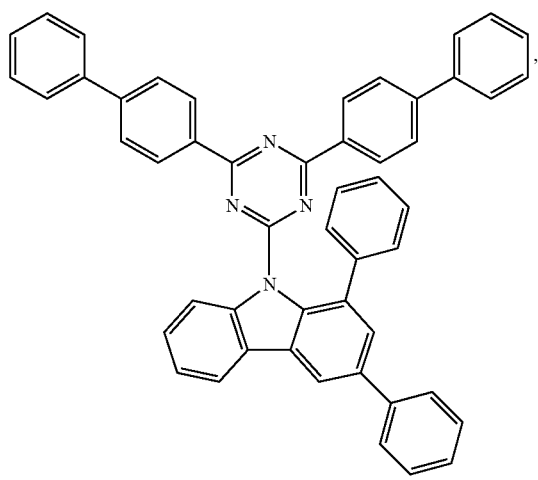

Compound 142

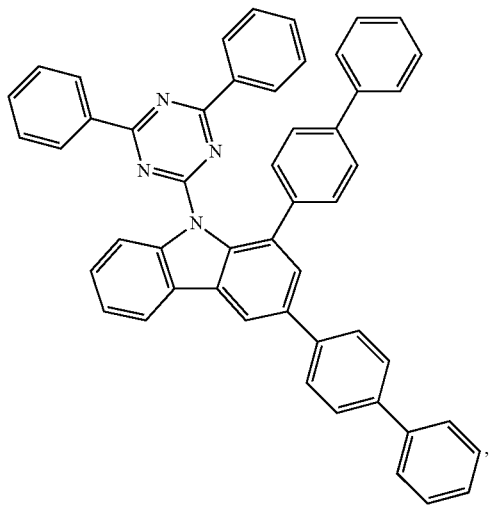

Compound 358

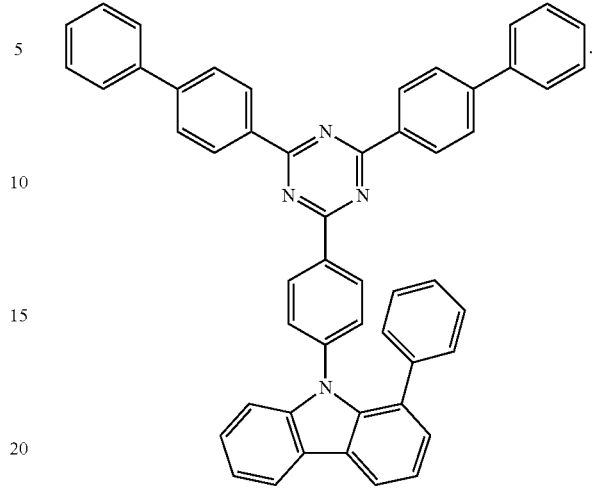

Compound 303

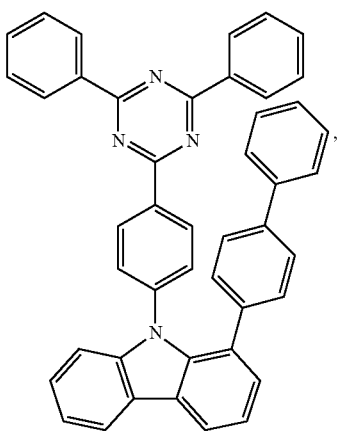

Compound 309

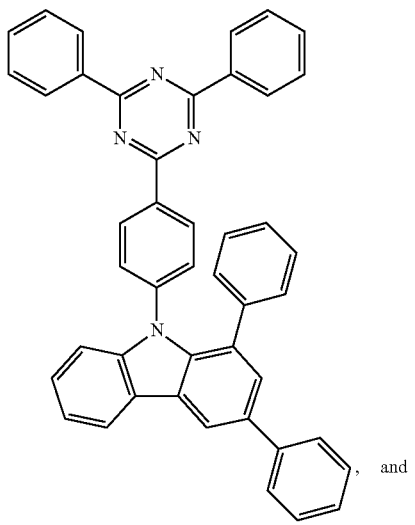

, and

In one embodiment, the compound is selected from the compounds 1 through 602. In one embodiment, the compound is selected from the compounds 603 to 686. In one embodiment, the compound is selected from the compounds 687 to 770. In one embodiment, the compound is selected from the compounds 771 to 854. In one embodiment, the compound is selected from the compounds 855 to 938.

In one embodiment, the first device is a consumer product. In one embodiment, the organic layer is an emissive layer and the compound of Formula I is a host. In one embodiment, the organic layer is a blocking layer and the compound having the formula I is a blocking material in the organic layer. In one embodiment, the organic layer is an electron transporting layer and the compound having the formula I is an electron transporting material in the organic layer. In a further embodiment, the compound comprising a first dopant material that is an emissive dopant comprising a transition metal complex having at least one ligand or part of the ligand if the ligand is more than bidentate selected from the group consisting of:

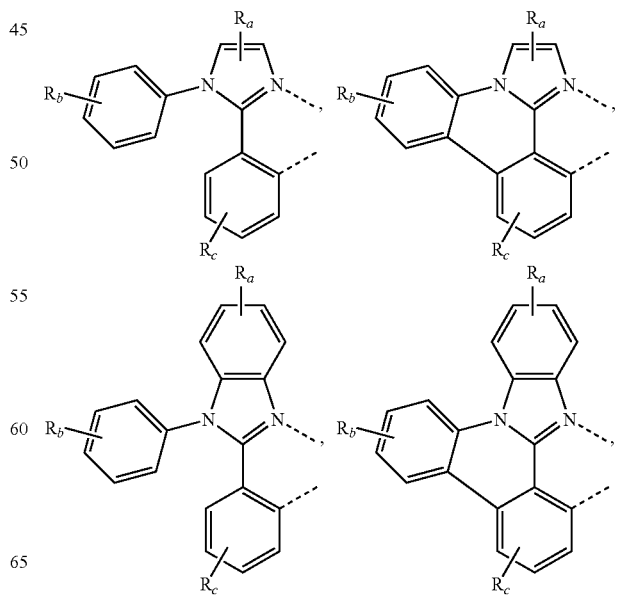

-continued
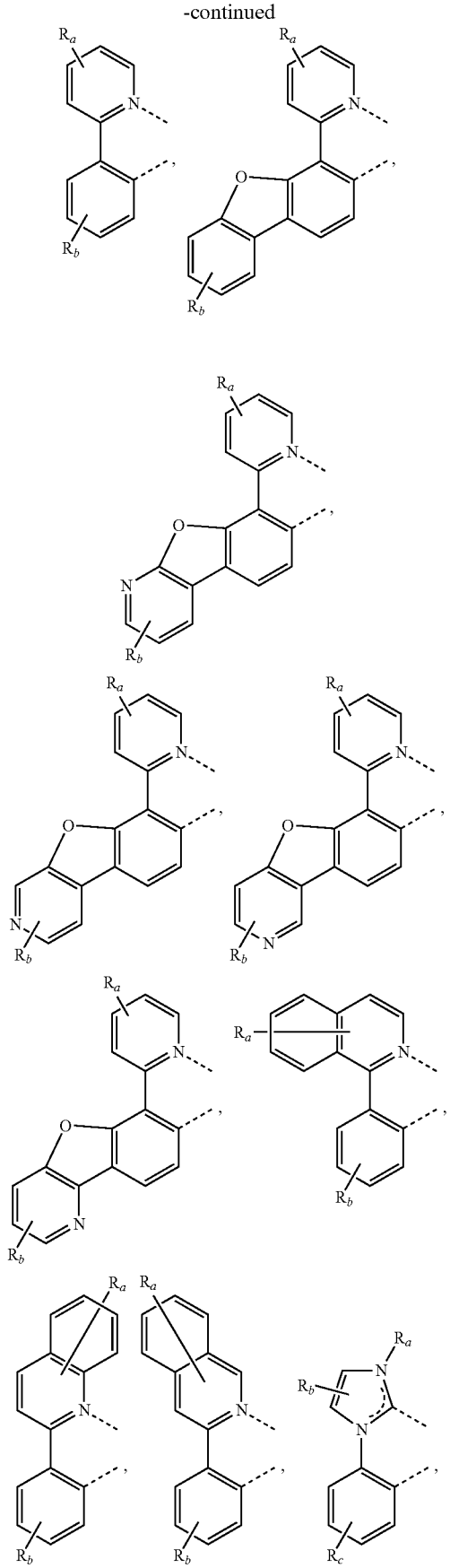
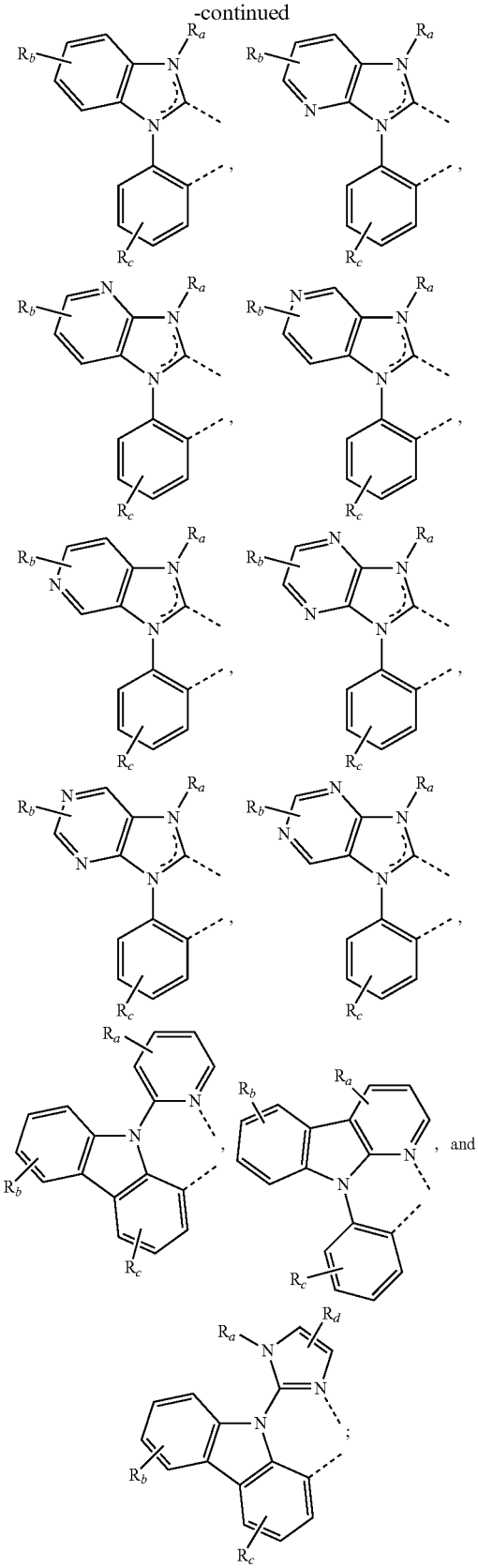
wherein $R_a$, $R_b$, and $R_c$ may represent mono, di, tri or tetra substitutions; $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and two adjacent substituents of $R_a$, $R_b$, and $R_c$, are optionally joined to form a fused ring or form a multidentate ligand.

The exemplary compounds described herein comprise either carbazole or azacarbazole central unit. The compounds can be substituted directly at the 9-position with a triazine or a pyrimidine unit and with an aromatic unfused ring at the 1-position. The triazine linked to the 9-position of the carbazole can be further substituted by two similar aromatic rings or by two different substituents.

The compounds described in this disclosure were found to have surprising and unexpected properties when used as electron-transporting hosts in the emissive layer of an organic light-emitting device.

The present disclosure is based, at least in part, on the surprising and unexpected discovery that certain combinations of 1-arylated carbazole with either pyrimidine or triazine attached at the 9-position (nitrogen) of the carbazole contain two important parts, namely an electron rich part (carbazole) and an electron poor part (triazine). The substitution at the 1-position of the carbazole resulted in surprising and unexpected properties in order to provide steric hindrance which results twisting of the carbazole vs. triazine fragment. This substitution also enabled the compounds described herein to be completely amorphous and therefore they form higher quality films on the substrates.

As shown in the examples, non-exemplary compounds that do not have these characteristic substitution show worse performance characteristics and lifetimes compared to their 1-substituted counterpart as described in the present disclosure. The type of substituents on the carbazole and triazine are very important for the improved properties. It was found that small pendant groups were very efficient in providing good performance characteristics. The number of substituents were optimized and/or selected based on the glass transition temperature ($T_G$) and deposition temperature ($T_D$), which are very important factors in obtaining stable devices.

Generally, un-fused pendant groups that do not increase the rigidity of the material were used. For example, the carbazole, as well as the triazine groups, can be substituted with phenyl, biphenyl, terphenyl, and pyridine units. The known compounds that contain the triazine substituted carbazole usually contain other fused heterocycles like dibenzothiophene, dibenzofuran, or carbazole, which are unlike the compounds of the present disclosure comprising certain combinations of carbazole and triazine, both substituted with small and unfused pendant groups. Other dimer-like structures of such compounds are complicated to synthesize while not providing device improvement. The use of simple aryl units such as phenyl or pyridine makes the synthesis very straightforward and easy because of the availability of several commercial intermediates. Moreover, the $T_G$ and $T_D$ are much easier to adjust when using exemplary aryl units because their molecular weights are much smaller and increase these temperatures by a small amount compared to the bigger fused units.

In certain embodiments of the present disclosure, the three pendant groups on the triazine moiety can be different. The exemplary functionalization is having one larger group on one end of the triazine and two other small units which are usually the same (phenyl). As shown herein, exemplary compounds described herein can be very efficient materials (host and blocking layer OLEDs for green and red emissive layer) and can be obtained by having three different functional groups on the triazine. This allows more freedom in terms of chemistry and possibility for the synthesis of new materials. In certain aspects, the present disclosure is not limited to changing one third of the pendant groups on the triazine but all of them.

In general, the carbazole unit substituted with different triazine or pyrimidine units on the nitrogen combined with substitution with small pendant groups has great advantages as electron-transporting host. First of all, having a triazine unit on the carbazole moiety helps affording very good external quantum efficiency (EQE) and power efficacy (PE) in the devices. Furthermore, the addition of a pendant group at the 1-position on the carbazole lowers the driving voltage and also improves the lifetimes of the devices which are important problems to solve in the industry in order to have a viable host system and commercial development.

An organic light-emitting device is also provided. The device may include an anode, a cathode, and an organic emissive layer disposed between the anode and the cathode. The organic emissive layer may include a host and a phosphorescent dopant.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

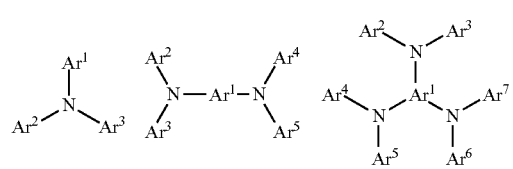

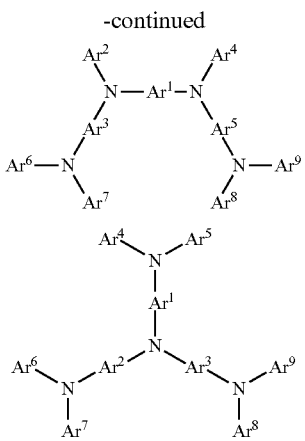

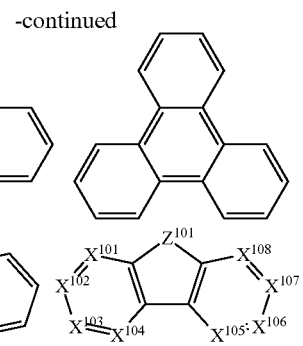

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

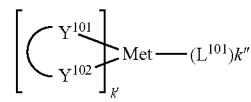

wherein Met is a metal; ($Y^{101}$—$Y^{102}$) is a bidentate ligand, $Y^{101}$ and $Y^{102}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, ($Y^{101}$—$Y^{102}$) is a 2-phenylpyridine derivative. In another aspect, ($Y^{101}$—$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criterion is satisfied.

Examples of metal complexes used as host are preferred to have the following general formula:

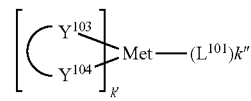

wherein Met is a metal; ($Y^{103}$—$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

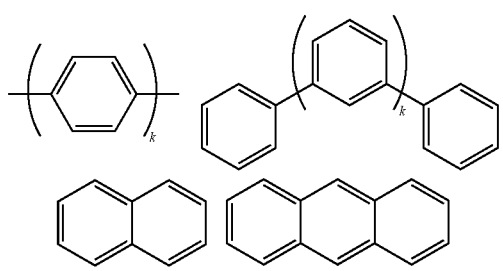

In one aspect, the metal complexes are:

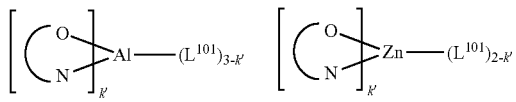

wherein (O—N) is a bidentate ligand, having metal coordinated to atoms O and N.

In another aspect, Met is selected from Ir and Pt. In a further aspect, ($Y^{103}$—$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

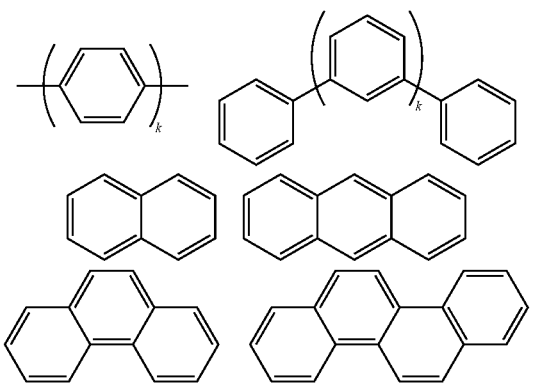

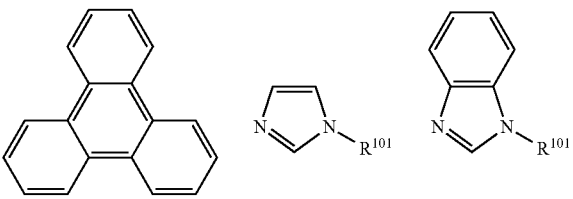

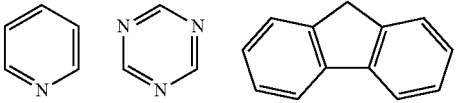

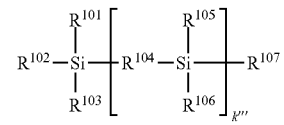

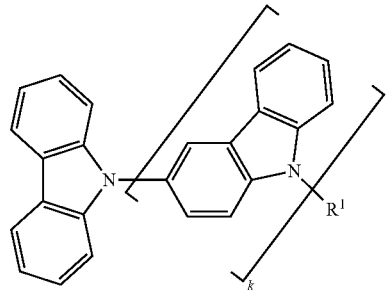

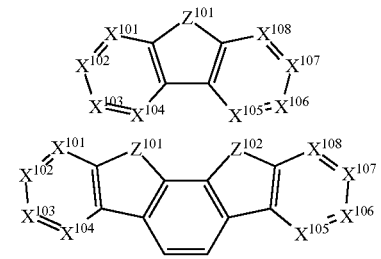

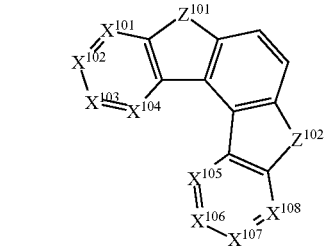

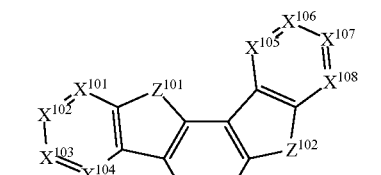

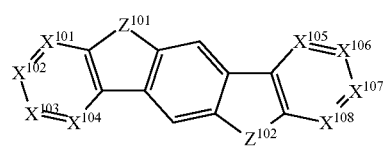

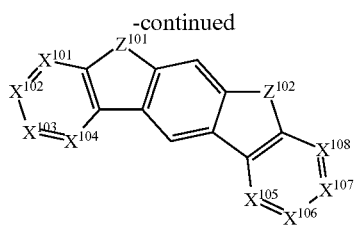

wherein R$^{101}$ to R$^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 1 to 20; k''' is an integer from 0 to 20. X$^{101}$ to X$^{108}$ is selected from C (including CH) or N. Z$^{101}$ and Z$^{102}$ is selected from NR$^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

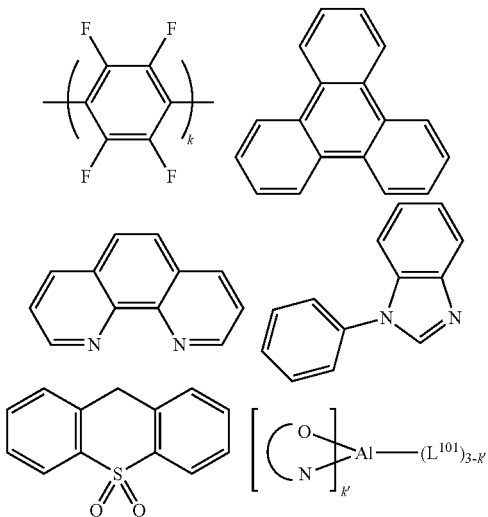

k is an integer from 1 to 20; L$^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

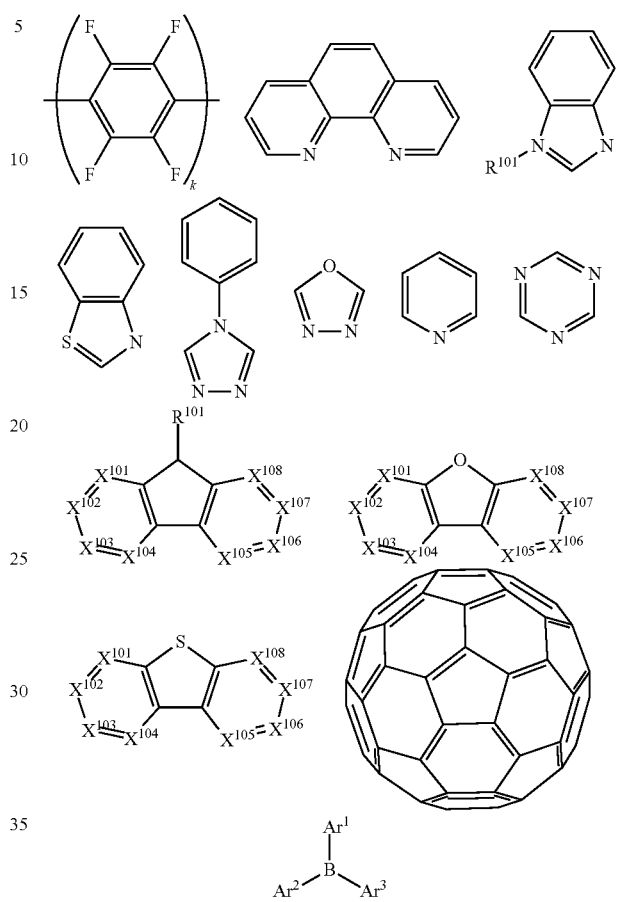

wherein R$^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. Ar$^1$ to Ar$^3$ has the similar definition as Ar's mentioned above. k is an integer from 1 to 20. X$^{101}$ to X$^{108}$ is selected from C (including CH) or N.

In another aspect, the metal complexes used in ETL contains, but not limit to the following general formula:

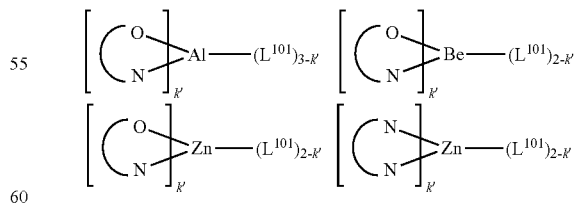

(O—N) or (N—N) is a bidentate ligand, having metal coordinated to atoms O, N or N, N; L$^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table XXX below. Table XXX lists non-limiting classes of materials, non-limiting examples of compounds for each class, and references that disclose the materials.

TABLE 5

| MATERIAL | EXAMPLES OF MATERIAL | PUBLICATIONS |
|---|---|---|
| Hole injection materials | | |
| Phthalocyanine and porphryin compounds | 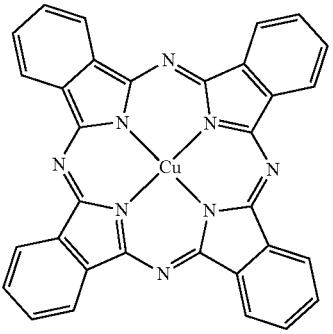 | Appl. Phys. Lett. 69, 2160 (1996) |
| Starburst triarylamines | 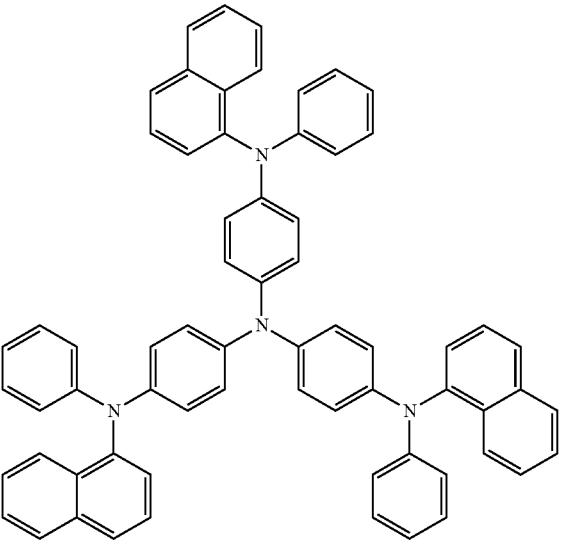 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| CF$_x$ Fluorohydrocarbon polymer | $-\!\!+\!\mathrm{CH_xF_y}\!+\!\!-_n$ | Appl. Phys. Lett. 78, 673 (2001) |
| Conducting polymers (e.g., PEDOT:PSS, polyaniline, polypthiophene) | 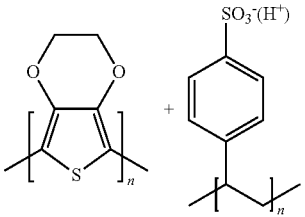 | Synth. Met. 87, 171 (1997) WO2007002683 |
| Phosphonic acid and sliane SAMs | 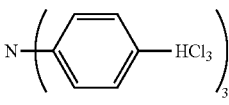 | US20030162053 |

TABLE 5-continued

| MATERIAL | EXAMPLES OF MATERIAL | PUBLICATIONS |
|---|---|---|
| Triarylamine or polythiophene polymers with conductivity dopants | 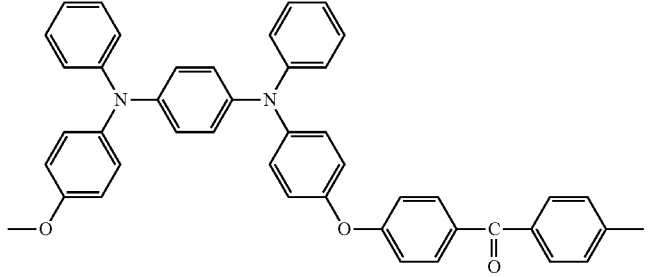 | EP1725079A1 |
| | 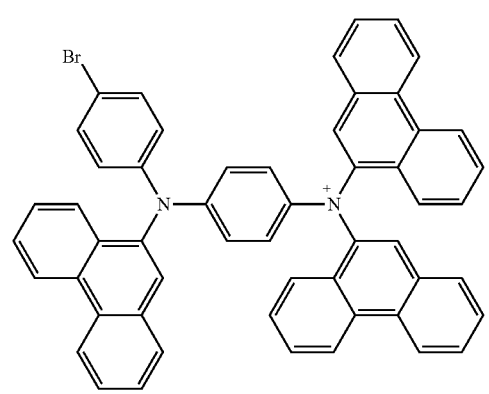 [SMILES: Brc1ccc(N(c2ccc(N(c3cc4ccccc4c4ccccc34)c3cc4ccccc4c4ccccc34)cc2)c2cc3ccccc3c3ccccc23)cc1] | |
| Organic compounds with conductive inorganic compounds, such as molybdenum and tungsten oxides | 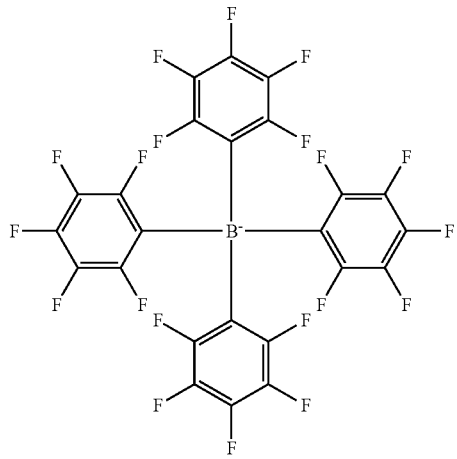 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | US20050123751<br>SID Symposium Digest, 37, 923 (2006)<br>WO2009018009 |
| n-type semiconducting organic complexes | | US20020158242 |
| Metal organometallic complexes | | US20060240279 |
| Cross-linkable compounds | | US20080220265 |

TABLE 5-continued

| MATERIAL | EXAMPLES OF MATERIAL | PUBLICATIONS |
| --- | --- | --- |
| Polythiophene based polymers and copolymers | | WO 2011075644<br>EP2350216 |
| Hole transporting materials | | |
| Triarylamines<br>(e.g., TPD, α-NPD) | | Appl. Phys. Lett. 51, 913 (1987) |
| | | U.S. Pat. No. 5,061,569 |
| | | EP650955 |

TABLE 5-continued
| MATERIAL | EXAMPLES OF MATERIAL | PUBLICATIONS |
|---|---|---|
| | 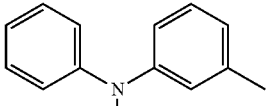 | J. Mater. Chem. 3, 319 (1993) |
| | 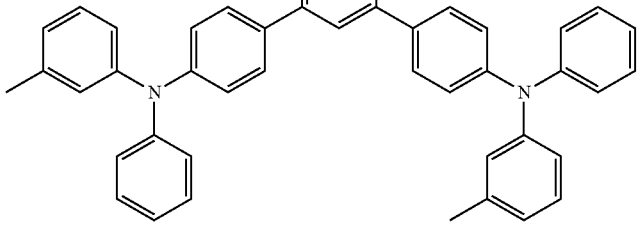 | Appl. Phys. Lett. 90, 183503 (2007) |
| | 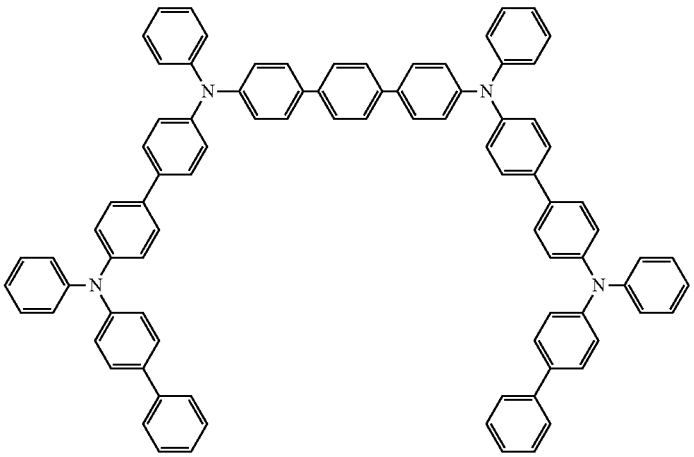 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| Triaylamine on spirofluorene core | 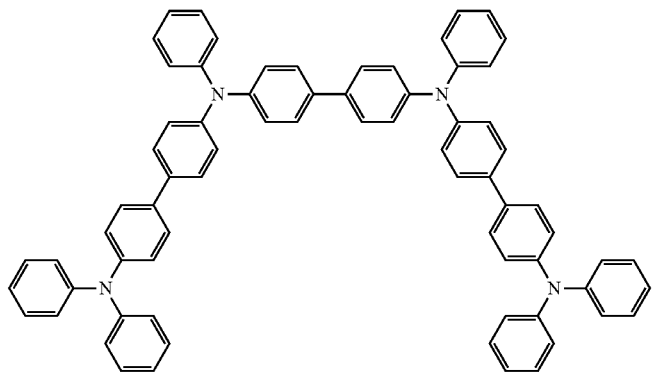 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Synth. Met. 91, 209 (1997) |

TABLE 5-continued

| MATERIAL | EXAMPLES OF MATERIAL | PUBLICATIONS |
| --- | --- | --- |
| Arylamine carbazole compounds | | Adv. Mater. 6, 677 (1994), US20080124572 |
| Triarylamine with (di)benzothiophene/(di)benzofuran | | US20070278938, US20080106190 US20110163302 |
| Indolocarbazoles | | Synth. Met. 111, 421 (2000) |
| Isoindole compounds | | Chem. Mater. 15, 3148 (2003) |

TABLE 5-continued

| MATERIAL | EXAMPLES OF MATERIAL | PUBLICATIONS |
| --- | --- | --- |
| Metal carbene complexes | | US20080018221 |

Phosphorescent OLED host materials

Red hosts

| | | |
| --- | --- | --- |
| Arylcarbazoles | | Appl. Phys. Lett. 78, 1622 (2001) |
| Metal 8-hydroxyquinolates (e.g., Alq3, BAlq) | | Nature 395, 151 (1998) |
| | | US20060202194 |
| | | WO2005014551 |
| | | WO2006072002 |

TABLE 5-continued

| MATERIAL | EXAMPLES OF MATERIAL | PUBLICATIONS |
| --- | --- | --- |
| Metal phenoxybenzothiazole compounds | | Appl. Phys. Lett. 90, 123509 (2007) |
| Conjugated oligomers andpolymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
| --- | --- | --- |
| Arylcarbazoles | | Appl. Phys. Lett. 78, 1622 (2001) |

TABLE 5-continued
| MATERIAL | EXAMPLES OF MATERIAL | PUBLICATIONS |
|---|---|---|
| | 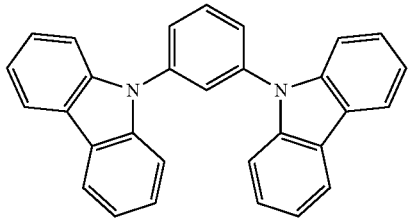 [SMILES: c1cc(-n2c3ccccc3c3ccccc32)cc(-n2c3ccccc3c3ccccc32)c1] | US20030175553 |
| | 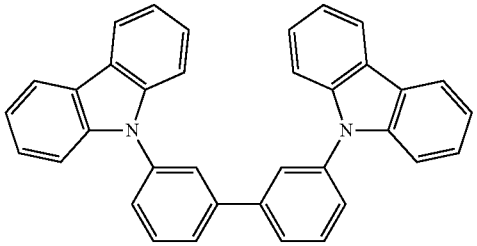 [SMILES: c1cc(-c2cccc(-n3c4ccccc4c4ccccc43)c2)cc(-n2c3ccccc3c3ccccc32)c1] | WO2001039234 |
| Aryltriphenylene compounds | 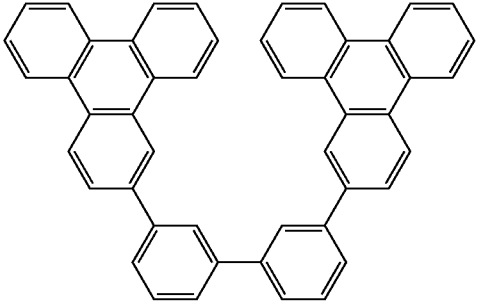 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 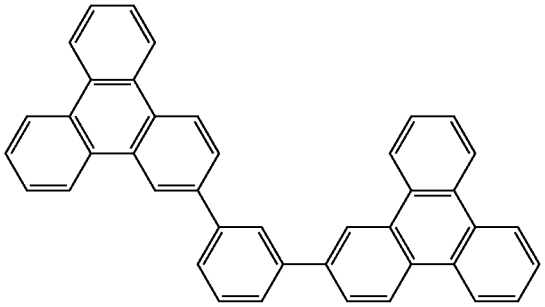 [SMILES: c1cc(-c2ccc3c4ccccc4c4ccccc4c3c2)cc(-c2ccc3c4ccccc4c4ccccc4c3c2)c1] | US20060280965 |
| | 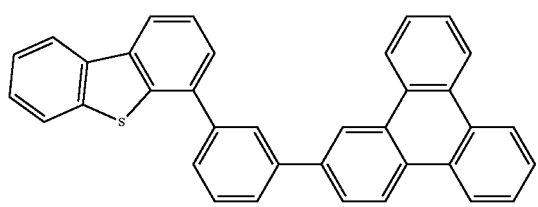 | WO2009021126 |

TABLE 5-continued
| MATERIAL | EXAMPLES OF MATERIAL | PUBLICATIONS |
|---|---|---|
| Poly-fused heteroaryl compounds | 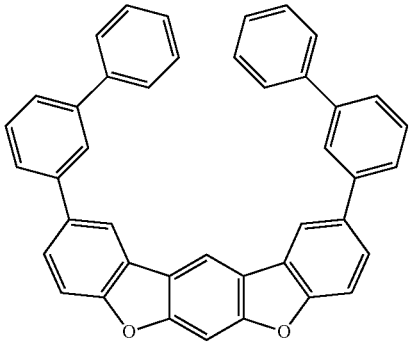 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 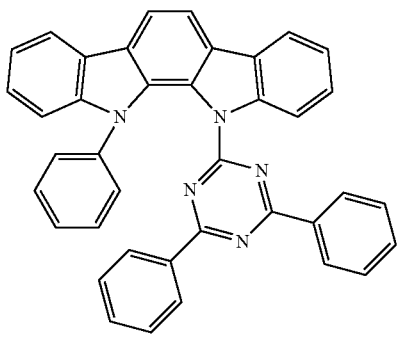 [SMILES: c1ccc(-c2nc(-c3ccccc3)nc(-n3c4ccccc4c4ccc5c6ccccc6n(-c6ccccc6)c5c43)n2)cc1] | WO2008056746 |
|  | 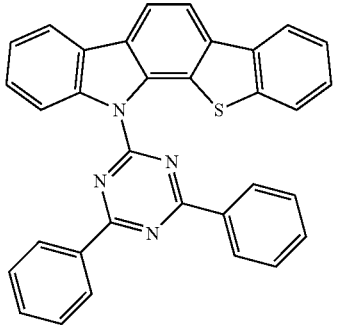 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 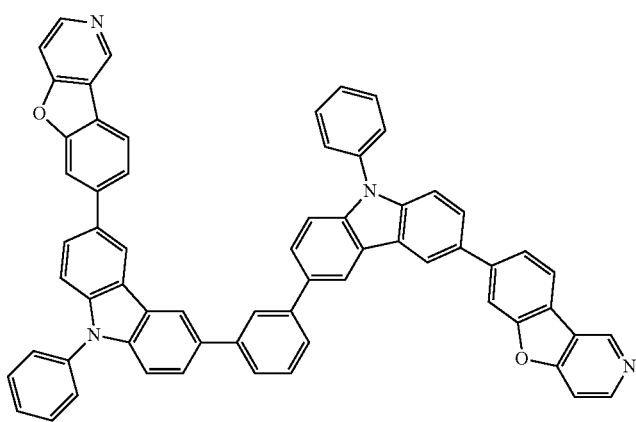 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

TABLE 5-continued

| MATERIAL | EXAMPLES OF MATERIAL | PUBLICATIONS |
| --- | --- | --- |
| | | US20100187984 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |
| | | WO2006132173 |
| | | JP200511610 |

TABLE 5-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |

TABLE 5-continued

| MATERIAL | EXAMPLES OF MATERIAL | PUBLICATIONS |
|---|---|---|
| | | WO2004107822 |
| Tetraphenylene complexes | | US20050112407 |
| Metal phenoxypyridine compounds | | WO2005030900 |
| Metal coordination complexes (e.g., Zn, Al with N^N ligands) | | US20040137268, US20040137267 |

Blue hosts

| | | |
|---|---|---|
| Arylcarbazoles | | Appl. Phys. Lett, 82, 2422 (2003) |

| MATERIAL | EXAMPLES OF MATERIAL | PUBLICATIONS |
|---|---|---|
| | 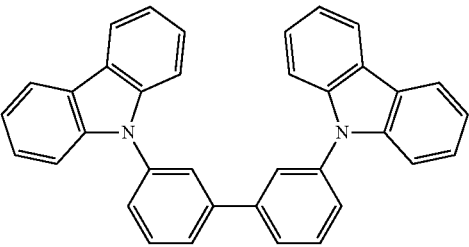 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran-carbazole compounds | 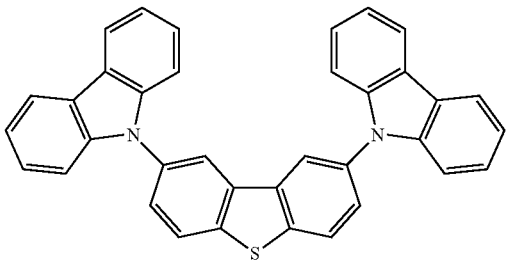 [SMILES: c1ccc2c(c1)c1ccccc1n2-c1ccc2sc3ccc(-n4c5ccccc5c5ccccc54)cc3c2c1] | WO2006114966, US20090167162 |
| | 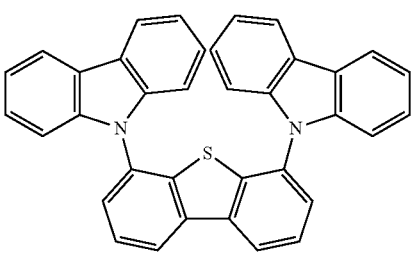 [SMILES: c1cc(-n2c3ccccc3c3ccccc32)c2sc3c(-n4c5ccccc5c5ccccc54)cccc3c2c1] | US20090167162 |
| | 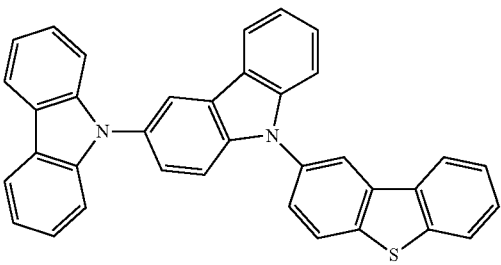 [SMILES: c1ccc2c(c1)sc1ccc(-n3c4ccccc4c4cc(-n5c6ccccc6c6ccccc65)ccc43)cc12] | WO2009086028 |
| | 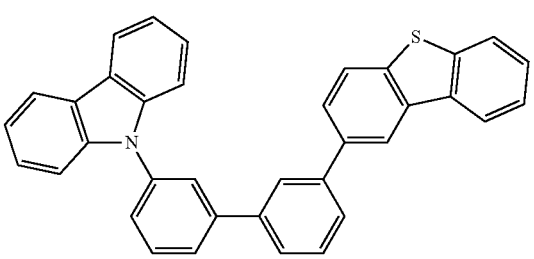 [SMILES: c1cc(-c2cccc(-n3c4ccccc4c4ccccc43)c2)cc(-c2ccc3sc4ccccc4c3c2)c1] | US20090030202, US20090017330 |
| | 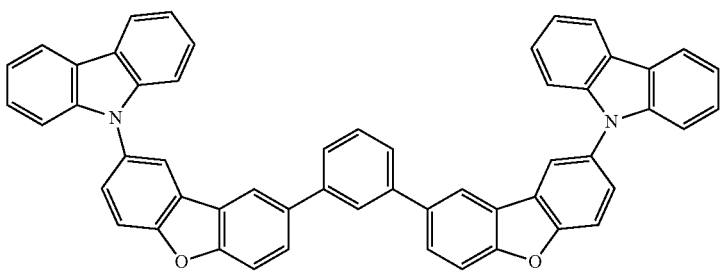 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |

TABLE 5-continued
| MATERIAL | EXAMPLES OF MATERIAL | PUBLICATIONS |
|---|---|---|
| Silicon aryl compounds | 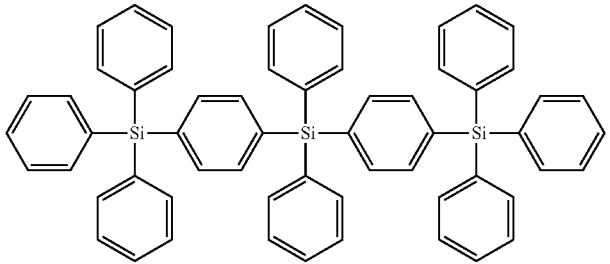 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 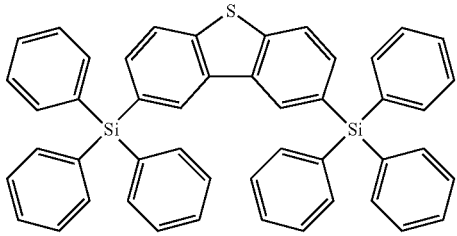 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 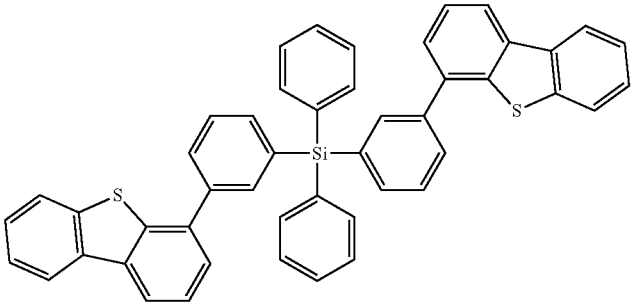 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 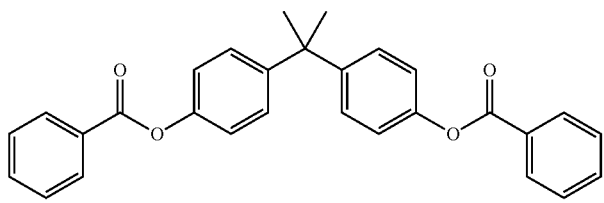 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 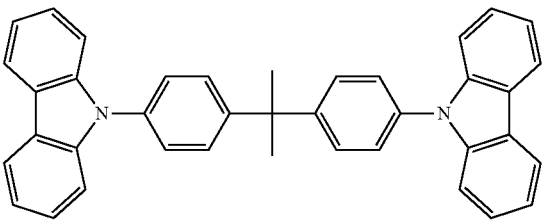 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 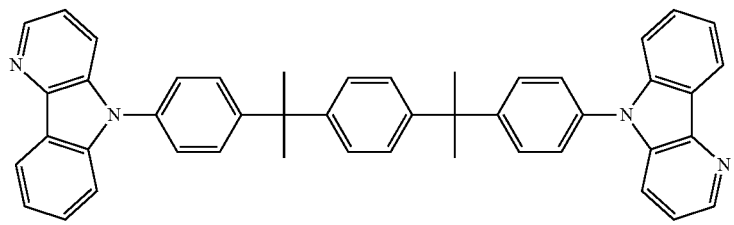 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE 5-continued

| MATERIAL | EXAMPLES OF MATERIAL | PUBLICATIONS |
| --- | --- | --- |
| High triplet metal organometallic complex | [structure] | U.S. Pat No. 7,154,114 |

Phosphorescent dopants
Red dopants

| | | |
| --- | --- | --- |
| Heavy metal porphyrins (e.g., PtOEP) | [structure] | Nature 395, 151 (1998) |
| Iridium (III) organometallic complexes | [structure] | Appl. Phys. Lett. 78, 1622 (2001) |
| | [structure] | US2006835469 |
| | [structure] | US2006835469 |

TABLE 5-continued

| MATERIAL | EXAMPLES OF MATERIAL | PUBLICATIONS |
|---|---|---|
| | | US20060202194 |
| | | US20060202194 |
| | | US20070087321 |
| | | US20080261076<br>US20100090591 |
| | | US20070087321 |

TABLE 5-continued

| MATERIAL | EXAMPLES OF MATERIAL | PUBLICATIONS |
|---|---|---|
| | | Adv. Mater. 19, 739 (2007) |
| | | WO2009100991 |
| | | WO2008101842 |
| | | U.S. Pat. No. 7,232,618 |
| Platinum (II) organometallic complexes | | WO2003040257 |

TABLE 5-continued
| MATERIAL | EXAMPLES OF MATERIAL | PUBLICATIONS |
|---|---|---|
| | 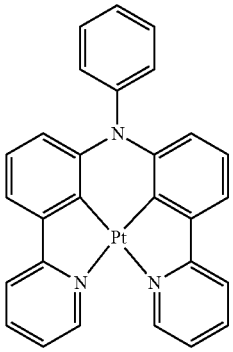 | US20070103060 |
| Osminum (III) complexes | 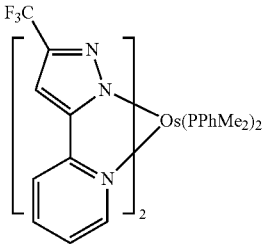 | Chem. Mater. 17, 3532 (2005) |
| Ruthenium (II) complexes | 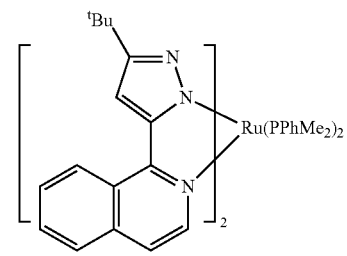 | Adv. Mater. 17, 1059 (2005) |
| Rhenium (I), (II), and (III) complexes | | US20050244673 |
Green dopants
| Iridium (III) organometallic complexes | 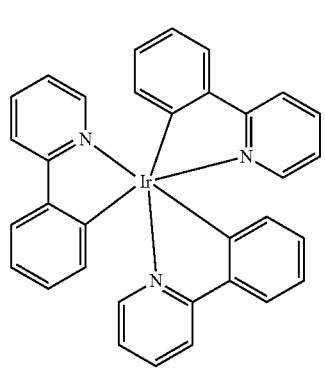
and its derivatives | Inorg. Chem. 40, 1704 (2001) |

TABLE 5-continued
| MATERIAL | EXAMPLES OF MATERIAL | PUBLICATIONS |
|---|---|---|
| | 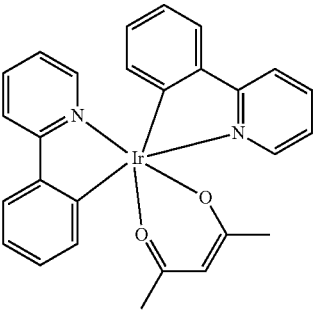 | US20020034656 |
| | 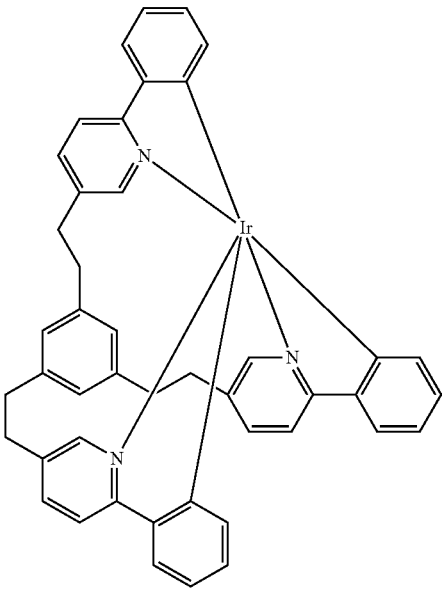 | U.S. Pat. No. 7,332,232 |
| | 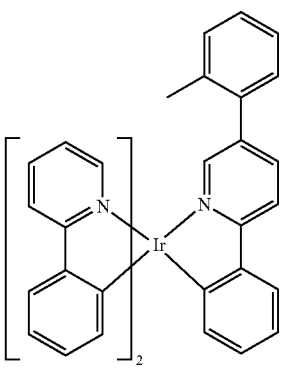 | US20090108737<br>WO2010028151 |

TABLE 5-continued

| MATERIAL | EXAMPLES OF MATERIAL | PUBLICATIONS |
|---|---|---|
| | | EP1841834B |
| | | US20060127696 |
| | | US20090039776 |
| | | U.S. Pat. No. 6,921,915 |
| | | US20100244004 |

TABLE 5-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US 20060008670 JP2007123392 |
| | | WO2010086089, WO2011044988 |
| | | Adv. Mater. 16, 2003 (2004) |

TABLE 5-continued
| MATERIAL | EXAMPLES OF MATERIAL | PUBLICATIONS |
|---|---|---|
|  | 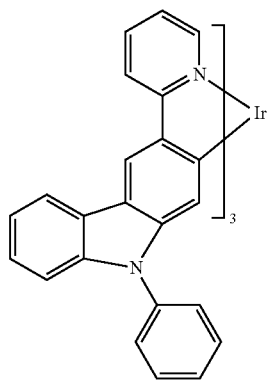 | Angew. Chem. Int. Ed. 2006, 45, 7800 |
|  | 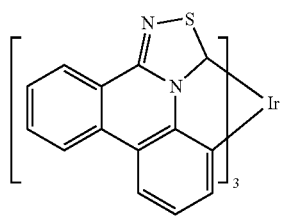 | WO2009050290 |
|  | 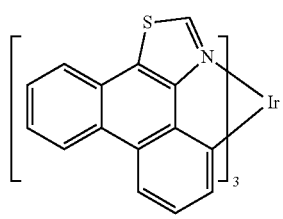 | US20090165846 |
|  | 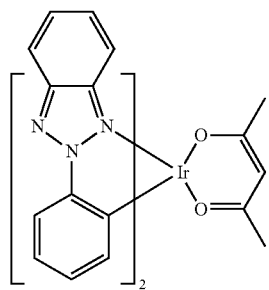 | US20080015355 |
|  | 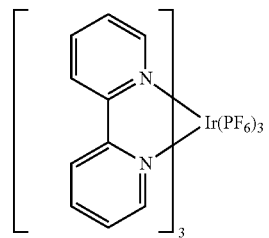 | US20010015432 |
|  | 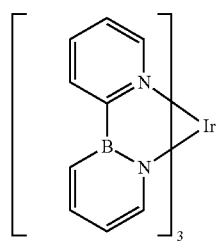 | US20100295032 |

| MATERIAL | EXAMPLES OF MATERIAL | PUBLICATIONS |
| --- | --- | --- |
| Monomer for polymeric metal organometallic compounds | | U.S. Pat. No. 7,250,226, U.S. Pat. No. 7,396,598 |
| Pt (II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 5-continued

| MATERIAL | EXAMPLES OF MATERIAL | PUBLICATIONS |
|---|---|---|
| | | US20060263635 |
| | | US20060182992<br>US20070103060 |
| Cu complexes | | WO2009000673 |
| | | US20070111026 |

TABLE 5-continued
| MATERIAL | EXAMPLES OF MATERIAL | PUBLICATIONS |
|---|---|---|
| Gold complexes | 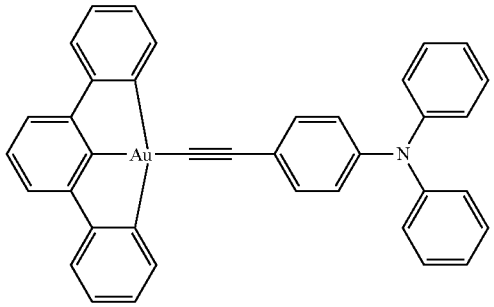 | Chem. Commun. 2906 (2005) |
| Rhenium (III) complexes | 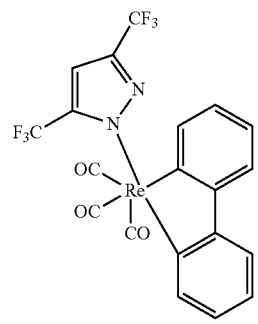 | Inorg. Chem. 42, 1248 (2003) |
| Osmium (II) complexes | | U.S. Pat. No. 7,279,704 |
| Deuterated organometallic complexes | | US20030138657 |
| Organometallic complexes with two or more metal centers | 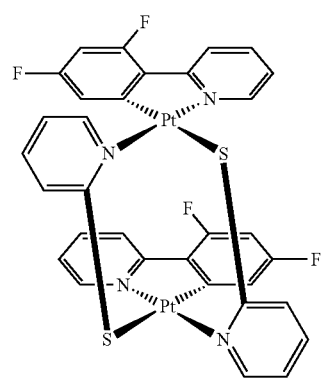 | US20030152802<br><br>U.S. Pat. No. 7,090,928 |
| Blue dopants | | |
| Iridium (III) organometallic complexes | 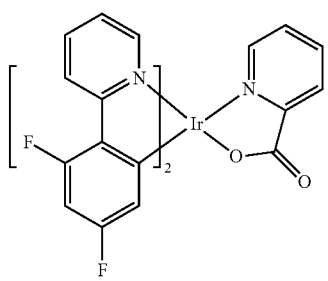 | WO2002002714 |

TABLE 5-continued

| MATERIAL | EXAMPLES OF MATERIAL | PUBLICATIONS |
|---|---|---|
| | | WO2006009024 |
| | | US20060251923<br>US20110057559<br>US20110204333 |
| | | U.S. Pat. No. 7,393,599,<br>WO2006056418,<br>US20050260441,<br>WO2005019373 |
| | | U.S. Pat. No. 7,534,505 |
| | | WO2011051404 |
| | | U.S. Pat. No. 7,445,855 |

TABLE 5-continued

| MATERIAL | EXAMPLES OF MATERIAL | PUBLICATIONS |
|---|---|---|
| | | US20070190359, US20080297033 US20100148663 |
| | | U.S. Pat. No. 7,338,722 |
| | | US20020134984 |
| | | Angew. Chem. Int. Ed. 47, 1 (2008) |
| | | Chem. Mater. 18, 5119 (2006) |

TABLE 5-continued
| MATERIAL | EXAMPLES OF MATERIAL | PUBLICATIONS |
|---|---|---|
| | 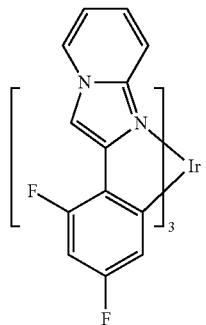 | Inorg. Chem. 46, 4308 (2007) |
| | 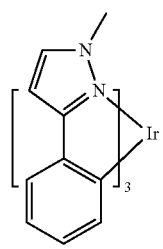 | WO2005123873 |
| | 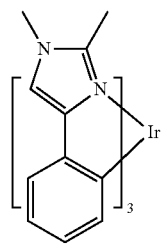 | WO2005123873 |
| | 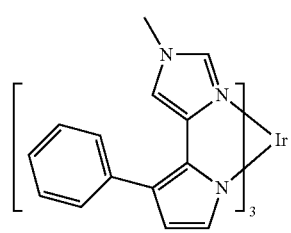 | WO2007004380 |
| | 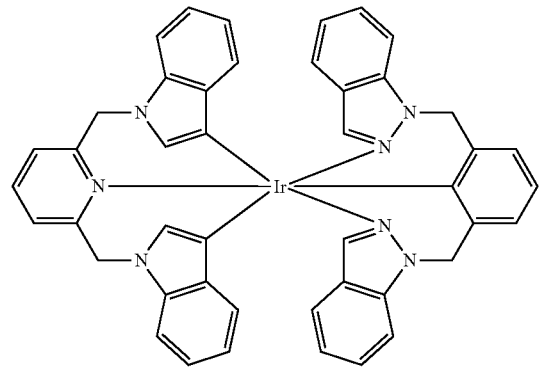 | WO2006082742 |

| MATERIAL | EXAMPLES OF MATERIAL | PUBLICATIONS |
|---|---|---|
| Osmium (II) complexes | 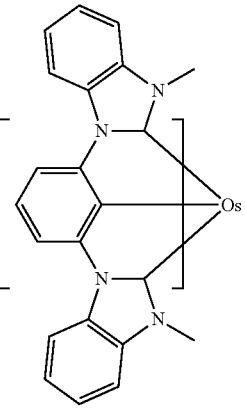 | U.S. Pat. No. 7,279,704 |
| | 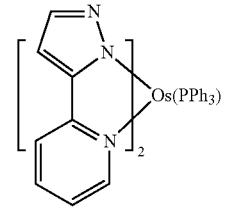 | Organometallics 23, 3745 (2004) |
| Gold complexes | 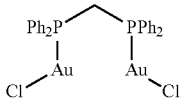 | Appl. Phys. Lett. 74, 1361 (1999) |
| Platinum (II) complexes | 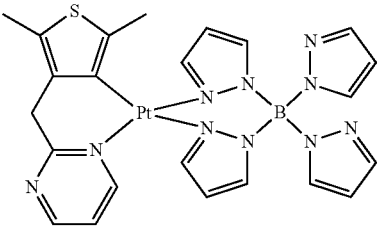 | WO2006098120, WO2006103874 |
| Pt tetradentate complexes with at least one metal-carbene bond | 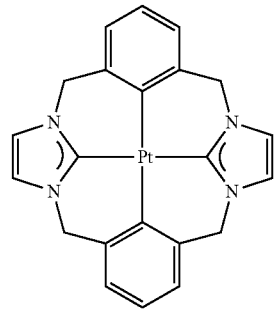 | U.S. Pat. No. 7,655,323 |
| Exciton/hole blocking layer materials | | |
| Bathocuprine compounds (e.g., BCP, BPhen) | 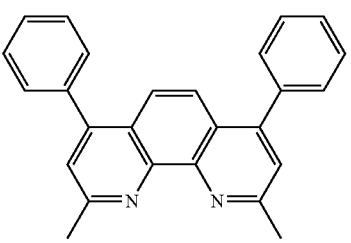 [SMILES: Cc1cc(-c2ccccc2)c2ccc3c(-c4ccccc4)cc(C)nc3c2n1] | Appl. Phys. Lett. 75, 4 (1999) |

TABLE 5-continued
| MATERIAL | EXAMPLES OF MATERIAL | PUBLICATIONS |
|---|---|---|
| | 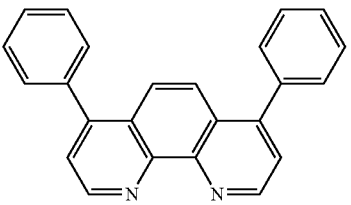 [SMILES: c1ccc(-c2ccnc3c2ccc2c(-c4ccccc4)ccnc23)cc1] | Appl. Phys. Lett. 79, 449 (2001) |
| Metal 8-hydroxy-quinolates (e.g., BAlq) | 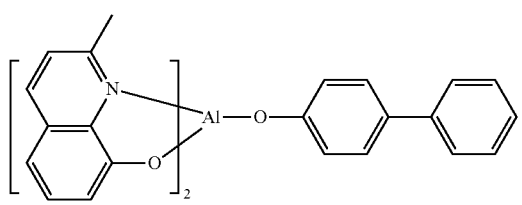 | Appl. Phys. Lett. 81, 162 (2002) |
| 5-member ring electron deficient heterocycles such as triazole, oxadiazole, imidazole, benzoimidazole | 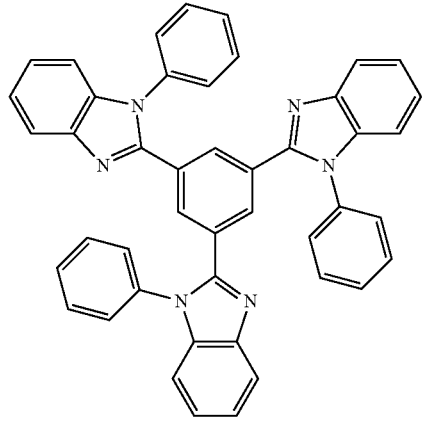 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 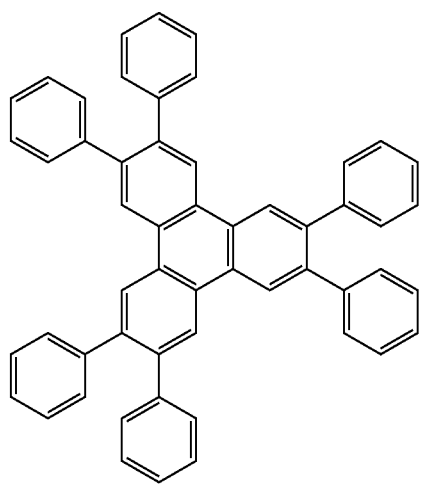 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 5-continued
| MATERIAL | EXAMPLES OF MATERIAL | PUBLICATIONS |
|---|---|---|
| Fluorinated aromatic compounds | 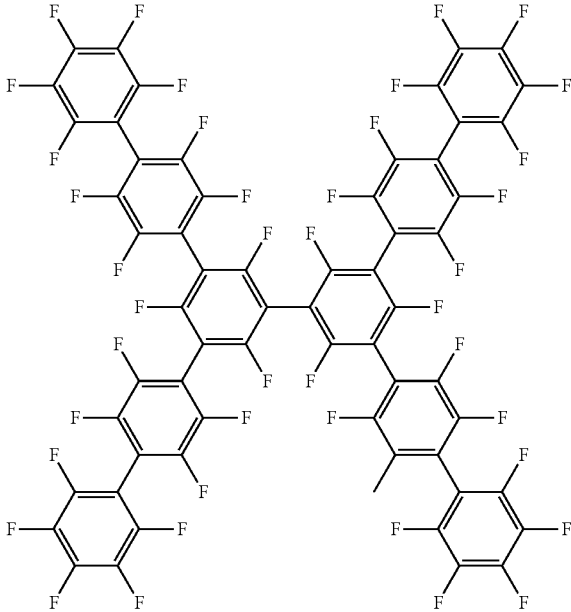 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 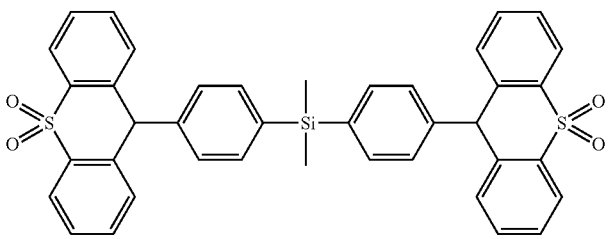 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 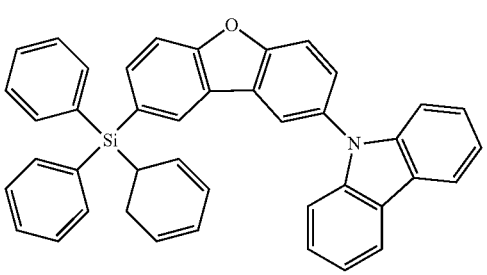 [SMILES: C1=CCC([Si](c2ccccc2)(c2ccccc2)c2ccc3oc4ccc(-n5c6ccccc6c6ccccc65)cc4c3c2)C=C1] | WO2010079051 |

TABLE 5-continued
| MATERIAL | EXAMPLES OF MATERIAL | PUBLICATIONS |
|---|---|---|
| Aza-carbazoles | 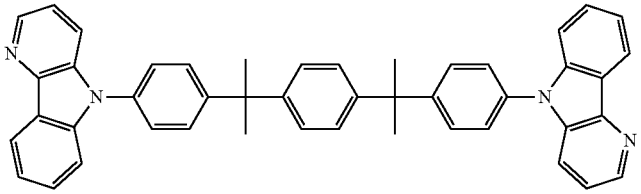 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 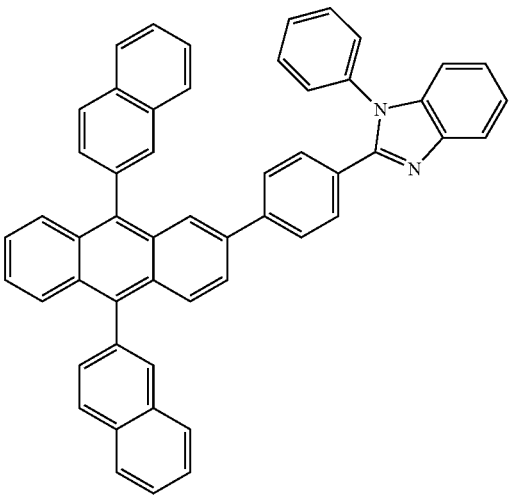 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | | US20090179554 |
| Aza triphenylene derivatives | 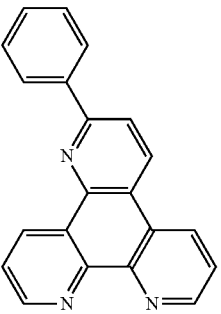 [SMILES: c1ccc(-c2ccc3c4cccnc4c4ncccc4c3n2)cc1] | US20090115316 |
| Anthracene-benzothiazole compounds | 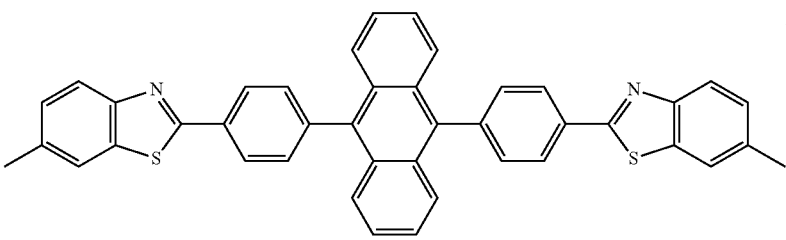 | Appl. Phys. Lett. 89, 063504 (2006) |
| Metal 8-hydroxyquinolates (e.g., Alq3, Zrq4) | 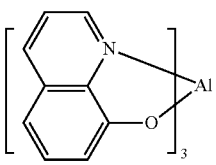 | Appl. Phys. Lett. 51, 913 (1987)<br>U.S. Pat. No. 7,230,107 |

TABLE 5-continued

| MATERIAL | EXAMPLES OF MATERIAL | PUBLICATIONS |
|---|---|---|
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 5-continued
| MATERIAL | EXAMPLES OF MATERIAL | PUBLICATIONS |
|---|---|---|
| Silole compounds | 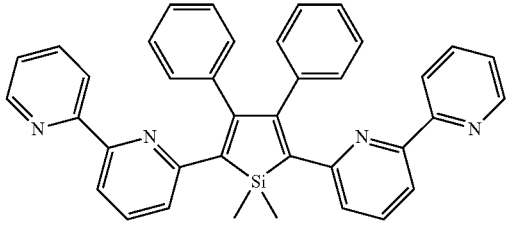 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 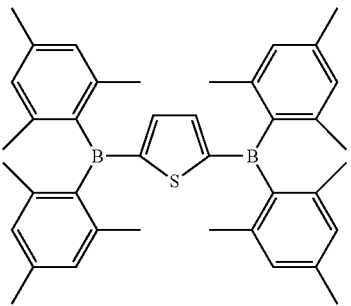 | J. Am. Chem. Soc. 120, 9714 (1998) |
| Fluorinated aromatic compounds | 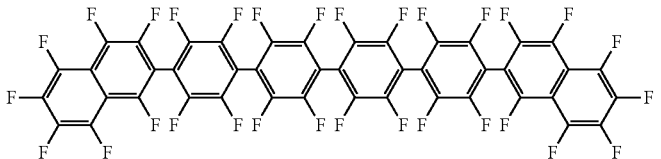 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 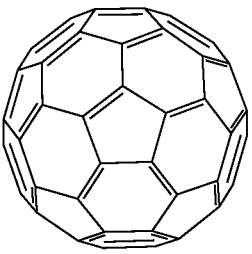 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 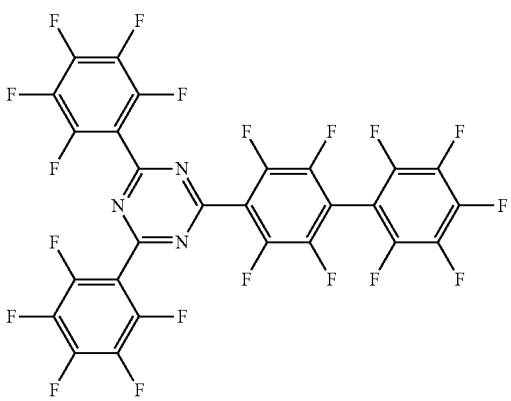 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

| MATERIAL | EXAMPLES OF MATERIAL | PUBLICATIONS |
|---|---|---|
| Zn (N^N) complexes | | U.S. Pat. No. 6,528,187 |

EXPERIMENTAL

Exemplary Material Synthesis

All reactions were carried out under nitrogen atmosphere unless specified otherwise. All solvents for reactions are anhydrous and used as received from commercial sources.

Synthesis of Compound 2 (C-2)

Compound 2

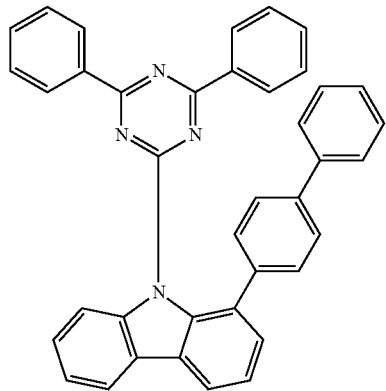

Synthesis of 1-bromo-9-(4,6-diphenyl-1,3,5-triazin-2-yl)-9H-carbazole

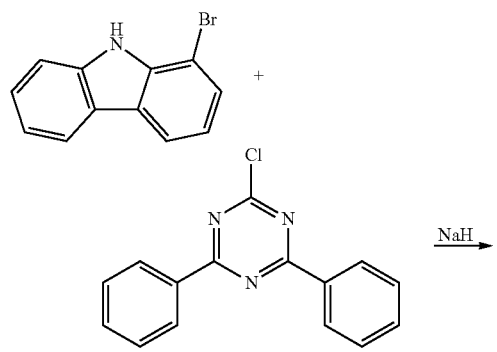

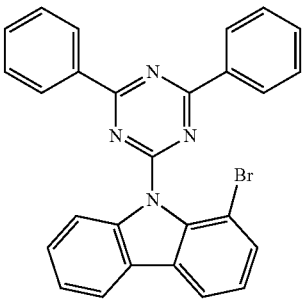

1-Bromo-9H-carbazole (1.0 g, 4.06 mmol) was dissolved in DMF (20 ml). Sodium hydride (0.146 g, 6.10 mmol, 60% dispersion in mineral oil) was then added to the solution and it immediately turned yellow with some bubbling. After 1 h of stirring at room temperature, 2-chloro-4,6-diphenyl-1,3,5-triazine (1.63 g, 6.10 mmol) was added in one portion. The reaction was allowed to stir at room temperature for 2 days before adding 100 mL of water to quench the reaction. The precipitate was collected by filtration, solubilized in DCM and coated on Celite to purify by column chromatography on silica gel eluted with 25% of dichloromethane (DCM) in heptanes. Because of some solubility issues, the separation was not efficient. After evaporating of the solvent, the solid was triturated in EtOH 2 times to afford 1-bromo-9-(4,6-diphenyl-1,3,5-triazin-2-yl)-9H-carbazole (1.5 g, 77% yield) as a white powder.

Synthesis of Compound 2

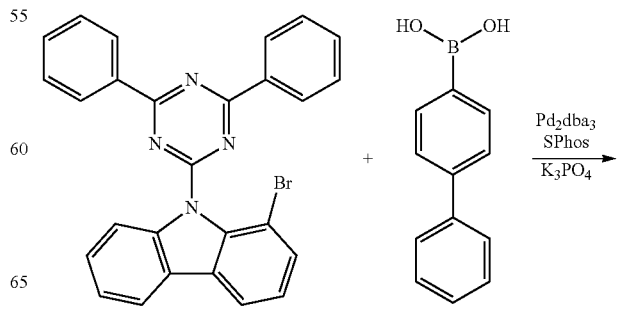

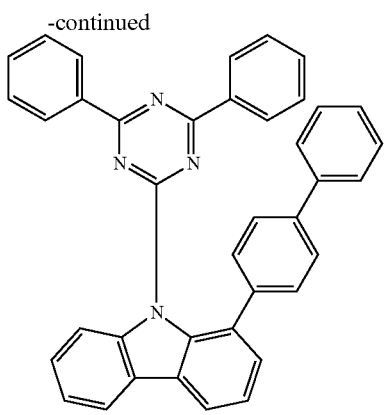

[1,1'-Biphenyl]-4-ylboronic acid (3.11 g, 15.71 mmol), 1-bromo-9-(4,6-diphenyl-1,3,5-triazin-2-yl)-9H-carbazole (3.75 g, 7.86 mmol), and anhydrous potassium phosphate (4.17 g, 19.64 mmol) were mixed with 50 mL of toluene and 5 mL of water. The mixture was degassed by bubbling nitrogen for 30 minutes followed by the addition of Tris(dibenzylideneacetone)dipalladium(0) ($Pd_2(dba)_3$) (0.719 g, 0.786 mmol) and dicyclohexyl(2',6'-dimethoxy-[1,1'-biphenyl]-2-yl)phosphine (SPhOS) (1.290 g, 3.14 mmol). The reaction was heated to reflux for 24 h. Thin layer chromatography (TLC) indicated the reaction goes to completion. Ethyl acetate and water were added to the mixture and the organic and aqueous layers were decanted. The aqueous layer was washed two times with ethyl acetate. The combined organic layers were washed with brine and water and dried with sodium sulfate. The crude material was coated on celite and purified by column chromatography with 15-30% gradient mixture of DCM in heptanes. After evaporation of the solvent, the solid was triturated with EtOH and then the collected solid was recrystallized from heptanes and toluene. The target, Compound 2,1-([1,1'-biphenyl]-4-yl)-9-(4,6-diphenyl-1,3,5-triazin-2-yl)-9H-carbazole (2.7 g, 62% yield) was afforded as white crystals with a good purity (99.9%).

Synthesis of Compound 30 (C-30)

Compound 30

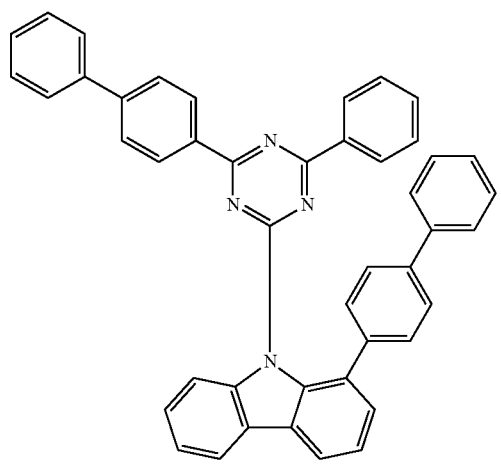

Synthesis of 9-(4-([1,1'-biphenyl]-4-yl)-6-phenyl-1,3,5-triazin-2-yl)-1-bromo-9H-carbazole

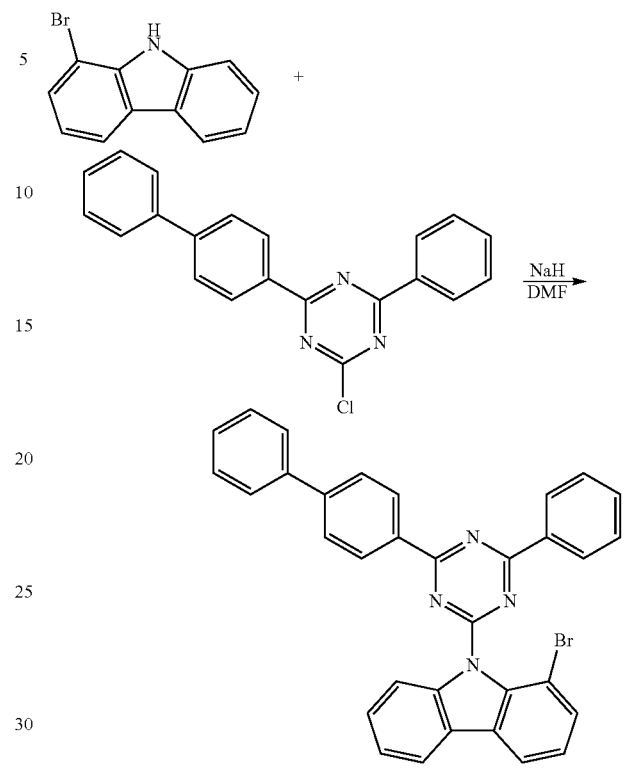

1-Bromo-9H-carbazole (2.9 g, 11.78 mmol) was dissolved in DMF (Volume: 58.9 ml) and sodium hydride (0.707 g, 17.68 mmol, 60% dispersion in mineral oil) was added to the solution, which quickly turned yellow. Once the bubbling from the reaction stopped (around 2 hours), 2-([1,1'-biphenyl]-4-yl)-4-chloro-6-phenyl-1,3,5-triazine (5.06 g, 14.73 mmol) was added as one portion. The reaction was allowed at room temperature over two days. After completion, the mixture was poured into a mixture of 25% of methanol in water. The product was extracted with DCM and washed with brine and water. The white solid was triturated from methanol one time and one more time using heptanes. The material (5.79 g, 89% yield) was approximately 90% pure and was used in the next step without further purification.

Synthesis of Compound 30

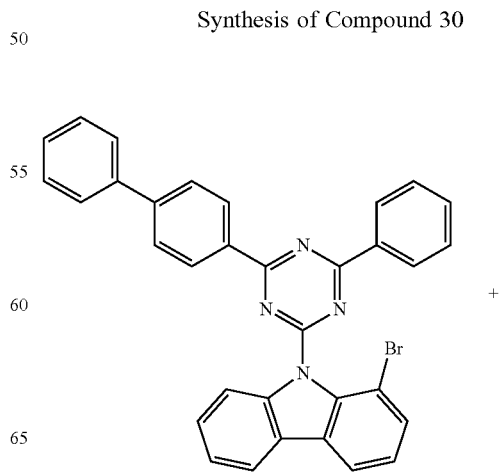

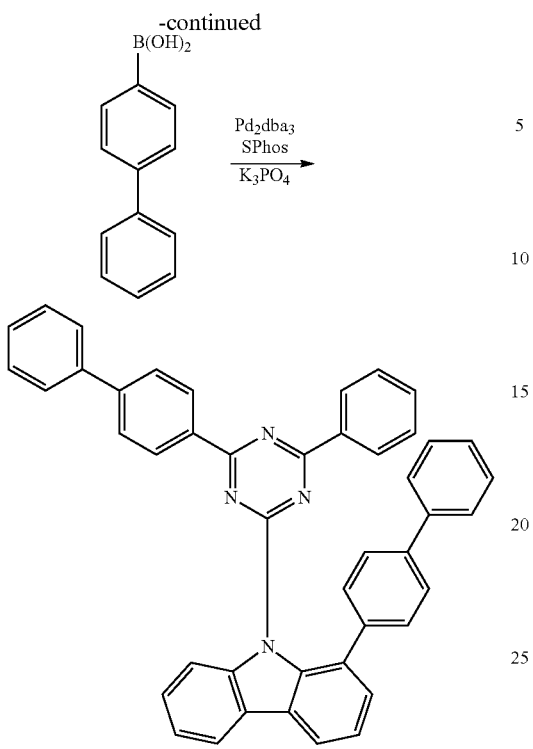

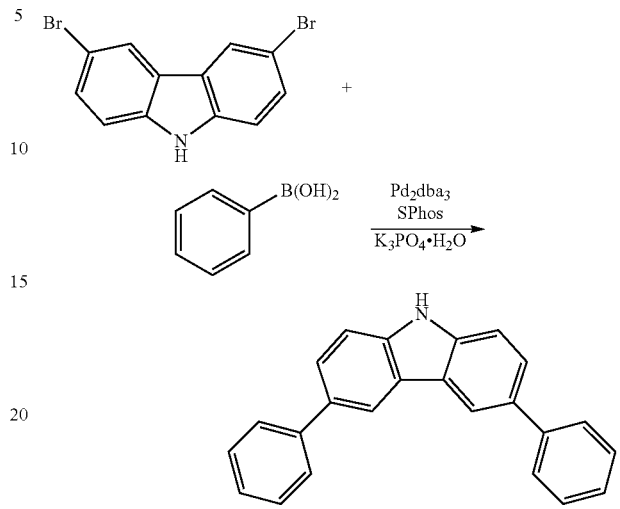

Synthesis of 3,6-diphenyl-9H-carbazole

[1,1'-Biphenyl]-4-ylboronic acid (2.86 g, 14.45 mmol), 9-(4-([1,1'-biphenyl]-4-yl)-6-phenyl-1,3,5-triazin-2-yl)-1-bromo-9H-carbazole (4.00 g, 7.23 mmol), and potassium phosphate (3.84 g, 18.07 mmol) were mixed in 50 mL of toluene and 5 mL of water. The mixture was degassed by bubbling nitrogen, followed by addition of Pd$_2$(dba)$_3$ (0.662 g, 0.723 mmol) and dicyclohexyl(2',6'-dimethoxy-[1,1'-biphenyl]-2-yl)phosphine (SPhOS) (1.187 g, 2.89 mmol). The reaction was heated to reflux for 18 h. Upon cooling down to room temperature, the mixture was extracted using ethyl acetate. The combined organic fractions were washed with brine and water. The crude material was coated on Celite and purified by column chromatography eluted with 15%-30% gradient mixture of DCM in heptanes. The powder was solubilized in DCM and i-propanol was added. The DCM was slowly evaporated out of the mixture to obtain precipitation of the target with better purity (99.6%). Then, the target material, Compound 30, was purified using column chromatography (30% DCM in Heptanes) and 1.2 g (26% yield).

3,6-Dibromo-9H-carbazole (10.0 g, 30.8 mmol), phenylboronic acid (8.25 g, 67.7 mmol) Pd$_2$(dba)$_3$ (0.564 g, 0.615 mmol), dicyclohexyl(2',6'-dimethoxy-[1,1'-biphenyl]-2-yl)phosphine (SPhOS) (1.011 g, 2.462 mmol), and potassium phosphate hydrate (28.3 g, 123 mmol) were dissolved in the mixture of toluene (350 mL) and water (40 mL) in a three-necked flask. The mixture was degassed by bubbling nitrogen, then it was heated to reflux overnight. After completion of the reaction, the mixture partitioned between ethyl acetate and water. The aqueous layer was washed 3 times with ethyl acetate and the combined organic layers were washed with brine and water. The crude compound was purified by column chromatography on silica gel, eluted with hexane/DCM 1/1 (v/v) mixture. The target compound was obtained as a white solid (7.4 g, 75% yield).

Synthesis of Comparative Compound 1 (CC-1)

Comparative compound 1

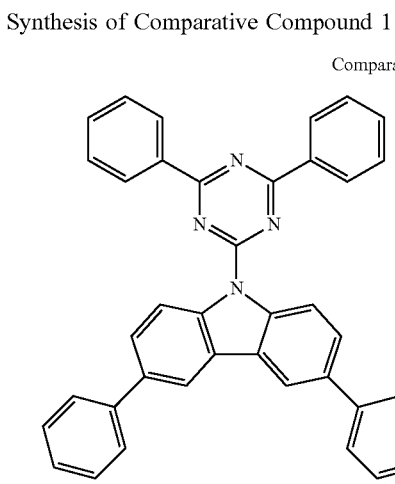

Synthesis of Comparative Compound 1

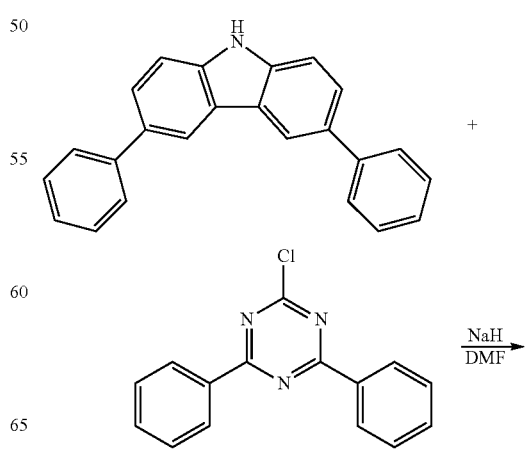

-continued

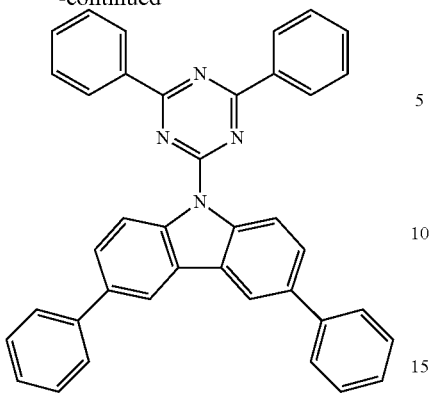

3,6-Diphenyl-9H-carbazole (4.00 g, 12.52 mmol) was dissolved in anhydrous DMF (170 mL) and treated with NaH (0.751 g, 18.79 mmol, 60% dispersion in mineral oil) while stirring vigorously at room temperature providing yellow solution. Once $H_2$ evolution stopped, the solution was stirred for 1 hour, and then treated with 2-chloro-4,6-diphenyl-1,3,5-triazine (5.03 g, 18.79 mmol), and left stirred overnight at room temperature. After stirring for ~30 minutes, reaction solution had significant white precipitate swirling around. The crude mixture was quenched with water and filtered. The white precipitate was washed with water, MeOH, and EtOH. The material was recrystallized from toluene (400 mL) to obtain the target, Comparative Compound 1 with 99.86% purity. One more recrystallization from toluene gave a purity of 100% to afford 6.0 g (87% yield).

Exemplary Devices

Material used in the devices:

TABLE 6

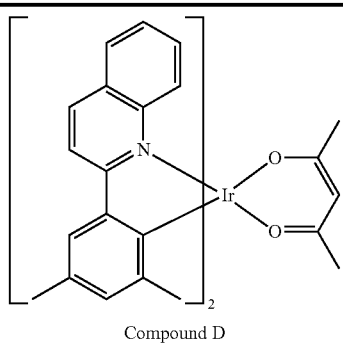

Compound D

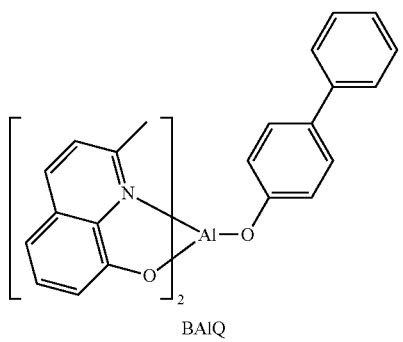

BAlQ

TABLE 6-continued

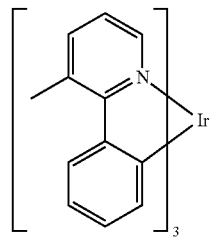

Compound SD

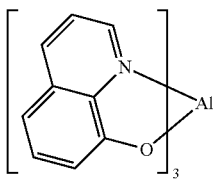

AlQ₃

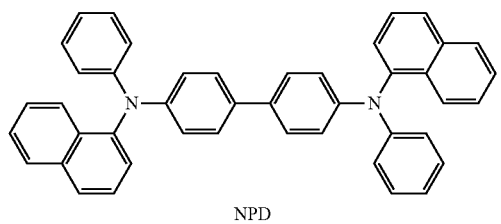 [SMILES: c1ccc(N(c2ccc(-c3ccc(N(c4ccccc4)c4cccc5ccccc45)cc3)cc2)c2cccc3ccccc23)cc1 ; "NPD"]

NPD

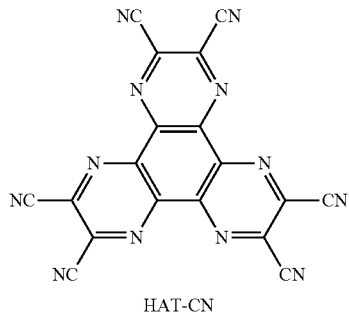 [SMILES: N#Cc1nc2c3nc(C#N)c(C#N)nc3c3nc(C#N)c(C#N)nc3c2nc1C#N]

HAT-CN

All example devices were fabricated by high vacuum ($<10^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the OLED device consisted of sequentially from the ITO surface, 100 Å of HAT-CN as the hole injection layer (HIL), 400 Å of NPD as the hole transporting layer (HTL), 300 Å of the emissive layer (EML) which contains the compound of Formula 1, Compound SD, and Compound D, 550 Å of AlQ₃ as the electron transporting layer (ETL) and 10 Å of LiF as the electron injection layer (EIL). The device structure is shown in FIG. 2.

TABLE 7

Devices structures of inventive compounds and comparative compounds

| Example | HIL | HTL | EML (300 Å, doping %) | | | BL | ETL |
|---|---|---|---|---|---|---|---|
| Example 1 | HAT-CN 100 Å | NPD 400 Å | Comparative Compound 1 79% | Compound SD, 18% | Compound D, 3% | BAlQ 50 Å | AlQ$_3$ 550 Å |
| Example 2 | HAT-CN 100 Å | NPD 400 Å | Comparative Compound 1 79% | Compound SD, 18% | Compound D, 3% | Comparative Compound 1 50 Å | AlQ$_3$ 550 Å |
| Example 3 | HAT-CN 100 Å | NPD 400 Å | Compound 2 79% | Compound SD, 18% | Compound D, 3% | BAlQ 50 Å | AlQ$_3$ 550 Å |
| Example 4 | HAT-CN 100 Å | NPD 400 Å | Compound 2 79% | Compound SD, 18% | Compound D, 3% | Compound 2 50 Å | AlQ$_3$ 550 Å |
| Example 5 | HAT-CN 100 Å | NPD 400 Å | Compound 30 88% | Compound SD, 9% | Compound D, 3% | BAlQ 50 Å | AlQ$_3$ 350 Å |

TABLE 8

VTE device results[1]

| Example | | 1931 CIE | | At 1,000 nits | | | | At 1K nits Calculated | At 80 mA/cm$^2$ | |
|---|---|---|---|---|---|---|---|---|---|---|
| | | CIE x | CIE y | Voltage [a.u.] | LE [a.u.] | EQE [a.u.] | PE [a.u.] | LT95%[2] [a.u.] | Lo [a.u.] | LT$_{95\%}$ [a.u.] |
| | Host | BL | | | | | | | | |
| Example 1 | Comparative Compound 1 | BAlQ | 0.663 | 0.336 | 1.0 | 1.0 | 1.0 | 1.0 | 1.0 | 1.0 | 1.0 |
| Example 2 | Comparative Compound 1 | Comparative Compound 1 | 0.658 | 0.340 | 0.94 | 1.1 | 1.1 | 1.2 | 1.6 | 1.1 | 1.3 |
| Esample 3 | Compound 2 | BAlQ | 0.664 | 0.335 | 0.87 | 1.2 | 1.2 | 1.4 | 3.6 | 1.1 | 2.7 |
| Example 4 | Compound 2 | Compound 2 | 0.661 | 0.338 | 0.78 | 1.2 | 1.2 | 1.6 | 4.8 | 1.2 | 3.4 |
| Example 5 | Compound 30 | BAlQ | 0.660 | 0.337 | 1.08 | 1.1 | 1.1 | 1.0 | 2.9 | 0.9 | 3.4 |

[1]All values in this table are relative numbers (arbitrary units—a.u.) except for the CIE coordinates.
[2]Calculated assuming accelerated factor: 2.0

Table 8 is a summary of the device data. The luminous efficiency (LE), external quantum efficiency (EQE) and power efficiency (PE) were measured at 1000 nits, while the lifetime (LT$_{95\%}$) was defined as the time required for the device to decay to 95% of its initial luminance under a constant current density of 40 mA/cm$^2$. Compounds such as Comparative Compound 1, which does not contain any substitution at the 1-position of the carbazole does not perform as well as Compound 2 which combines the triazine substitution on the nitrogen of the carbazole and substitution at the 1-position of the carbazole. As shown in Table 2, when the device contains Compound 2 in the emissive layer, its driving voltage is lower. Moreover, the luminous efficacy (LE), external quantum efficiency (EQE), power efficacy (PE) and operational lifetime (LT$_{95\%}$) are all improved compared to the devices which contain Comparative Compound 1 as the host. The performances are also improved when the blocking layer (BL) is Compound 2 compared to BAlQ. The best device obtained with Compound 2 (in relative numbers—compared to Comparative Compound 1) in this study showed a x value from the CIE of 0.661, a driving voltage of 0.78, an LE of 1.2, an EQE of 1.2, a PE of 1.6, and finally an LT$_{95\%}$ (measured at 1000 nits) of more than 4 times than the lifetime of the comparative example. However, performances obtained with Compound 30 are less impressive than what has been obtained with Compound 2 (Table 2). The best device obtained with Compound 30 in this study showed a x value from the CIE of 0.661, a driving voltage of 1.1, an LE of 1.1, an EQE of 1.1, a PE of 1.0, and finally an LT$_{95\%}$ (measured at 1000 nits) of almost 3 times the lifetime of the comparative example.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having a structure according to Formula I:

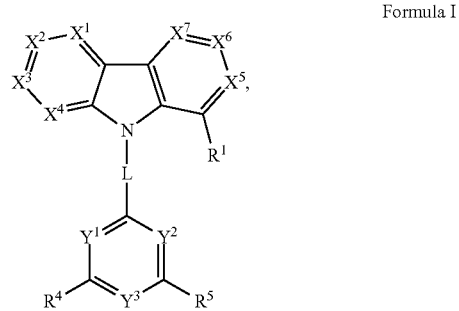

Formula I wherein $R^1$, $R^4$ and $R^5$ are independently selected from group consisting of non-fused aryl, non-fused heteroaryl, and combinations thereof;

wherein L is selected from the group consisting of a bond, non-fused aryl, non-fused heteroaryl, and combinations thereof;

wherein $X^1$, $X^2$, $X^3$, $X^4$, $X^5$, $X^6$, and $X^7$ are each CR;

wherein $Y^1$, $Y^2$, and $Y^3$ are N; and wherein each R can be same or different, and is independently selected from the group consisting of hydrogen, deuterium, non-fused aryl, non-fused heteroaryl and combinations thereof.

2. The compound of claim 1, wherein $R^1$ is selected from the group consisting of phenyl, biphenyl, terphenyl, tetraphenyl, pentaphenyl, pyridine, phenyl pyridine and pyridyl phenyl.

3. The compound of the claim 1, wherein L is selected from the group consisting of phenyl, pyridyl, biphenyl, terphenyl and a bond.

4. The compound of the claim 1, wherein $R^4$ is selected from the group consisting of phenyl, pyridyl, biphenyl, and terphenyl.

5. The compound of the claim 1, wherein $R^5$ is selected from the group consisting of phenyl, pyridyl, biphenyl, and terphenyl.

6. The compound of claim 1, wherein the compound consists of a compound having a structure according to Formula II:

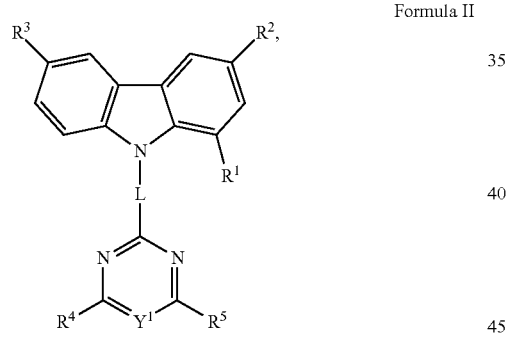

Formula II wherein $R_2$ and $R_3$ can be same or different, and independently selected from the group consisting of hydrogen, deuterium, non-fused aryl, non-fused heteroaryl and combinations thereof.

7. The compound of claim 6 wherein the compound having a structure according to Formula II is selected from the group consisting of Compound 1 through Compound 602 listed in the table below, wherein $Y^1$, $R^1$, $R^2$, $R^3$, $R^4$, $R^5$ and L are as defined and wherein C is Carbon, N is nitrogen, H is hydrogen, $A^1$ is

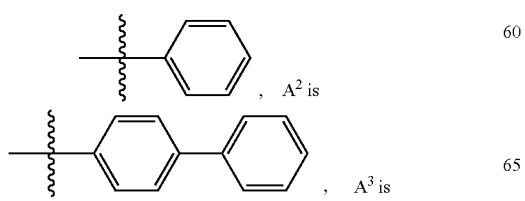

, $A^2$ is

, $A^3$ is

, $A^4$ is

, $A^5$ is

, $A^6$ is

, $A^7$ is

, and $A^8$ is

:

| Cmpd | $Y^1$ | $R^1$ | $R^2$ | $R^3$ | $R^4$ | $R^5$ | L |
|---|---|---|---|---|---|---|---|
| 1 | N | $A^1$ | H | H | $A^1$ | $A^1$ | Bond |
| 2 | N | $A^2$ | H | H | $A^1$ | $A^1$ | Bond |
| 3 | N | $A^3$ | H | H | $A^1$ | $A^1$ | Bond |
| 4 | N | $A^4$ | H | H | $A^1$ | $A^1$ | Bond |
| 5 | N | $A^5$ | H | H | $A^1$ | $A^1$ | Bond |
| 6 | N | $A^6$ | H | H | $A^1$ | $A^1$ | Bond |
| 7 | N | $A^7$ | H | H | $A^1$ | $A^1$ | Bond |
| 8 | N | $A^1$ | $A^1$ | H | $A^1$ | $A^1$ | Bond |
| 9 | N | $A^2$ | $A^1$ | H | $A^1$ | $A^1$ | Bond |
| 10 | N | $A^3$ | $A^1$ | H | $A^1$ | $A^1$ | Bond |
| 11 | N | $A^4$ | $A^1$ | H | $A^1$ | $A^1$ | Bond |
| 12 | N | $A^5$ | $A^1$ | H | $A^1$ | $A^1$ | Bond |
| 13 | N | $A^6$ | $A^1$ | H | $A^1$ | $A^1$ | Bond |
| 14 | N | $A^7$ | $A^1$ | H | $A^1$ | $A^1$ | Bond |
| 15 | N | $A^1$ | H | $A^1$ | $A^1$ | $A^1$ | Bond |
| 16 | N | $A^2$ | H | $A^1$ | $A^1$ | $A^1$ | Bond |
| 17 | N | $A^3$ | H | $A^1$ | $A^1$ | $A^1$ | Bond |
| 18 | N | $A^4$ | H | $A^1$ | $A^1$ | $A^1$ | Bond |
| 19 | N | $A^5$ | H | $A^1$ | $A^1$ | $A^1$ | Bond |
| 20 | N | $A^6$ | H | $A^1$ | $A^1$ | $A^1$ | Bond |
| 21 | N | $A^7$ | H | $A^1$ | $A^1$ | $A^1$ | Bond |
| 22 | N | $A^1$ | $A^1$ | $A^1$ | $A^1$ | $A^1$ | Bond |
| 23 | N | $A^2$ | $A^1$ | $A^1$ | $A^1$ | $A^1$ | Bond |
| 24 | N | $A^3$ | $A^1$ | $A^1$ | $A^1$ | $A^1$ | Bond |
| 25 | N | $A^4$ | $A^1$ | $A^1$ | $A^1$ | $A^1$ | Bond |
| 26 | N | $A^5$ | $A^1$ | $A^1$ | $A^1$ | $A^1$ | Bond |
| 27 | N | $A^6$ | $A^1$ | $A^1$ | $A^1$ | $A^1$ | Bond |
| 28 | N | $A^7$ | $A^1$ | $A^1$ | $A^1$ | $A^1$ | Bond |
| 29 | N | $A^1$ | H | H | $A^2$ | $A^1$ | Bond |
| 30 | N | $A^2$ | H | H | $A^2$ | $A^1$ | Bond |
| 31 | N | $A^3$ | H | H | $A^2$ | $A^1$ | Bond |
| 32 | N | $A^4$ | H | H | $A^2$ | $A^1$ | Bond |

-continued

| Cmpd | Y¹ | R¹ | R² | R³ | R⁴ | R⁵ | L |
|---|---|---|---|---|---|---|---|
| 33 | N | $A^5$ | H | H | $A^2$ | $A^1$ | Bond |
| 34 | N | $A^6$ | H | H | $A^2$ | $A^1$ | Bond |
| 35 | N | $A^7$ | H | H | $A^2$ | $A^1$ | Bond |
| 36 | N | $A^1$ | $A^1$ | H | $A^2$ | $A^1$ | Bond |
| 37 | N | $A^2$ | $A^1$ | H | $A^2$ | $A^1$ | Bond |
| 38 | N | $A^3$ | $A^1$ | H | $A^2$ | $A^1$ | Bond |
| 39 | N | $A^4$ | $A^1$ | H | $A^2$ | $A^1$ | Bond |
| 40 | N | $A^5$ | $A^1$ | H | $A^2$ | $A^1$ | Bond |
| 41 | N | $A^6$ | $A^1$ | H | $A^2$ | $A^1$ | Bond |
| 42 | N | $A^7$ | $A^1$ | H | $A^2$ | $A^1$ | Bond |
| 43 | N | $A^1$ | H | $A^1$ | $A^2$ | $A^1$ | Bond |
| 44 | N | $A^2$ | H | $A^1$ | $A^2$ | $A^1$ | Bond |
| 45 | N | $A^3$ | H | $A^1$ | $A^2$ | $A^1$ | Bond |
| 46 | N | $A^4$ | H | $A^1$ | $A^2$ | $A^1$ | Bond |
| 47 | N | $A^5$ | H | $A^1$ | $A^2$ | $A^1$ | Bond |
| 48 | N | $A^6$ | H | $A^1$ | $A^2$ | $A^1$ | Bond |
| 49 | N | $A^7$ | H | $A^1$ | $A^2$ | $A^1$ | Bond |
| 50 | N | $A^1$ | $A^1$ | $A^1$ | $A^2$ | $A^1$ | Bond |
| 51 | N | $A^2$ | $A^1$ | $A^1$ | $A^2$ | $A^1$ | Bond |
| 52 | N | $A^3$ | $A^1$ | $A^1$ | $A^2$ | $A^1$ | Bond |
| 53 | N | $A^4$ | $A^1$ | $A^1$ | $A^2$ | $A^1$ | Bond |
| 54 | N | $A^5$ | $A^1$ | $A^1$ | $A^2$ | $A^1$ | Bond |
| 55 | N | $A^6$ | $A^1$ | $A^1$ | $A^2$ | $A^1$ | Bond |
| 56 | N | $A^7$ | $A^1$ | $A^1$ | $A^2$ | $A^1$ | Bond |
| 57 | N | $A^1$ | H | H | $A^2$ | $A^2$ | Bond |
| 58 | N | $A^2$ | H | H | $A^2$ | $A^2$ | Bond |
| 59 | N | $A^3$ | H | H | $A^2$ | $A^2$ | Bond |
| 60 | N | $A^4$ | H | H | $A^2$ | $A^2$ | Bond |
| 61 | N | $A^5$ | H | H | $A^2$ | $A^2$ | Bond |
| 62 | N | $A^6$ | H | H | $A^2$ | $A^2$ | Bond |
| 63 | N | $A^7$ | H | H | $A^2$ | $A^2$ | Bond |
| 64 | N | $A^1$ | $A^1$ | H | $A^2$ | $A^2$ | Bond |
| 65 | N | $A^2$ | $A^1$ | H | $A^2$ | $A^2$ | Bond |
| 66 | N | $A^3$ | $A^1$ | H | $A^2$ | $A^2$ | Bond |
| 67 | N | $A^4$ | $A^1$ | H | $A^2$ | $A^2$ | Bond |
| 68 | N | $A^5$ | $A^1$ | H | $A^2$ | $A^2$ | Bond |
| 69 | N | $A^6$ | $A^1$ | H | $A^2$ | $A^2$ | Bond |
| 70 | N | $A^7$ | $A^1$ | H | $A^2$ | $A^2$ | Bond |
| 71 | N | $A^1$ | H | $A^1$ | $A^2$ | $A^2$ | Bond |
| 72 | N | $A^2$ | H | $A^1$ | $A^2$ | $A^2$ | Bond |
| 73 | N | $A^3$ | H | $A^1$ | $A^2$ | $A^2$ | Bond |
| 74 | N | $A^4$ | H | $A^1$ | $A^2$ | $A^2$ | Bond |
| 75 | N | $A^5$ | H | $A^1$ | $A^2$ | $A^2$ | Bond |
| 76 | N | $A^6$ | H | $A^1$ | $A^2$ | $A^2$ | Bond |
| 77 | N | $A^7$ | H | $A^1$ | $A^2$ | $A^2$ | Bond |
| 78 | N | $A^1$ | $A^1$ | $A^1$ | $A^2$ | $A^2$ | Bond |
| 79 | N | $A^2$ | $A^1$ | $A^1$ | $A^2$ | $A^2$ | Bond |
| 80 | N | $A^3$ | $A^1$ | $A^1$ | $A^2$ | $A^2$ | Bond |
| 81 | N | $A^4$ | $A^1$ | $A^1$ | $A^2$ | $A^2$ | Bond |
| 82 | N | $A^5$ | $A^1$ | $A^1$ | $A^2$ | $A^2$ | Bond |
| 83 | N | $A^6$ | $A^1$ | $A^1$ | $A^2$ | $A^2$ | Bond |
| 84 | N | $A^7$ | $A^1$ | $A^1$ | $A^2$ | $A^2$ | Bond |
| 85 | N | $A^1$ | H | H | $A^3$ | $A^1$ | Bond |
| 86 | N | $A^2$ | H | H | $A^3$ | $A^1$ | Bond |
| 87 | N | $A^3$ | H | H | $A^3$ | $A^1$ | Bond |
| 88 | N | $A^4$ | H | H | $A^3$ | $A^1$ | Bond |
| 89 | N | $A^5$ | H | H | $A^3$ | $A^1$ | Bond |
| 90 | N | $A^6$ | H | H | $A^3$ | $A^1$ | Bond |
| 91 | N | $A^7$ | H | H | $A^3$ | $A^1$ | Bond |
| 92 | N | $A^1$ | $A^1$ | H | $A^3$ | $A^1$ | Bond |
| 93 | N | $A^2$ | $A^1$ | H | $A^3$ | $A^1$ | Bond |
| 94 | N | $A^3$ | $A^1$ | H | $A^3$ | $A^1$ | Bond |
| 95 | N | $A^4$ | $A^1$ | H | $A^3$ | $A^1$ | Bond |
| 96 | N | $A^5$ | $A^1$ | H | $A^3$ | $A^1$ | Bond |
| 97 | N | $A^6$ | $A^1$ | H | $A^3$ | $A^1$ | Bond |
| 98 | N | $A^7$ | $A^1$ | H | $A^3$ | $A^1$ | Bond |
| 99 | N | $A^1$ | H | $A^1$ | $A^3$ | $A^1$ | Bond |
| 100 | N | $A^2$ | H | $A^1$ | $A^3$ | $A^1$ | Bond |
| 101 | N | $A^3$ | H | $A^1$ | $A^3$ | $A^1$ | Bond |
| 102 | N | $A^4$ | H | $A^1$ | $A^3$ | $A^1$ | Bond |
| 103 | N | $A^5$ | H | $A^1$ | $A^3$ | $A^1$ | Bond |
| 104 | N | $A^6$ | H | $A^1$ | $A^3$ | $A^1$ | Bond |
| 105 | N | $A^7$ | H | $A^1$ | $A^3$ | $A^1$ | Bond |
| 106 | N | $A^1$ | $A^1$ | $A^1$ | $A^3$ | $A^1$ | Bond |
| 107 | N | $A^2$ | $A^1$ | $A^1$ | $A^3$ | $A^1$ | Bond |
| 108 | N | $A^3$ | $A^1$ | $A^1$ | $A^3$ | $A^1$ | Bond |
| 109 | N | $A^4$ | $A^1$ | $A^1$ | $A^3$ | $A^1$ | Bond |
| 110 | N | $A^5$ | $A^1$ | $A^1$ | $A^3$ | $A^1$ | Bond |
| 111 | N | $A^6$ | $A^1$ | $A^1$ | $A^3$ | $A^1$ | Bond |
| 112 | N | $A^7$ | $A^1$ | $A^1$ | $A^3$ | $A^1$ | Bond |
| 113 | N | $A^1$ | H | H | $A^3$ | $A^3$ | Bond |
| 114 | N | $A^2$ | H | H | $A^3$ | $A^3$ | Bond |
| 115 | N | $A^3$ | H | H | $A^3$ | $A^3$ | Bond |
| 116 | N | $A^4$ | H | H | $A^3$ | $A^3$ | Bond |
| 117 | N | $A^5$ | H | H | $A^3$ | $A^3$ | Bond |
| 118 | N | $A^6$ | H | H | $A^3$ | $A^3$ | Bond |
| 119 | N | $A^7$ | H | H | $A^3$ | $A^3$ | Bond |
| 120 | N | $A^1$ | $A^1$ | H | $A^3$ | $A^3$ | Bond |
| 121 | N | $A^2$ | $A^1$ | H | $A^3$ | $A^3$ | Bond |
| 122 | N | $A^3$ | $A^1$ | H | $A^3$ | $A^3$ | Bond |
| 123 | N | $A^4$ | $A^1$ | H | $A^3$ | $A^3$ | Bond |
| 124 | N | $A^5$ | $A^1$ | H | $A^3$ | $A^3$ | Bond |
| 125 | N | $A^6$ | $A^1$ | H | $A^3$ | $A^3$ | Bond |
| 126 | N | $A^7$ | $A^1$ | H | $A^3$ | $A^3$ | Bond |
| 127 | N | $A^1$ | H | $A^1$ | $A^3$ | $A^3$ | Bond |
| 128 | N | $A^2$ | H | $A^1$ | $A^3$ | $A^3$ | Bond |
| 129 | N | $A^3$ | H | $A^1$ | $A^3$ | $A^3$ | Bond |
| 130 | N | $A^4$ | H | $A^1$ | $A^3$ | $A^3$ | Bond |
| 131 | N | $A^5$ | H | $A^1$ | $A^3$ | $A^3$ | Bond |
| 132 | N | $A^6$ | H | $A^1$ | $A^3$ | $A^3$ | Bond |
| 133 | N | $A^7$ | H | $A^1$ | $A^3$ | $A^3$ | Bond |
| 134 | N | $A^1$ | $A^1$ | $A^1$ | $A^3$ | $A^3$ | Bond |
| 135 | N | $A^2$ | $A^1$ | $A^1$ | $A^3$ | $A^3$ | Bond |
| 136 | N | $A^3$ | $A^1$ | $A^1$ | $A^3$ | $A^3$ | Bond |
| 137 | N | $A^4$ | $A^1$ | $A^1$ | $A^3$ | $A^3$ | Bond |
| 138 | N | $A^5$ | $A^1$ | $A^1$ | $A^3$ | $A^3$ | Bond |
| 139 | N | $A^6$ | $A^1$ | $A^1$ | $A^3$ | $A^3$ | Bond |
| 140 | N | $A^7$ | $A^1$ | $A^1$ | $A^3$ | $A^3$ | Bond |
| 141 | N | $A^1$ | $A^2$ | H | $A^1$ | $A^1$ | Bond |
| 142 | N | $A^2$ | $A^2$ | H | $A^1$ | $A^1$ | Bond |
| 143 | N | $A^3$ | $A^2$ | H | $A^1$ | $A^1$ | Bond |
| 144 | N | $A^4$ | $A^2$ | H | $A^1$ | $A^1$ | Bond |
| 145 | N | $A^5$ | $A^2$ | H | $A^1$ | $A^1$ | Bond |
| 146 | N | $A^6$ | $A^2$ | H | $A^1$ | $A^1$ | Bond |
| 147 | N | $A^7$ | $A^2$ | H | $A^1$ | $A^1$ | Bond |
| 148 | N | $A^1$ | $A^2$ | H | $A^2$ | $A^1$ | Bond |
| 149 | N | $A^2$ | $A^2$ | H | $A^2$ | $A^1$ | Bond |
| 150 | N | $A^3$ | $A^2$ | H | $A^2$ | $A^1$ | Bond |
| 151 | N | $A^4$ | $A^2$ | H | $A^2$ | $A^1$ | Bond |
| 152 | N | $A^5$ | $A^2$ | H | $A^2$ | $A^1$ | Bond |
| 153 | N | $A^6$ | $A^2$ | H | $A^2$ | $A^1$ | Bond |
| 154 | N | $A^7$ | $A^2$ | H | $A^2$ | $A^1$ | Bond |
| 155 | N | $A^1$ | $A^2$ | H | $A^2$ | $A^2$ | Bond |
| 156 | N | $A^2$ | $A^2$ | H | $A^2$ | $A^2$ | Bond |
| 157 | N | $A^3$ | $A^2$ | H | $A^2$ | $A^2$ | Bond |
| 158 | N | $A^4$ | $A^2$ | H | $A^2$ | $A^2$ | Bond |
| 159 | N | $A^5$ | $A^2$ | H | $A^2$ | $A^2$ | Bond |
| 160 | N | $A^6$ | $A^2$ | H | $A^2$ | $A^2$ | Bond |
| 161 | N | $A^7$ | $A^2$ | H | $A^2$ | $A^2$ | Bond |
| 302 | N | $A^1$ | H | H | $A^1$ | $A^1$ | $A^8$ |
| 303 | N | $A^2$ | H | H | $A^1$ | $A^1$ | $A^8$ |
| 304 | N | $A^3$ | H | H | $A^1$ | $A^1$ | $A^8$ |
| 305 | N | $A^4$ | H | H | $A^1$ | $A^1$ | $A^8$ |
| 306 | N | $A^5$ | H | H | $A^1$ | $A^1$ | $A^8$ |
| 307 | N | $A^6$ | H | H | $A^1$ | $A^1$ | $A^8$ |
| 308 | N | $A^7$ | H | H | $A^1$ | $A^1$ | $A^8$ |
| 309 | N | $A^1$ | $A^1$ | H | $A^1$ | $A^1$ | $A^8$ |
| 310 | N | $A^2$ | $A^1$ | H | $A^1$ | $A^1$ | $A^8$ |
| 311 | N | $A^3$ | $A^1$ | H | $A^1$ | $A^1$ | $A^8$ |
| 312 | N | $A^4$ | $A^1$ | H | $A^1$ | $A^1$ | $A^8$ |
| 313 | N | $A^5$ | $A^1$ | H | $A^1$ | $A^1$ | $A^8$ |
| 314 | N | $A^6$ | $A^1$ | H | $A^1$ | $A^1$ | $A^8$ |
| 315 | N | $A^7$ | $A^1$ | H | $A^1$ | $A^1$ | $A^8$ |
| 316 | N | $A^1$ | H | $A^1$ | $A^1$ | $A^1$ | $A^8$ |
| 317 | N | $A^2$ | H | $A^1$ | $A^1$ | $A^1$ | $A^8$ |
| 318 | N | $A^3$ | H | $A^1$ | $A^1$ | $A^1$ | $A^8$ |
| 319 | N | $A^4$ | H | $A^1$ | $A^1$ | $A^1$ | $A^8$ |
| 320 | N | $A^5$ | H | $A^1$ | $A^1$ | $A^1$ | $A^8$ |
| 321 | N | $A^6$ | H | $A^1$ | $A^1$ | $A^1$ | $A^8$ |
| 322 | N | $A^7$ | H | $A^1$ | $A^1$ | $A^1$ | $A^8$ |
| 323 | N | $A^1$ | $A^1$ | $A^1$ | $A^1$ | $A^1$ | $A^8$ |
| 324 | N | $A^2$ | $A^1$ | $A^1$ | $A^1$ | $A^1$ | $A^8$ |
| 325 | N | $A^3$ | $A^1$ | $A^1$ | $A^1$ | $A^1$ | $A^8$ |
| 326 | N | $A^4$ | $A^1$ | $A^1$ | $A^1$ | $A^1$ | $A^8$ |

-continued

| Cmpd | $Y^1$ | $R^1$ | $R^2$ | $R^3$ | $R^4$ | $R^5$ | L |
|---|---|---|---|---|---|---|---|
| 327 | N | $A^5$ | $A^1$ | $A^1$ | $A^1$ | $A^1$ | $A^8$ |
| 328 | N | $A^6$ | $A^1$ | $A^1$ | $A^1$ | $A^1$ | $A^8$ |
| 329 | N | $A^7$ | $A^1$ | $A^1$ | $A^1$ | $A^1$ | $A^8$ |
| 330 | N | $A^1$ | H | H | $A^2$ | $A^1$ | $A^8$ |
| 331 | N | $A^2$ | H | H | $A^2$ | $A^1$ | $A^8$ |
| 332 | N | $A^3$ | H | H | $A^2$ | $A^1$ | $A^8$ |
| 333 | N | $A^4$ | H | H | $A^2$ | $A^1$ | $A^8$ |
| 334 | N | $A^5$ | H | H | $A^2$ | $A^1$ | $A^8$ |
| 335 | N | $A^6$ | H | H | $A^2$ | $A^1$ | $A^8$ |
| 336 | N | $A^7$ | H | H | $A^2$ | $A^1$ | $A^8$ |
| 337 | N | $A^1$ | $A^1$ | H | $A^2$ | $A^1$ | $A^8$ |
| 338 | N | $A^2$ | $A^1$ | H | $A^2$ | $A^1$ | $A^8$ |
| 339 | N | $A^3$ | $A^1$ | H | $A^2$ | $A^1$ | $A^8$ |
| 340 | N | $A^4$ | $A^1$ | H | $A^2$ | $A^1$ | $A^8$ |
| 341 | N | $A^5$ | $A^1$ | H | $A^2$ | $A^1$ | $A^8$ |
| 342 | N | $A^6$ | $A^1$ | H | $A^2$ | $A^1$ | $A^8$ |
| 343 | N | $A^7$ | $A^1$ | H | $A^2$ | $A^1$ | $A^8$ |
| 344 | N | $A^1$ | H | $A^1$ | $A^2$ | $A^1$ | $A^8$ |
| 345 | N | $A^2$ | H | $A^1$ | $A^2$ | $A^1$ | $A^8$ |
| 346 | N | $A^3$ | H | $A^1$ | $A^2$ | $A^1$ | $A^8$ |
| 347 | N | $A^4$ | H | $A^1$ | $A^2$ | $A^1$ | $A^8$ |
| 348 | N | $A^5$ | H | $A^1$ | $A^2$ | $A^1$ | $A^8$ |
| 349 | N | $A^6$ | H | $A^1$ | $A^2$ | $A^1$ | $A^8$ |
| 350 | N | $A^7$ | H | $A^1$ | $A^2$ | $A^1$ | $A^8$ |
| 351 | N | $A^1$ | $A^1$ | $A^1$ | $A^2$ | $A^1$ | $A^8$ |
| 352 | N | $A^2$ | $A^1$ | $A^1$ | $A^2$ | $A^1$ | $A^8$ |
| 353 | N | $A^3$ | $A^1$ | $A^1$ | $A^2$ | $A^1$ | $A^8$ |
| 354 | N | $A^4$ | $A^1$ | $A^1$ | $A^2$ | $A^1$ | $A^8$ |
| 355 | N | $A^5$ | $A^1$ | $A^1$ | $A^2$ | $A^1$ | $A^8$ |
| 356 | N | $A^6$ | $A^1$ | $A^1$ | $A^2$ | $A^1$ | $A^8$ |
| 357 | N | $A^7$ | $A^1$ | $A^1$ | $A^2$ | $A^1$ | $A^8$ |
| 358 | N | $A^1$ | H | H | $A^2$ | $A^2$ | $A^8$ |
| 359 | N | $A^2$ | H | H | $A^2$ | $A^2$ | $A^8$ |
| 360 | N | $A^3$ | H | H | $A^2$ | $A^2$ | $A^8$ |
| 361 | N | $A^4$ | H | H | $A^2$ | $A^2$ | $A^8$ |
| 362 | N | $A^5$ | H | H | $A^2$ | $A^2$ | $A^8$ |
| 363 | N | $A^6$ | H | H | $A^2$ | $A^2$ | $A^8$ |
| 364 | N | $A^7$ | H | H | $A^2$ | $A^2$ | $A^8$ |
| 365 | N | $A^1$ | $A^1$ | H | $A^2$ | $A^2$ | $A^8$ |
| 366 | N | $A^2$ | $A^1$ | H | $A^2$ | $A^2$ | $A^8$ |
| 367 | N | $A^3$ | $A^1$ | H | $A^2$ | $A^2$ | $A^8$ |
| 368 | N | $A^4$ | $A^1$ | H | $A^2$ | $A^2$ | $A^8$ |
| 369 | N | $A^5$ | $A^1$ | H | $A^2$ | $A^2$ | $A^8$ |
| 370 | N | $A^6$ | $A^1$ | H | $A^2$ | $A^2$ | $A^8$ |
| 371 | N | $A^7$ | $A^1$ | H | $A^2$ | $A^2$ | $A^8$ |
| 372 | N | $A^1$ | H | $A^1$ | $A^2$ | $A^2$ | $A^8$ |
| 373 | N | $A^2$ | H | $A^1$ | $A^2$ | $A^2$ | $A^8$ |
| 374 | N | $A^3$ | H | $A^1$ | $A^2$ | $A^2$ | $A^8$ |
| 375 | N | $A^4$ | H | $A^1$ | $A^2$ | $A^2$ | $A^8$ |
| 376 | N | $A^5$ | H | $A^1$ | $A^2$ | $A^2$ | $A^8$ |
| 377 | N | $A^6$ | H | $A^1$ | $A^2$ | $A^2$ | $A^8$ |
| 378 | N | $A^7$ | H | $A^1$ | $A^2$ | $A^2$ | $A^8$ |
| 379 | N | $A^1$ | $A^1$ | $A^1$ | $A^2$ | $A^2$ | $A^8$ |
| 380 | N | $A^2$ | $A^1$ | $A^1$ | $A^2$ | $A^2$ | $A^8$ |
| 381 | N | $A^3$ | $A^1$ | $A^1$ | $A^2$ | $A^2$ | $A^8$ |
| 382 | N | $A^4$ | $A^1$ | $A^1$ | $A^2$ | $A^2$ | $A^8$ |
| 383 | N | $A^5$ | $A^1$ | $A^1$ | $A^2$ | $A^2$ | $A^8$ |
| 384 | N | $A^6$ | $A^1$ | $A^1$ | $A^2$ | $A^2$ | $A^8$ |
| 385 | N | $A^7$ | $A^1$ | $A^1$ | $A^2$ | $A^2$ | $A^8$ |
| 386 | N | $A^1$ | H | H | $A^3$ | $A^1$ | $A^8$ |
| 387 | N | $A^2$ | H | H | $A^3$ | $A^1$ | $A^8$ |
| 388 | N | $A^3$ | H | H | $A^3$ | $A^1$ | $A^8$ |
| 389 | N | $A^4$ | H | H | $A^3$ | $A^1$ | $A^8$ |
| 390 | N | $A^5$ | H | H | $A^3$ | $A^1$ | $A^8$ |
| 391 | N | $A^6$ | H | H | $A^3$ | $A^1$ | $A^8$ |
| 392 | N | $A^7$ | H | H | $A^3$ | $A^1$ | $A^8$ |
| 393 | N | $A^1$ | $A^1$ | H | $A^3$ | $A^1$ | $A^8$ |
| 394 | N | $A^2$ | $A^1$ | H | $A^3$ | $A^1$ | $A^8$ |
| 395 | N | $A^3$ | $A^1$ | H | $A^3$ | $A^1$ | $A^8$ |
| 396 | N | $A^4$ | $A^1$ | H | $A^3$ | $A^1$ | $A^8$ |
| 397 | N | $A^5$ | $A^1$ | H | $A^3$ | $A^1$ | $A^8$ |
| 398 | N | $A^6$ | $A^1$ | H | $A^3$ | $A^1$ | $A^8$ |
| 399 | N | $A^7$ | $A^1$ | H | $A^3$ | $A^1$ | $A^8$ |
| 400 | N | $A^1$ | H | $A^1$ | $A^3$ | $A^1$ | $A^8$ |
| 401 | N | $A^2$ | H | $A^1$ | $A^3$ | $A^1$ | $A^8$ |
| 402 | N | $A^3$ | H | $A^1$ | $A^3$ | $A^1$ | $A^8$ |
| 403 | N | $A^4$ | H | $A^1$ | $A^3$ | $A^1$ | $A^8$ |
| 404 | N | $A^5$ | H | $A^1$ | $A^3$ | $A^1$ | $A^8$ |
| 405 | N | $A^6$ | H | $A^1$ | $A^3$ | $A^1$ | $A^8$ |
| 406 | N | $A^7$ | H | $A^1$ | $A^3$ | $A^1$ | $A^8$ |
| 407 | N | $A^1$ | $A^1$ | $A^1$ | $A^3$ | $A^1$ | $A^8$ |
| 408 | N | $A^2$ | $A^1$ | $A^1$ | $A^3$ | $A^1$ | $A^8$ |
| 409 | N | $A^3$ | $A^1$ | $A^1$ | $A^3$ | $A^1$ | $A^8$ |
| 410 | N | $A^4$ | $A^1$ | $A^1$ | $A^3$ | $A^1$ | $A^8$ |
| 411 | N | $A^5$ | $A^1$ | $A^1$ | $A^3$ | $A^1$ | $A^8$ |
| 412 | N | $A^6$ | $A^1$ | $A^1$ | $A^3$ | $A^1$ | $A^8$ |
| 413 | N | $A^7$ | $A^1$ | $A^1$ | $A^3$ | $A^1$ | $A^8$ |
| 414 | N | $A^1$ | H | H | $A^3$ | $A^3$ | $A^8$ |
| 415 | N | $A^2$ | H | H | $A^3$ | $A^3$ | $A^8$ |
| 416 | N | $A^3$ | H | H | $A^3$ | $A^3$ | $A^8$ |
| 417 | N | $A^4$ | H | H | $A^3$ | $A^3$ | $A^8$ |
| 418 | N | $A^5$ | H | H | $A^3$ | $A^3$ | $A^8$ |
| 419 | N | $A^6$ | H | H | $A^3$ | $A^3$ | $A^8$ |
| 420 | N | $A^7$ | H | H | $A^3$ | $A^3$ | $A^8$ |
| 421 | N | $A^1$ | $A^1$ | H | $A^3$ | $A^3$ | $A^8$ |
| 422 | N | $A^2$ | $A^1$ | H | $A^3$ | $A^3$ | $A^8$ |
| 423 | N | $A^3$ | $A^1$ | H | $A^3$ | $A^3$ | $A^8$ |
| 424 | N | $A^4$ | $A^1$ | H | $A^3$ | $A^3$ | $A^8$ |
| 425 | N | $A^5$ | $A^1$ | H | $A^3$ | $A^3$ | $A^8$ |
| 426 | N | $A^6$ | $A^1$ | H | $A^3$ | $A^3$ | $A^8$ |
| 427 | N | $A^7$ | $A^1$ | H | $A^3$ | $A^3$ | $A^8$ |
| 428 | N | $A^1$ | H | $A^1$ | $A^3$ | $A^3$ | $A^8$ |
| 429 | N | $A^2$ | H | $A^1$ | $A^3$ | $A^3$ | $A^8$ |
| 430 | N | $A^3$ | H | $A^1$ | $A^3$ | $A^3$ | $A^8$ |
| 431 | N | $A^4$ | H | $A^1$ | $A^3$ | $A^3$ | $A^8$ |
| 432 | N | $A^5$ | H | $A^1$ | $A^3$ | $A^3$ | $A^8$ |
| 433 | N | $A^6$ | H | $A^1$ | $A^3$ | $A^3$ | $A^8$ |
| 434 | N | $A^7$ | H | $A^1$ | $A^3$ | $A^3$ | $A^8$ |
| 435 | N | $A^1$ | $A^1$ | $A^1$ | $A^3$ | $A^3$ | $A^8$ |
| 436 | N | $A^2$ | $A^1$ | $A^1$ | $A^3$ | $A^3$ | $A^8$ |
| 437 | N | $A^3$ | $A^1$ | $A^1$ | $A^3$ | $A^3$ | $A^8$ |
| 438 | N | $A^4$ | $A^1$ | $A^1$ | $A^3$ | $A^3$ | $A^8$ |
| 439 | N | $A^5$ | $A^1$ | $A^1$ | $A^3$ | $A^3$ | $A^8$ |
| 440 | N | $A^6$ | $A^1$ | $A^1$ | $A^3$ | $A^3$ | $A^8$ |
| 441 | N | $A^7$ | $A^1$ | $A^1$ | $A^3$ | $A^3$ | $A^8$ |
| 442 | N | $A^1$ | $A^2$ | H | $A^1$ | $A^1$ | $A^8$ |
| 443 | N | $A^2$ | $A^2$ | H | $A^1$ | $A^1$ | $A^8$ |
| 444 | N | $A^3$ | $A^2$ | H | $A^1$ | $A^1$ | $A^8$ |
| 445 | N | $A^4$ | $A^2$ | H | $A^1$ | $A^1$ | $A^8$ |
| 446 | N | $A^5$ | $A^2$ | H | $A^1$ | $A^1$ | $A^8$ |
| 447 | N | $A^6$ | $A^2$ | H | $A^1$ | $A^1$ | $A^8$ |
| 448 | N | $A^7$ | $A^2$ | H | $A^1$ | $A^1$ | $A^8$ |
| 449 | N | $A^1$ | $A^2$ | H | $A^2$ | $A^1$ | $A^8$ |
| 450 | N | $A^2$ | $A^2$ | H | $A^2$ | $A^1$ | $A^8$ |
| 451 | N | $A^3$ | $A^2$ | H | $A^2$ | $A^1$ | $A^8$ |
| 452 | N | $A^4$ | $A^2$ | H | $A^2$ | $A^1$ | $A^8$ |
| 453 | N | $A^5$ | $A^2$ | H | $A^2$ | $A^1$ | $A^8$ |
| 454 | N | $A^6$ | $A^2$ | H | $A^2$ | $A^1$ | $A^8$ |
| 455 | N | $A^7$ | $A^2$ | H | $A^2$ | $A^1$ | $A^8$ |
| 456 | N | $A^1$ | $A^2$ | H | $A^2$ | $A^2$ | $A^8$ |
| 457 | N | $A^2$ | $A^2$ | H | $A^2$ | $A^2$ | $A^8$ |
| 458 | N | $A^3$ | $A^2$ | H | $A^2$ | $A^2$ | $A^8$ |
| 459 | N | $A^4$ | $A^2$ | H | $A^2$ | $A^2$ | $A^8$ |
| 460 | N | $A^5$ | $A^2$ | H | $A^2$ | $A^2$ | $A^8$ |
| 461 | N | $A^6$ | $A^2$ | H | $A^2$ | $A^2$ | $A^8$ |
| 462 | N | $A^7$ | $A^2$ | H | $A^2$ | $A^2$ | $A^8$. |

8. The compound of claim 1, wherein the compound consists of a compound having the formula:

Formula V

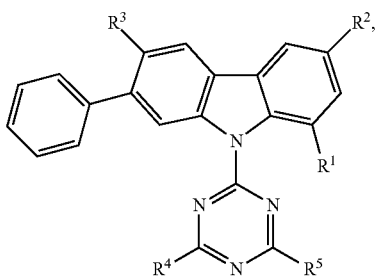

wherein the compound is selected from the group consisting of Compound 771 through Compound 854 listed in the table below, wherein $R^1$, $R^2$, $R^3$, $R^4$, and $R^5$ are as defined and wherein H is hydrogen, $A^1$ is

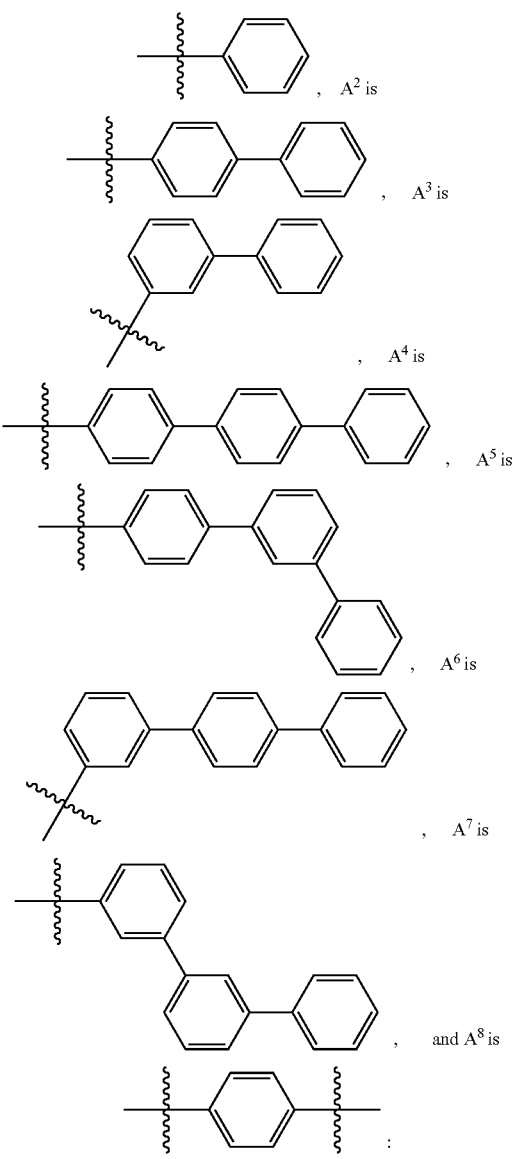

, $A^2$ is , $A^3$ is , $A^4$ is , $A^5$ is , $A^6$ is , $A^7$ is , and $A^8$ is :

| Cmpd | $R^1$ | $R^2$ | $R^3$ | $R^4$ | $R^5$ |
|---|---|---|---|---|---|
| 771 | $A^1$ | H | H | $A^1$ | $A^1$ |
| 772 | $A^2$ | H | H | $A^1$ | $A^1$ |
| 773 | $A^3$ | H | H | $A^1$ | $A^1$ |
| 774 | $A^4$ | H | H | $A^1$ | $A^1$ |
| 775 | $A^5$ | H | H | $A^1$ | $A^1$ |
| 776 | $A^6$ | H | H | $A^1$ | $A^1$ |
| 777 | $A^7$ | H | H | $A^1$ | $A^1$ |
| 778 | $A^1$ | $A^1$ | H | $A^1$ | $A^1$ |
| 779 | $A^2$ | $A^1$ | H | $A^1$ | $A^1$ |
| 780 | $A^3$ | $A^1$ | H | $A^1$ | $A^1$ |
| 781 | $A^4$ | $A^1$ | H | $A^1$ | $A^1$ |
| 782 | $A^5$ | $A^1$ | H | $A^1$ | $A^1$ |
| 783 | $A^6$ | $A^1$ | H | $A^1$ | $A^1$ |
| 784 | $A^7$ | $A^1$ | H | $A^1$ | $A^1$ |
| 785 | $A^1$ | H | $A^1$ | $A^1$ | $A^1$ |
| 786 | $A^2$ | H | $A^1$ | $A^1$ | $A^1$ |
| 787 | $A^3$ | H | $A^1$ | $A^1$ | $A^1$ |
| 788 | $A^4$ | H | $A^1$ | $A^1$ | $A^1$ |
| 789 | $A^5$ | H | $A^1$ | $A^1$ | $A^1$ |
| 790 | $A^6$ | H | $A^1$ | $A^1$ | $A^1$ |
| 791 | $A^7$ | H | $A^1$ | $A^1$ | $A^1$ |
| 792 | $A^1$ | $A^1$ | $A^1$ | $A^1$ | $A^1$ |
| 793 | $A^2$ | $A^1$ | $A^1$ | $A^1$ | $A^1$ |
| 794 | $A^3$ | $A^1$ | $A^1$ | $A^1$ | $A^1$ |
| 795 | $A^4$ | $A^1$ | $A^1$ | $A^1$ | $A^1$ |
| 796 | $A^5$ | $A^1$ | $A^1$ | $A^1$ | $A^1$ |
| 797 | $A^6$ | $A^1$ | $A^1$ | $A^1$ | $A^1$ |
| 798 | $A^7$ | $A^1$ | $A^1$ | $A^1$ | $A^1$ |
| 799 | $A^1$ | H | H | $A^2$ | $A^1$ |
| 800 | $A^2$ | H | H | $A^2$ | $A^1$ |
| 801 | $A^3$ | H | H | $A^2$ | $A^1$ |
| 802 | $A^4$ | H | H | $A^2$ | $A^1$ |
| 803 | $A^5$ | H | H | $A^2$ | $A^1$ |
| 804 | $A^6$ | H | H | $A^2$ | $A^1$ |
| 805 | $A^7$ | H | H | $A^2$ | $A^1$ |
| 806 | $A^1$ | $A^1$ | H | $A^2$ | $A^1$ |
| 807 | $A^2$ | $A^1$ | H | $A^2$ | $A^1$ |
| 808 | $A^3$ | $A^1$ | H | $A^2$ | $A^1$ |
| 809 | $A^4$ | $A^1$ | H | $A^2$ | $A^1$ |
| 810 | $A^5$ | $A^1$ | H | $A^2$ | $A^1$ |
| 811 | $A^6$ | $A^1$ | H | $A^2$ | $A^1$ |
| 812 | $A^7$ | $A^1$ | H | $A^2$ | $A^1$ |
| 813 | $A^1$ | H | $A^1$ | $A^2$ | $A^1$ |
| 814 | $A^2$ | H | $A^1$ | $A^2$ | $A^1$ |
| 815 | $A^3$ | H | $A^1$ | $A^2$ | $A^1$ |
| 816 | $A^4$ | H | $A^1$ | $A^2$ | $A^1$ |
| 817 | $A^5$ | H | $A^1$ | $A^2$ | $A^1$ |
| 818 | $A^6$ | H | $A^1$ | $A^2$ | $A^1$ |
| 819 | $A^7$ | H | $A^1$ | $A^2$ | $A^1$ |
| 820 | $A^1$ | $A^1$ | $A^1$ | $A^2$ | $A^1$ |
| 821 | $A^2$ | $A^1$ | $A^1$ | $A^2$ | $A^1$ |
| 822 | $A^3$ | $A^1$ | $A^1$ | $A^2$ | $A^1$ |
| 823 | $A^4$ | $A^1$ | $A^1$ | $A^2$ | $A^1$ |
| 824 | $A^5$ | $A^1$ | $A^1$ | $A^2$ | $A^1$ |
| 825 | $A^6$ | $A^1$ | $A^1$ | $A^2$ | $A^1$ |
| 826 | $A^7$ | $A^1$ | $A^1$ | $A^2$ | $A^1$ |
| 827 | $A^1$ | H | H | $A^2$ | $A^2$ |
| 828 | $A^2$ | H | H | $A^2$ | $A^2$ |
| 829 | $A^3$ | H | H | $A^2$ | $A^2$ |
| 830 | $A^4$ | H | H | $A^2$ | $A^2$ |
| 831 | $A^5$ | H | H | $A^2$ | $A^2$ |
| 832 | $A^6$ | H | H | $A^2$ | $A^2$ |
| 833 | $A^7$ | H | H | $A^2$ | $A^2$ |
| 834 | $A^1$ | $A^1$ | H | $A^2$ | $A^2$ |
| 835 | $A^2$ | $A^1$ | H | $A^2$ | $A^2$ |
| 836 | $A^3$ | $A^1$ | H | $A^2$ | $A^2$ |
| 837 | $A^4$ | $A^1$ | H | $A^2$ | $A^2$ |
| 838 | $A^5$ | $A^1$ | H | $A^2$ | $A^2$ |
| 839 | $A^6$ | $A^1$ | H | $A^2$ | $A^2$ |
| 840 | $A^7$ | $A^1$ | H | $A^2$ | $A^2$ |
| 841 | $A^1$ | H | $A^1$ | $A^2$ | $A^2$ |
| 842 | $A^2$ | H | $A^1$ | $A^2$ | $A^2$ |
| 843 | $A^3$ | H | $A^1$ | $A^2$ | $A^2$ |
| 844 | $A^4$ | H | $A^1$ | $A^2$ | $A^2$ |
| 845 | $A^5$ | H | $A^1$ | $A^2$ | $A^2$ |
| 846 | $A^6$ | H | $A^1$ | $A^2$ | $A^2$ |
| 847 | $A^7$ | H | $A^1$ | $A^2$ | $A^2$ |
| 848 | $A^1$ | $A^1$ | $A^1$ | $A^2$ | $A^2$ |
| 849 | $A^2$ | $A^1$ | $A^1$ | $A^2$ | $A^2$ |

-continued
| Cmpd | R[1] | R[2] | R[3] | R[4] | R[5] |
|------|------|------|------|------|------|
| 850 | A[3] | A[1] | A[1] | A[2] | A[2] |
| 851 | A[4] | A[1] | A[1] | A[2] | A[2] |
| 852 | A[5] | A[1] | A[1] | A[2] | A[2] |
| 853 | A[6] | A[1] | A[1] | A[2] | A[2] |
| 854 | A[7] | A[1] | A[1] | A[2] | A[2]. |
9. The compound of claim 1, wherein the compound is selected from the group consisting of:
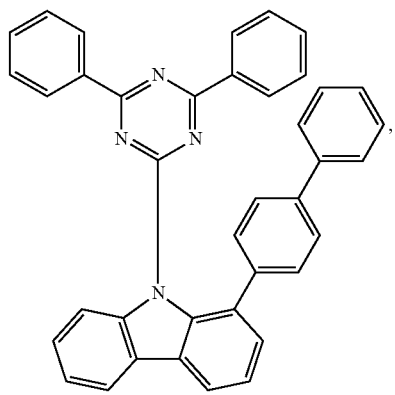
Compound 2
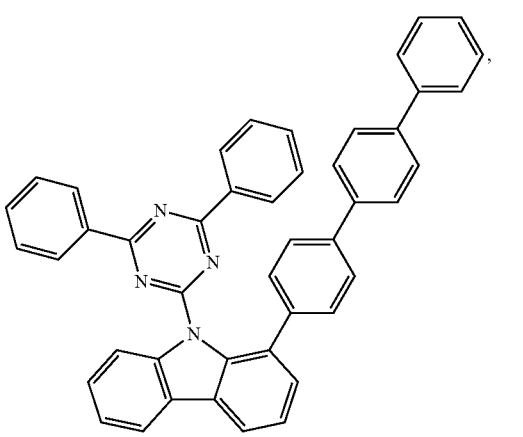
Compound 4
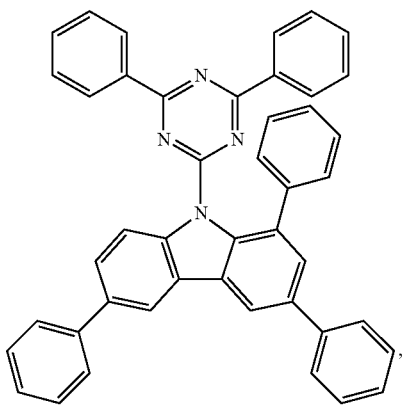
Compound 22
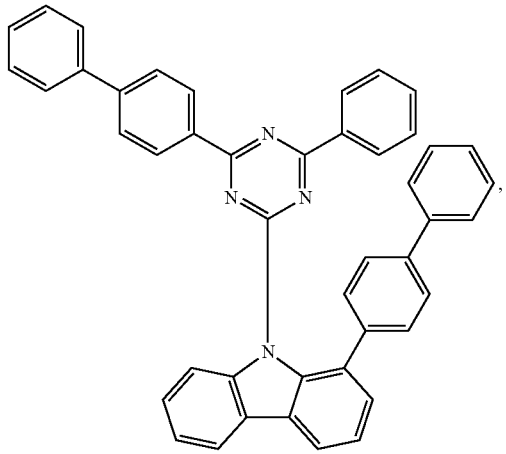
Compound 30
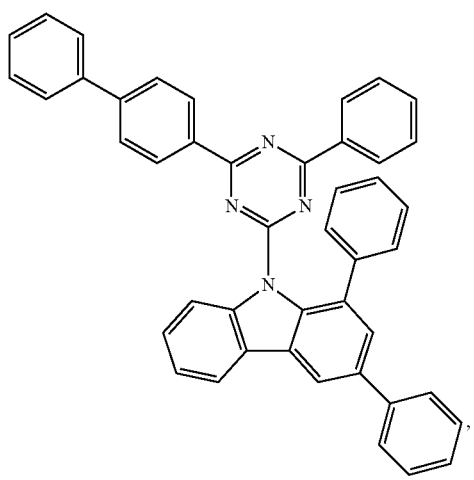
Compound 36
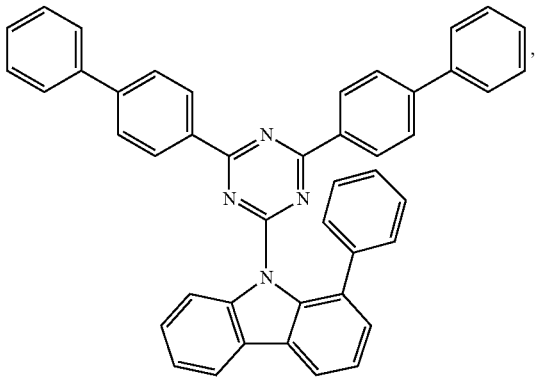
Compound 57

Compound 64

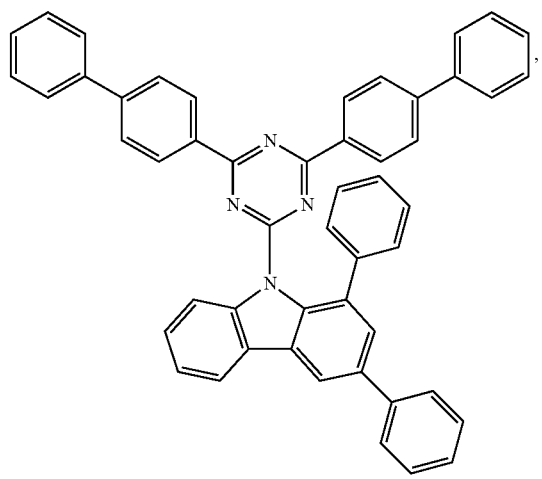

Compound 309

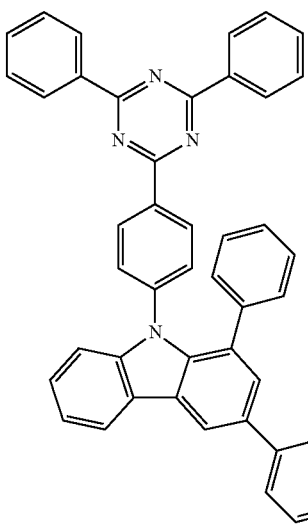

, and

Compound 142

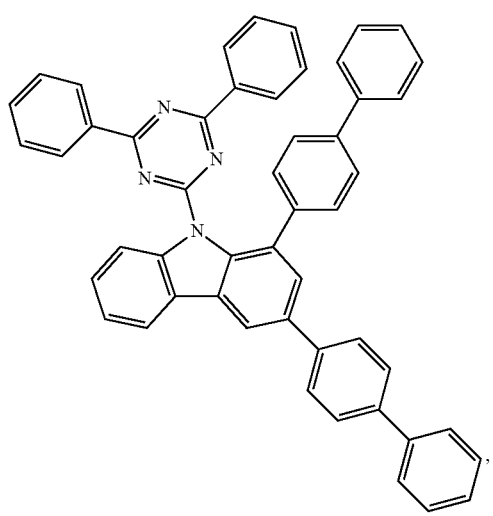

Compound 358

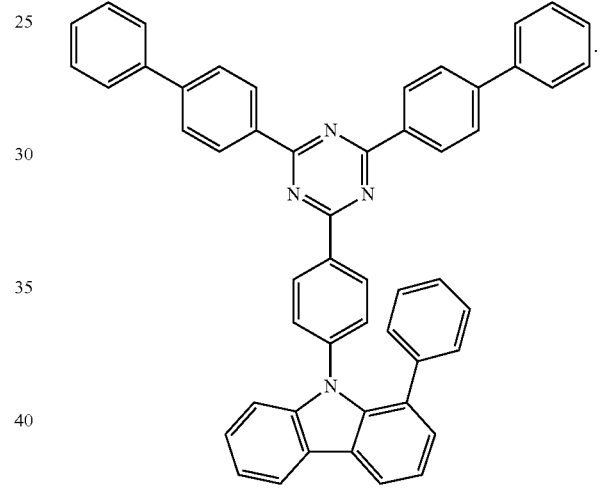

.

10. A formulation comprising a compound of claim 1.
11. A first device comprising a first organic light emitting device, the first organic light emitting device comprising:
   an anode;
   a cathode;
   an organic layer, disposed between the anode and the cathode, wherein the organic layer further comprising a compound having a structure according to Formula I Compound 303

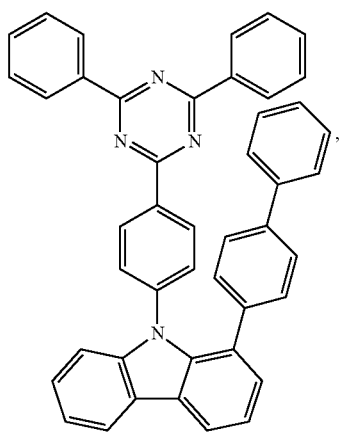

Formula I

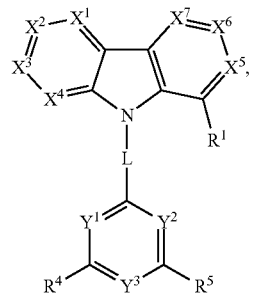

wherein $R^1$, $R^4$ and $R^5$ are independently selected from group consisting of non-fused aryl, non-fused heteroaryl, and combinations thereof;

wherein L is selected from the group consisting of a bond, non-fused aryl, non-fused heteroaryl, and combinations thereof;

wherein $X^1$, $X^2$, $X^3$, $X^4$, $X^5$, $X^6$, and $X^7$ are each CR;

wherein $Y^1$, $Y^2$, and $Y^3$ are N;

and wherein each R can be same or different, and is independently selected from the group consisting of hydrogen, deuterium, non-fused aryl, non-fused heteroaryl and combinations thereof.

12. The first device of claim 11 wherein the first device is an organic light-emitting device, is a consumer product, comprises a lighting panel, or a combination thereof.

13. The first device of claim 11 wherein the compound is selected from the group consisting of:

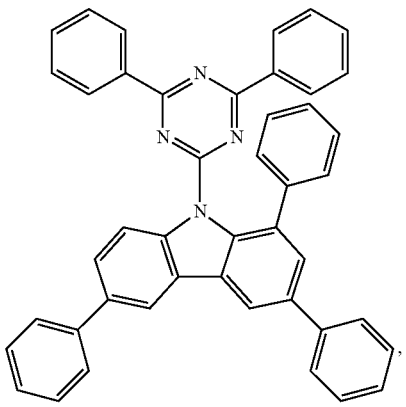

Compound 22

-continued

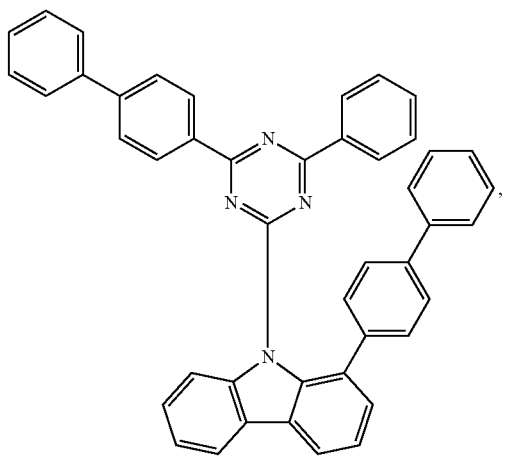

Compound 2

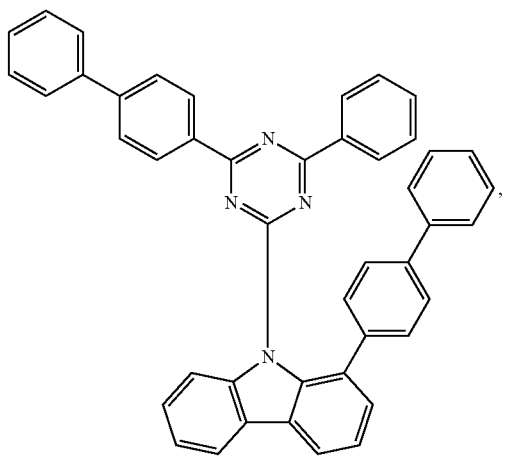

Compound 30

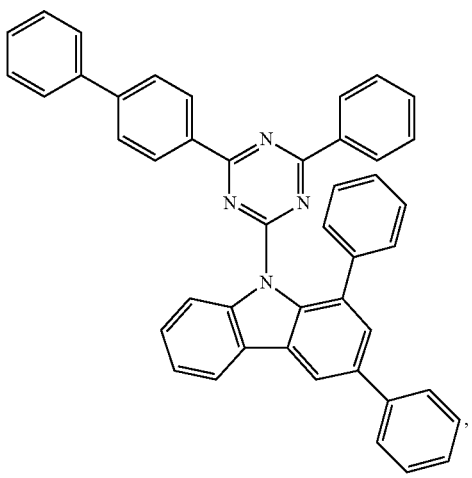

Compound 4

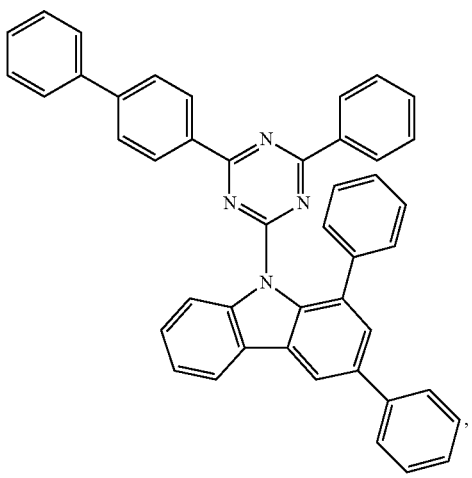

Compound 36

Compound 57
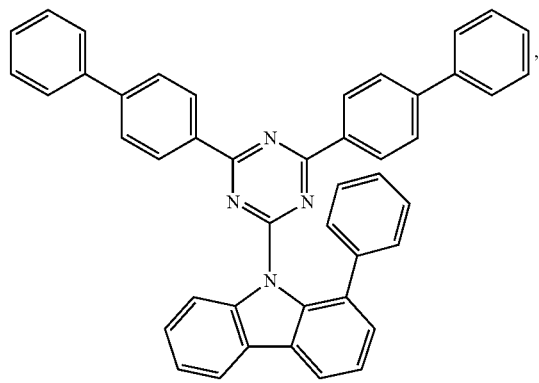
Compound 64
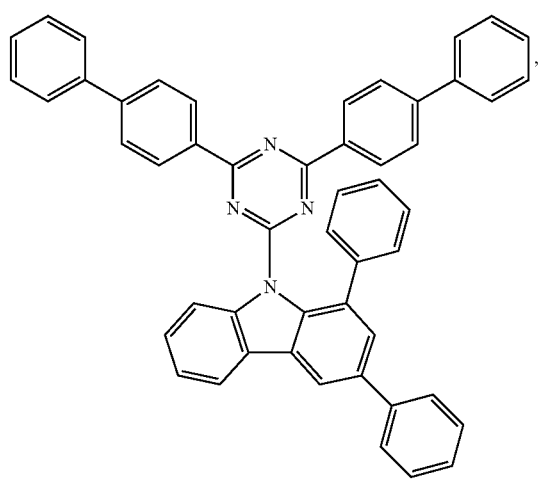
Compound 142
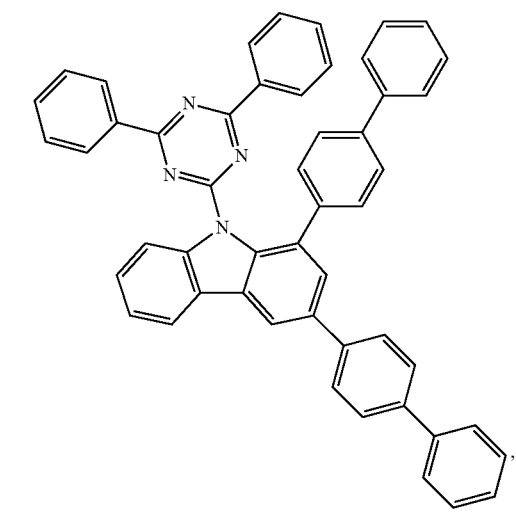
Compound 303
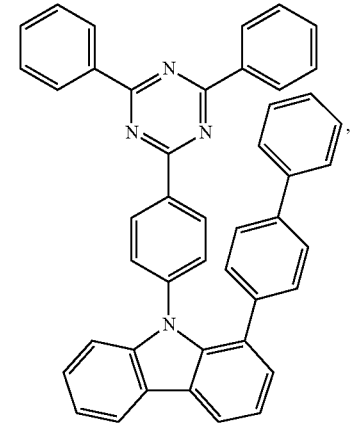
Compound 309
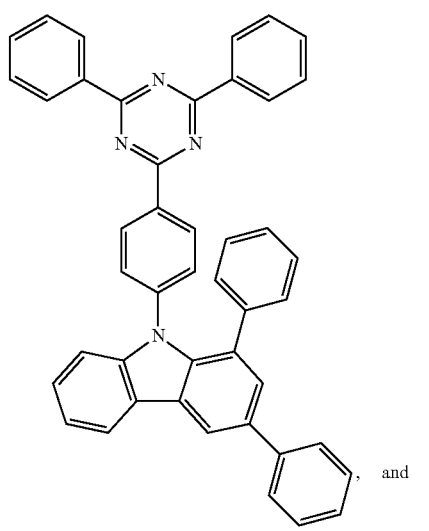
, and
Compound 358
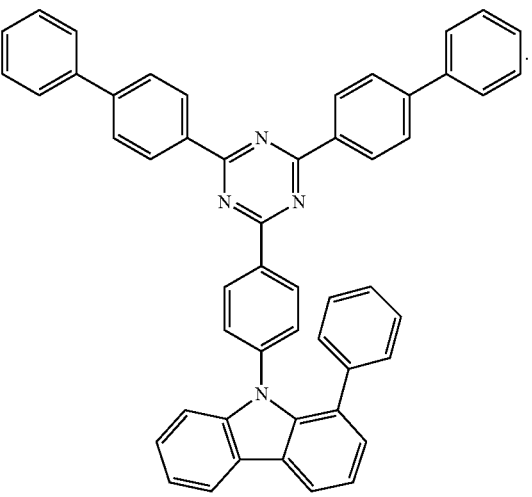
14. The first device of claim 11 wherein the organic layer is an emissive layer and the compound of Formula I is a host.
15. The first device of claim 11 wherein the organic layer is a blocking layer and the compound having the Formula I is a blocking material in the organic layer.

16. The first device of claim 11 wherein the organic layer is an electron transporting layer and the compound having the Formula I is an electron transporting material in the organic layer.

17. The first device of claim 11 further comprising a first dopant material that is an emissive dopant comprising a transition metal complex having at least one ligand or part of the ligand if the ligand is more than bidentate selected from the group consisting of:

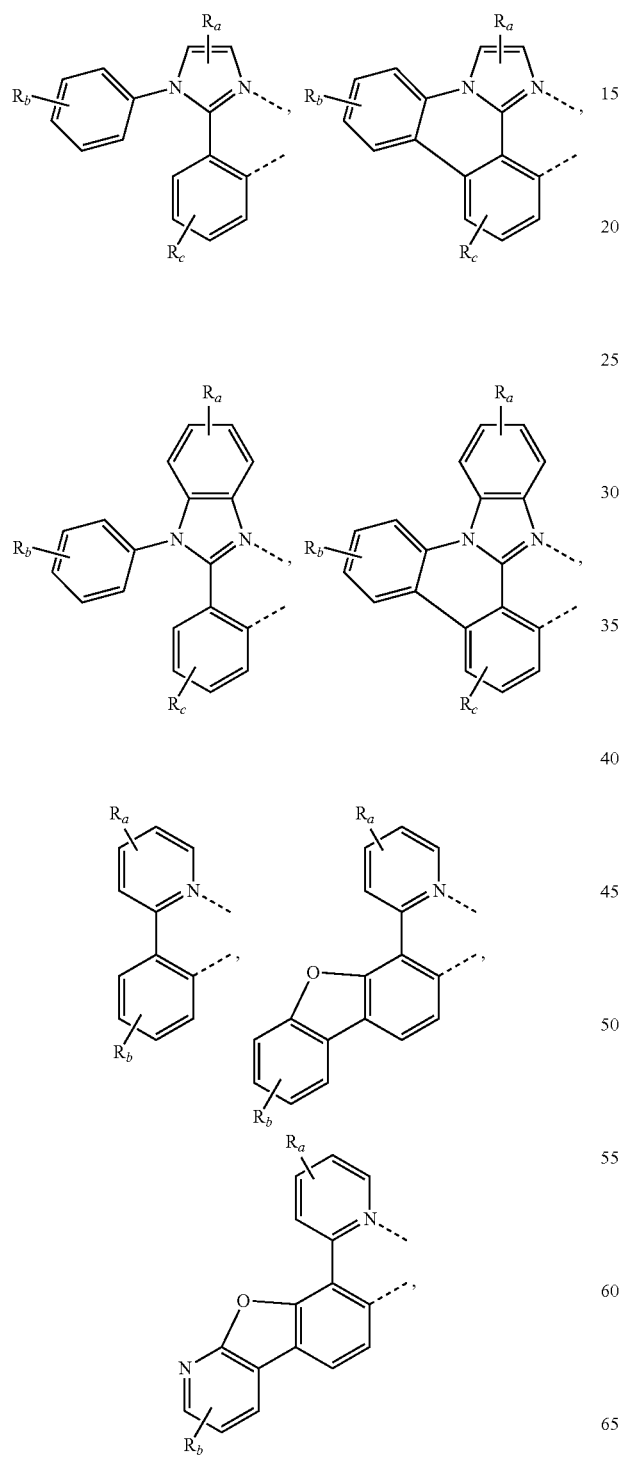
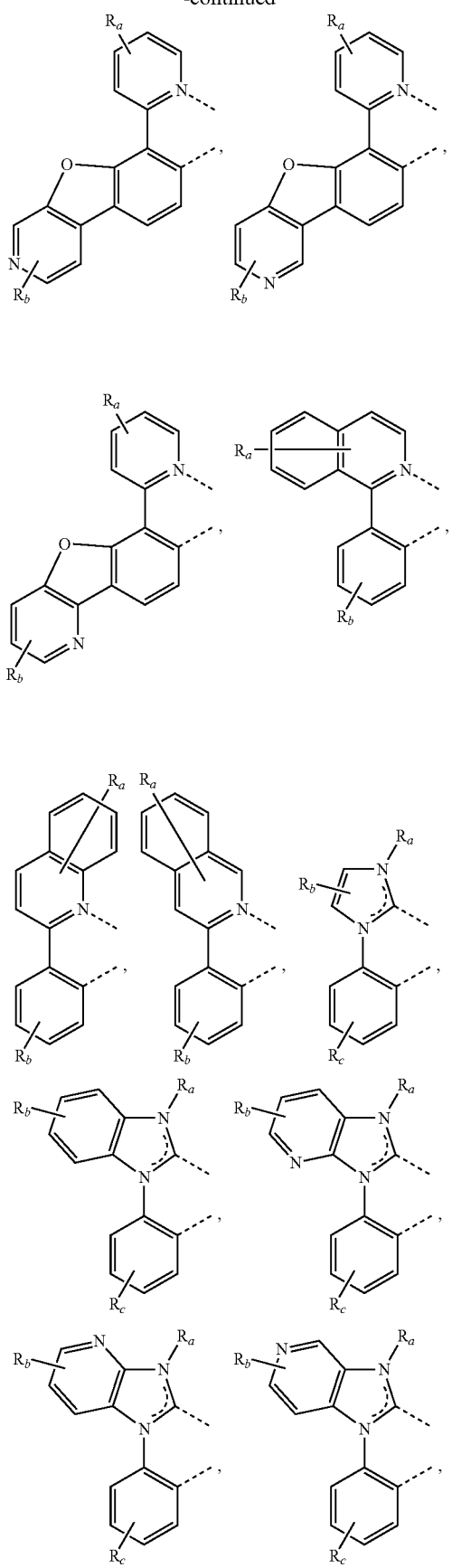

-continued

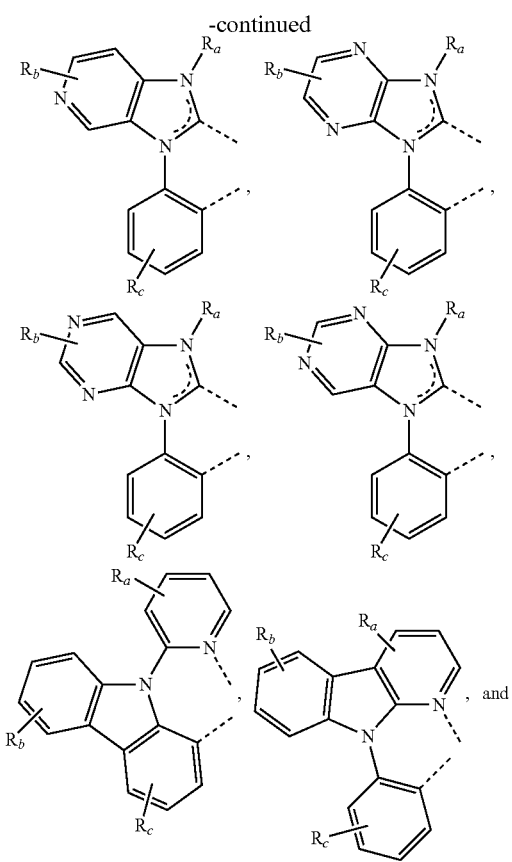

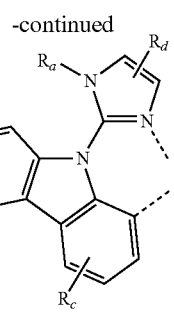

wherein $R_a$, $R_b$, and $R_c$ may represent mono, di, tri or tetra substitutions;

$R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and two adjacent substituents of $R_a$, $R_b$, and $R_c$ are optionally joined to form a fused ring or form a multidentate ligand.

18. The compound of claim 1, wherein $R^1$ is selected from the group consisting of biphenyl, terphenyl, tetraphenyl, pentaphenyl, pyridine, phenyl pyridine and pyridyl phenyl.

19. The compound of claim 1, wherein $R^1$ is non-fused heteroaryl.

* * * * *